US011406832B2

(12) United States Patent
Holbrook et al.

(10) Patent No.: US 11,406,832 B2
(45) Date of Patent: Aug. 9, 2022

(54) PATIENT-INTERMEDIATED THERAPY MANAGEMENT

(71) Applicant: Medtronic, Inc., Minneapolis, MN (US)

(72) Inventors: Reece W. Holbrook, Shoreview, MN (US); Nathan E. Johnson, Shoreview, MN (US); Paul R. Solheim, Blaine, MN (US); Patrick D. Wells, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 481 days.

(21) Appl. No.: 16/047,534

(22) Filed: Jul. 27, 2018

(65) Prior Publication Data

US 2020/0030618 A1    Jan. 30, 2020

(51) Int. Cl.
*A61N 1/37* (2006.01)
*A61N 1/372* (2006.01)
(Continued)

(52) U.S. Cl.
CPC ......... *A61N 1/37247* (2013.01); *A61N 1/025* (2013.01); *A61N 1/36542* (2013.01);
(Continued)

(58) Field of Classification Search
CPC ............ A61N 1/37247; A61N 1/36031; A61N 1/36034; A61N 1/3602; A61N 1/3604;
(Continued)

(56) References Cited

U.S. PATENT DOCUMENTS

| 8,744,572 B1 | 6/2014 | Greenhut et al. |
| 2003/0130703 A1* | 7/2003 | Florio .................. A61N 1/3621 607/11 |

(Continued)

OTHER PUBLICATIONS (PCT/US2019/043376) PCT Notification of Transmittal of the International Search Report and the Written Opinion of the International Searching Authority, dated Jan. Nov. 19, 2019, 10 pages.
(Continued)

*Primary Examiner* — Rex R Holmes
*Assistant Examiner* — Sana Sahand
(74) *Attorney, Agent, or Firm* — Shumaker & Sieffert, P.A.

(57) ABSTRACT

In some examples, controlling delivery of therapy includes using an implantable medical device comprising at least one electrode. Processing circuitry of a system comprising the device may receive, from an application running on a patient personal device, a patient request entered by the patient into the application. The processing circuitry may further determine, based on the patient request, a requested value of a therapy parameter, compare the requested value to information stored in a memory of the medical device system, the information indicating one or more allowable values of the therapy parameter, determine that the requested value is one of the allowable values based on the comparison of the requested value of the therapy parameter to the one or more allowable values, and control the implantable medical device to deliver cardiac pacing via the at least one electrode according to the requested value for a period of time.

36 Claims, 19 Drawing Sheets

(51) Int. Cl.
  *G16H 20/40* (2018.01)
  *A61N 1/02* (2006.01)
  *A61N 1/365* (2006.01)
  *A61N 1/05* (2006.01)

(52) U.S. Cl.
  CPC ..... *A61N 1/37223* (2013.01); *A61N 1/37254* (2017.08); *A61N 1/37258* (2013.01); *G16H 20/40* (2018.01); *A61N 1/057* (2013.01)

(58) Field of Classification Search
  CPC ............ A61N 1/36071; A61N 1/36132; A61N 1/36542; A61N 1/36571
  See application file for complete search history.

(56) References Cited

U.S. PATENT DOCUMENTS

| | | | |
|---|---|---|---|
| 2004/0088020 A1* | 5/2004 | Condie | A61N 1/37247 607/30 |
| 2008/0071150 A1 | 3/2008 | Miesel et al. | |
| 2009/0054948 A1* | 2/2009 | Webb | G16H 40/67 607/31 |
| 2009/0171412 A1 | 7/2009 | Kelly et al. | |
| 2015/0273220 A1* | 10/2015 | Osypka | A61N 1/3712 607/10 |
| 2016/0216768 A1* | 7/2016 | Goetz | G06F 3/038 |
| 2017/0043174 A1 | 2/2017 | Greenhut et al. | |
| 2018/0161581 A1* | 6/2018 | Perryman | A61N 1/37247 |
| 2020/0147388 A1* | 5/2020 | Huertas Fernandez | A61N 1/36171 |

OTHER PUBLICATIONS

"Bluetooth overview," accessed on May 30, 2018, accessed from https://developer.android.com/guide/topics/connectivity/bluetooth.html, 20 pp.

"Bluetooth low energy overview," accessed on May 30, 2018, accessed from https://developer.android.com/ guide/topics/connectivity/bluetooth-le.html, 12 pp.

"About Core Bluethooth," accessed on May 30, 2018, accessed from https://developer.apple.com/library/content/documentation/NetworkingInternetWeb/Conceptual/CoreBluetooth_concepts/AboutCoreBluetooth/Introduction.html#//apple_ref/doc/uid/TP40013257, 4 pp.

"Core Bluetooth," accessed on May 30, 2018, accessed from https://developer.apple.com/documentation/corebluetooth, 4 pp.

Monteil M.D., et al. "Pacemaker-Mediated Tachycardia: Manufacturer Specifics and Spectrum of Cases," PACE Dec. 2015; 38:1489-1498.

Olshansky, "Pacemaker-Meditated Tachycardia," accessed from https://emedicine.medscape.com/article/159645-overview#a2. Aug. 4, 2016, 1 pp.

Johnson, et al., "Custom Pacemaker with Patient Selectable Biking Mode," Medtronic, Oct. 2016, 1 slide.

\* cited by examiner

PATIENT-INTERMEDIATED THERAPY MANAGEMENT

TECHNICAL FIELD

The disclosure relates generally to medical device systems and, more particularly, cardiac therapy delivery by implantable medical devices.

BACKGROUND

Some types of implantable medical devices (IMDs), such as cardiac pacemakers or implantable cardioverter defibrillators, may be used to provide cardiac therapy to a patient via one or more electrodes. Such IMDs may include, or may be part of a system that includes, sensors that detect signals associated with patient parameters such as patient heart rate or patient movement. Some IMDs or systems may determine values of the patient parameters based on detected signals, and may deliver cardiac therapy to the patient according to stored therapy values that correspond to the determined values of the patient parameters.

For example, some IMDs provide cardiac pacing at a rate that may vary over time in response to changes in the physiological state of the patient, which may be referred to as rate-responsive or demand pacing. Physiological parameters that indicate an activity level of a patient may be monitored, such as patient motion, respiration, temperature, blood pressure, blood pH, blood oxygen and/or the lengths of various intervals within a cardiac electrogram of the patient. Such IMDs may adjust the rate at which pacing pulses are delivered to the heart of the patient in the absence of a sensed depolarization, e.g., by adjusting one or more escape intervals, based on the changes in physiological parameters that indicate patient activity level. In general, a rate responsive pacemaker attempts to ensure that the heart rate of a patient is appropriate for the current activity level of the patient.

The rate response behavior is controlled by a number of programmed parameters stored within the DAD. A physician, clinician, or the like, may use an external computing device that communicates with the IMD to program or reprogram these parameters. For example, a physician or clinician may specify ranges of heart rates and the heart rate response, i.e., the relationship between the output of the one or more sensors and the rate at which pacing pulses are delivered to a patient in the absence of a sensed depolarization, within those ranges.

SUMMARY

In general, this disclosure is directed to techniques for controlling the delivery of cardiac therapy (e.g., cardiac pacing) by an IMD to a heart of a patient. Such techniques may include receiving a patient request from an application running on a patient personal device (e.g., a smartphone or a tablet), and determining a requested value of a therapy parameter for cardiac pacing based on the request. A patient request may include an indication of the patient's activity level, particular activity, or a symptom experienced by the patient, and/or may include a request for the IMD to deliver cardiac pacing in a manner that the patient believes to be appropriate for the patient's activity level, particular activity, or symptom, e.g., a request for the particular value of the therapy parameter. The therapy parameters may be a heart rate response parameter or other therapy parameter according to which the IMD delivers cardiac pacing. Such techniques may further include determining that the requested value of the therapy parameter is a value that is allowable for the patient, and controlling the IMD to deliver cardiac pacing according to the requested value of the therapy parameter.

IMBs, such as cardiac pacemakers or implantable cardioverter defibrillators, may be configured to determine current values of one or more patient physiological parameters based on corresponding signals received from sensors of the IMD or of a system including the IMD, and adjust values of one or more parameters according to which the IMD delivers cardiac pacing, based on the determined current values of the one or more patient parameters. For example, the IMB may determine a heart rate of the patient based on a cardiac electrogram signal received from at least one electrode and/or an activity level of the patient. The IMD may determine the activity level based on signals indicative of one or more physiological parameters, such as a signal indicative of movement received from one or more accelerometers. In some examples, the IMB additionally may determine the activity level based on a signal indicative of respiration of the patient, e.g., a transthoracic impedance signal. In some such examples, an IMB may be configured to adjust a rate at which the IMD delivers pacing pulses to the patient's heart based on the determined activity level. For example, the IMD may determine that the signal received from the one or more accelerometers and/or the respiration signal corresponds to a high level of patient activity, such as running, and increase the rate at which the IMD delivers pacing pulses according to a rate stored in memory and associated with the high level of patient activity. Thus, the IMD may provide the patient with an elevated heart rate to support patient activities that correspond to a high level of activity, such as running, and may provide the patient with a lower heart rate when the IMD determines, based on the physiological parameters indicative of patient activity level, that the patient's activity level is not high (e.g., when the patient is walking or resting). In this manner, the IMD may provide cardiac pacing that supports patient activities corresponding to different levels of circulatory demand.

In some instances, however, IMDs configured to adjust values of one or more parameters according to a current patient activity level determined based on signals received from one or more sensors may not accurately identify the patient's actual activity level. For example, an IMD configured to determine a patient activity level based on signals received from one or more accelerometers may determine that the patient's activity level is high whenever signals received from the one or more accelerometers correspond to a level of movement that satisfies a threshold. This may result in the IMD determining that the patient's activity level is high when the patient is sitting in a vehicle traveling over a bumpy surface or participating in other non-strenuous activities that nonetheless result in significant movement. In such examples, the IMD may increase a rate at which the IMD delivers pacing pulses to provide the patient with an elevated heart rate despite the patient's actual activity level not warranting an elevated heart rate. An increase in heart rate when not warranted by the patient's actual activity level may cause the patient to feel lightheaded, be short of breath, have chest pain, or otherwise experience adverse effects.

Similarly, an IMD configured to determine a patient activity level based on signals received from one or more accelerometers may determine that the patient's activity level is not high enough to warrant increasing a rate at which the IMD delivers pacing pulses if the IMD determines that a level of movement corresponding to the signals does not satisfy a threshold. This may result in the IMD determining that the patient's activity is not high (e.g., low), when the patient is participating in an activity that may be strenuous but that nonetheless does not result in significant movement as detected by the one or more accelerometers. For example, activities such as bicycling, swimming, or playing a musical instrument may be more strenuous than an activity such as walking, but produce less of a type of movement quantified by the IMD in determining an activity level of the patient. In such examples, the IMD may not increase a rate at which the IMD delivers pacing pulses despite the patient's actual activity level warranting an elevated heart rate. A non-elevated heart rate when an elevated heart rate is warranted by the patient's actual activity level may cause the patient to feel lightheaded, be short of breath, have chest pain, feel fatigued or tire easily, or otherwise experience adverse effects.

In an attempt to address a lack of increase in heart rate in instances in which a patient's IMD does not increase a rate at which the IMD delivers pacing pulses despite the patient's actual activity level warranting an elevated heart rate, the patient may attempt to cause the one or more accelerometers to produce signals corresponding to a level of movement that satisfies a threshold associated with a high activity level. For example, the patient may tap or otherwise percuss an area of the patient's body near where the IMD is implanted, such as an upper thoracic region. If successful, such an attempt may cause the IMD to determine that the patient's activity level is high enough to warrant increasing a rate at which the IMD delivers pacing pulses, thereby increasing the patient's heart rate.

However, such attempts by the patient to control the IMD may not produce the desired results of causing the IMD to pace the patient's heart at an elevated rate that the patient finds suitable for the patient's actual activity level. For example, the increase in rate at which the IMD delivers pacing pulses resulting from the patient tapping near where the IMD is implanted may not be enough of an increase, or it may be too much of an increase. In such examples, the patient may experience adverse effects that result from a heart rate that is too low or too high for the patient's actual activity level. Moreover, although tapping near where IMD is implanted may cause an increase in the rate at which the IMD delivers pacing pulses, this method does not cause a decrease in the rate at which the IMD delivers pacing pulses if the IMD delivers pacing pulses at an increased rate despite the patient's actual activity level not warranting an elevated heart rate In addition, the increase in rate at which the IMD delivers pacing pulses resulting from the patient tapping near IMD may be of an inappropriate duration. For example, the increase may only be effective until the IMD next determines an activity level of the patient, which may result in a similar lack of increase in heart rate if the patient is still participating in the strenuous activity that does not satisfy a threshold associated with a high activity level. This may result in the patient repeatedly tapping near the IMD during the activity in an attempt to maintain an elevated heart rate, which may result in undesirable fluctuations in the patient's heart rate during the activity that may cause discomfort, reduced patient performance, and/or may distract the patient from the activity. In any examples in which an IMD inaccurately determines a patient's activity level, an inappropriate pacing rate response that may result from such an inaccurate determination may lead to patient discomfort, a reduced ability of the patient to undertake certain activities, or other undesirable clinical outcomes. Other parameters indicative of patient activity level, such as respiration, QT interval length, or temperature, may be sensed and considered as part of a rate response algorithm instead of, or in addition to patient motion via, e.g., an accelerometer. However, even systems considering other parameters may, at times, provide a rate response that the patient does not consider appropriate or adequate.

In addition to or instead of inappropriate pacing rate responses, other IMD functions may cause undesired effects for the patient. For example, an IMD may be configured to deliver managed ventricular pacing (MVP), which may be intended to reduce unnecessary right ventricular pacing. While MVP may reduce some health risks that may be associated with unnecessary right ventricular pacing, MVP also may cause the patient to become symptomatic or otherwise experience undesired effects. For some patients, MVP may not be an essential feature of effective cardiac pacing. In other examples, a vector along which an IMD delivers pacing may inadvertently stimulate the patient's phrenic nerve, which may cause discomfort for the patient. In still other examples, non-essential pacing features that may cause the patient to become symptomatic or otherwise experience undesired effects may include an atrial rate stabilization (ARS) parameter, a post mode-switch overdrive pacing (PMOP) parameter, an atrial preference pacing (APP) parameter, or others.

In any such examples, it may be desirable to at least temporarily deactivate non-essential pacing features or modify a vector along which the IMD delivers pacing, if such features cause the patient to experience undesired effects of cardiac pacing. However, because some IMDs may be configured to accept programming changes only from a clinician-controlled programming device, a patient experiencing undesired effects caused by such a pacing feature may have to visit a clinician in order to have the feature deactivated, until which time the patient may continue to experience the undesired effects.

Thus, although IMDs such as cardiac pacemakers or implantable defibrillators may be capable of delivering appropriate cardiac pacing based on sensor input in some instances, there may be other instances in which the patient would be better able to direct the IMD's behavior by providing input to the IMD. Such input may pertain to the patient's activity or activity level, a duration for which the patient intends to undertake a particular activity or activity level, a desired heart rate, a symptom experienced, and/or an undesired effect experienced. Enabling a patient to provide such input to the IMD and enabling the IMD to deliver cardiac pacing based on such input may provide one or more benefits, such as improved efficacy of cardiac pacing provided by the IMD, reduced burden on a clinician's time, or increased patient engagement in his or her medical treatment, any of which may help improve clinical outcomes.

However, providing a dedicated programming device to the patient with which the patient may provide input to the patient's IMD may have drawbacks. For example, the patient may find it burdensome to learn to use and maintain another device, which likely may be in addition to other personal devices, such as a smartphone and/or a tablet, that the patient already is accustomed to using for various purposes. In such instances, the patient may not consistently engage in providing input to the IMD (e.g., input pertaining to the patient's activity or activity level, duration for which the patient intends to undertake a particular activity or activity level, desired heart rate, symptom experienced, or undesired effect experienced), and thus may not obtain improved clinical outcomes that may result from consistently providing such input. Additionally, or alternatively, the patient may be less likely to keep a dedicated programming device in close proximity to himself or herself, which may result in the patient not having ready access to the programming device when he or she intends to undertake a particular activity or activity level or experiences symptoms. Thus, methods for controlling the delivery of cardiac pacing by an IMD to a heart of a patient may be performed using an application installed on a patient personal device, such as a smartphone and/or tablet, that the patient already is accustomed to using and may be likely to keep close at hand.

Accordingly, techniques described herein may include controlling an IMD to deliver cardiac pacing according to a requested value of a therapy parameter based on a patient request received by the IMD from an application running on a patient personal device. In addition, the techniques described herein may include comparing the requested value of the therapy parameter to one or more allowable values of the therapy parameter, which may be programmed into a memory of the IMD or another device of such a system by a clinician (e.g., via a clinician programming device), in order to determine whether the requested value is one of one or more allowable values. Such allowable values may be a range of allowable values, and may operate as "riverbanks" to contain the cardiac pacing delivered by the IMD within the range of allowable values. After the IMD has delivered cardiac pacing according to the requested value for a period of time, the IMD may revert to delivering cardiac pacing according to a default value of the therapy parameter. Thus, the techniques described herein enable a patient to control therapy delivered by his or her IMD, within limits determined by the patient's clinician, to better suit the patient's needs by using a device with which he or she already may be familiar.

In one example, a method for controlling delivery of therapy using an implantable medical device configured for implantation within a patient, the implantable medical device comprising at least one electrode and configured to deliver cardiac pacing to the patient via the at least one electrode, the method comprising, by processing circuitry of a medical device system comprising the implantable medical device: receiving, from an application running on a patient personal device, a patient request entered by the patient into the application, wherein the application runs on the patient personal device to enable the patient to interact with the medical device system, and receipt of the request from the application indicates that the request was made by the patient; determining, based on the patient request, a requested value of a therapy parameter according to which the implantable medical device is configured to deliver the cardiac pacing; comparing the requested value of the therapy parameter to information stored in a memory of the medical device system, the information indicating one or more allowable values of the therapy parameter; determining that the requested value of the therapy parameter is included in the one or more allowable values of the therapy parameter based on the comparison of the requested value of the therapy parameter to the one or more allowable values of the therapy parameter; and controlling, based on determining that the requested value of the therapy parameter is included in the one or more allowable values, the implantable medical device to deliver the cardiac pacing according to the requested value of the therapy parameter for a period of time.

In another example, a system for controlling delivery of therapy using an implantable medical device configured for implantation within a patient, the system comprising: the implantable medical device comprising at least one electrode and configured to deliver cardiac pacing to the patient via the at least one electrode; and processing circuitry configured to: receive, from an application running on a patient personal device, a patient request entered by the patient into the application, wherein the application runs on the patient personal device to enable the patient to interact with the system, and receipt of the request from the application indicates that the request was made by the patient; determining, based on the patient request a requested value of a therapy parameter according to which the implantable medical device is configured to deliver the cardiac pacing; compare the requested value of the therapy parameter to information stored in a memory of the medical device system, the information indicating one or more allowable values of the therapy parameter; determine that the requested value of the therapy parameter is included in the one or more allowable values of the therapy parameter based on the comparison of the requested value of the therapy parameter to the one or more allowable values of the therapy parameter; and control, based on determining that the requested value of the therapy parameter is included in the one or more allowable values, the implantable medical device to deliver the cardiac pacing according to the requested value of the therapy parameter for a period of time.

In another example, a system for controlling delivery of therapy using an implantable medical device configured for implantation within a patient, the system comprising: the implantable medical device comprising at least one electrode and at least one sensor; and processing circuitry configured to: determine at least one of a first heart rate of the patient based on a first cardiac electrogram signal received from the at least one electrode and a first activity level of the patient based on a first signal received from the at least one sensor; receive, from an application running on a patient personal device, a patient request entered by the patient into the application, wherein the application runs on the patient personal device to enable the patient to interact with the system, and receipt of the request from the application indicates that the request was made by the patient; determine, based on the patient request, a requested value of a therapy parameter according to which the implantable medical device is configured to deliver cardiac pacing; compare the requested value of the therapy parameter to information stored in a memory of the medical device system, the information indicating one or more allowable values of the therapy parameter; determine that the requested value of the therapy parameter is included in the one or more allowable values of the therapy parameter based on the comparison of the requested value of the therapy parameter to the one or more of allowable values of the therapy parameter; determine a first default value of the therapy parameter based on the at least one of the first heart rate of the patient and the first activity level of the patient; determine a difference between the first default value of the therapy parameter and the requested value of the therapy parameter; and determine a weight value corresponding to the requested value of the therapy parameter based on the difference between the first default value of the therapy parameter and the requested value of the therapy parameter; control, based on determining that the requested value of the therapy parameter is included in the one or more allowable values, the implantable medical device to deliver the cardiac pacing based on the weight value and the requested value of the therapy parameter for a period of time; determine that the period of time has elapsed; control the implantable medical device to discontinue delivering therapy according to the requested value of the therapy parameter based on determining that the period of time has elapsed; determine at least one of a second heart rate of the patient based on a second cardiac electrogram signal received from the at least one electrode and a second activity level of the patient based on a second signal received from the at least one accelerometer; determine a second default value of the therapy parameter based on the at least one of the second heart rate of the patient and the second activity level of the patient; and control the implantable medical device to deliver the cardiac pacing according to the second default value of the therapy parameter.

In another example, a system for controlling delivery of therapy using an implantable medical device configured for implantation within a patient, the system comprising: means for receiving, from an application running on a patient personal device, a patient request entered by the patient into the application, wherein the application runs on the patient personal device to enable the patient to interact with the system, and receipt of the request from the application indicates that the request was made by the patient; determining, based on the patient request, a requested value of a therapy parameter according to which the implantable medical device is configured to deliver the cardiac pacing; means for comparing the requested value of the therapy parameter to information stored in a memory of the medical device system, the information indicating one or more allowable values of the therapy parameter; means for determining that the requested value of the therapy parameter is included in the one or more allowable values of the therapy parameter based on the comparison of the requested value of the therapy parameter to the one or more allowable values of the therapy parameter; and means for controlling, based on determining that the requested value of the therapy parameter is included in the one or more allowable values, the implantable medical device to deliver the cardiac pacing according to the requested value of the therapy parameter for a period of time.

In another example, a non-transitory computer-readable medium storing instructions for causing processing circuitry to perform a method for controlling delivery of the cardiac pacing using an implantable medical device configured for implantation within a patient, the implantable medical device comprising at least one electrode and configured to deliver cardiac pacing to the patient via the at least one electrode, the method comprising: receiving, from an application running on a patient personal device, a patient request entered by the patient into the application, wherein the application runs on the patient personal device to enable the patient to interact with a medical device system, and receipt of the request from the application indicates that the request was made by the patient; determining, based on the patient request, a requested value of a therapy parameter according to which the implantable medical device is configured to deliver the cardiac pacing; comparing the requested value of the therapy parameter to information stored in a memory of the medical device system, the information indicating one or more allowable values of the therapy parameter; determining that the requested value of the therapy parameter is included in the one or more allowable values of the therapy parameter based on the comparison of the requested value of the therapy parameter to the one or more allowable values of the therapy parameter; and controlling, based on determining that the requested value of the therapy parameter is included in the one or more allowable values, the implantable medical device to deliver the cardiac pacing according to the requested value of the therapy parameter for a period of time.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

DETAILED DESCRIPTION

Figure 1:
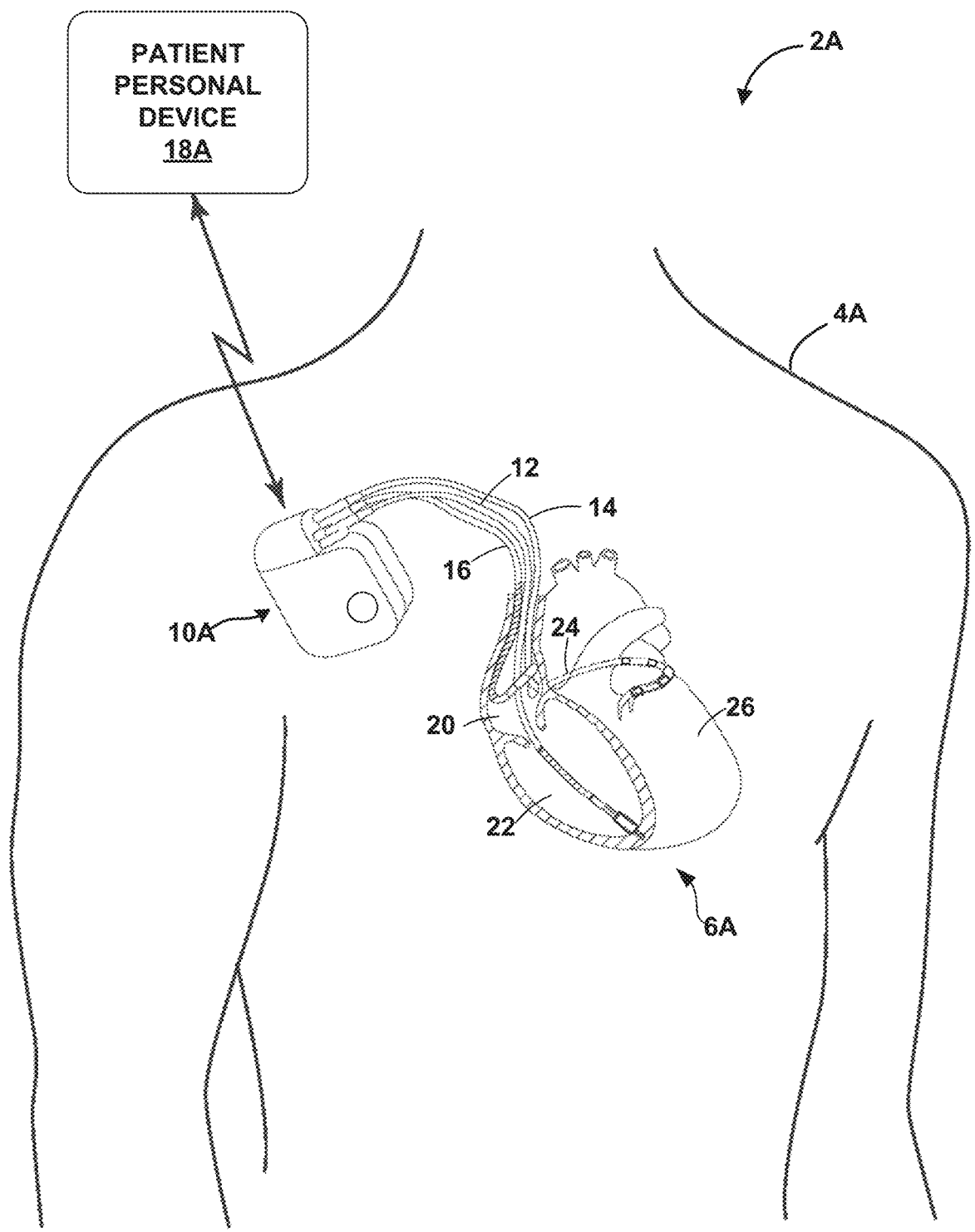
FIG. 1 is conceptual drawing illustrating an example of a medical device system including an implantable medical device and patient personal device in conjunction with a patient.

In general, this disclosure describes example techniques related to controlling the delivery of cardiac therapy (e.g., cardiac pacing) by an IMD to a patient according to a requested value of a therapy parameter. Processing circuitry of the IMD or a system that includes the IMD may determine the requested value of the therapy parameter based on a patient request entered by the patient into an application running on a patient personal device, such as the patient's smartphone or tablet, and received by the processing circuitry. According to the example techniques described herein, the processing circuitry also may compare the requested value of the therapy parameter to one or more allowable values of the therapy parameter, which may be stored in one or more of a memory of the IMD, a memory of the patient personal device, or a server that is accessible by the patient personal device, to ensure that the requested value is one of the one or more allowable values. An IMD used in some of the example techniques may be configured for implantation within the patient, such as subcutaneously, substernally, or within a heart of the patient, and may be configured to deliver the cardiac pacing to the heart of the patient via at least one electrode of the IMD.

The processing circuitry may then determine a default value of the therapy parameter and determine a difference between the default value of the therapy parameter and the requested value of the therapy parameter. In some examples, the processing circuitry may determine the default value based on one or more patient parameters, such as a heart rate of the patient and/or an activity level of the patient, which the processing circuitry respectively may determine based on signals received from one or more electrodes and/or one or more accelerometers. The processing circuitry may determine a weight value based on the difference between the default value of the therapy parameter and the requested value of the therapy parameter, which may influence a duration of the period of time for which the processing circuitry controls the IMD to deliver cardiac pacing according to the requested value of the therapy parameter. In some examples, the processing circuitry also may take into account a difference between the requested value of the therapy parameter and a value of the therapy parameter associated with a therapy program stored in a memory, such as a therapy program corresponding to the activity level of the patient determined by the processing circuitry, in determining the weight value.

For example, if the processing circuitry determines that the difference between the default value of the therapy parameter and the requested value of the therapy parameter does not satisfy a difference threshold, then the weight value determined by the processing circuitry may correspond to a period of time that is longer than a period of time associated with a weight value that corresponds to a difference between a default value of the therapy parameter and a requested value of the therapy parameter that does satisfy a difference threshold. Thus, techniques described herein may allow a patient to receive cardiac therapy in a manner that the patient believes will be appropriate for his or her activities or symptoms at a particular time, while modulating the patient's request by weighting the request based on whether it is corroborated by values of patient parameters determined by the processing circuitry. Although techniques for controlling the delivery of cardiac therapy described herein are described as being techniques for controlling the delivery of cardiac pacing, such techniques may be used to control the delivery of other types of cardiac therapy, such as defibrillation therapy.

Some other techniques may be used to control the delivery of cardiac pacing by an IMD to a patient based on one or more patient parameters, such as a heart rate, activity level, and/or respiration of the patient. Such other techniques may include determining a patient's activity level based on signals received from one or more accelerometers, and delivering cardiac pacing according to a value of a therapy parameter stored in a memory (e.g., a memory of the IMB, a memory of the patient personal device, and/or a server that is accessible by the patient personal device) as being associated with the determined activity level. However, such other techniques may not accurately identify the patient's activity level, which may lead to the IMD delivering cardiac pacing according to one or more values of one or more corresponding therapy parameters that may not be appropriate for the patient's actual activity level, which may cause the patient to experience undesired effects. Inaccurate identification of the patient's activity level may occur when the patient's activity results in more or less movement, as determined by the IMD based on signals received from the one or more accelerometers, than the level of exertion experienced by the patient would suggest. Some activities that may be undertaken by the patient may result in an amount of movement that is seemingly incongruent with the level of exertion experienced by the patient, such as bicycling, swimming, playing a musical instrument, or riding in a vehicle traveling over a bumpy surface.

Although a patient may attempt to mitigate the undesired effects of inaccurate patient activity level determination that may result from such other techniques by tapping over the patient's IMD to increase a rate at which the IMB delivers pacing pulses, such techniques that the patient may undertake in an attempt to control the IMB may provide results that are inaccurate and short-lived. For example, the increase in rate at which the IMD delivers pacing pulses resulting from the patient tapping near where the IMD is implanted may not be enough of an increase to suit the patient's activity, or it may be too much of an increase. Moreover, such attempts cannot reduce a rate at which the IMD delivers pacing pulses if the rate is too high for the patient's activity or modify cardiac pacing parameters other than rate. Further, even if the patient does find such attempts to produce suitable results, the patient may have to repetitively tap over the IMD throughout the patient's activity.

In some example techniques described herein, processing circuitry of a system that includes an IMB implanted in a patient may control the IMB to deliver cardiac pacing the patient's heart according to a requested value of a therapy parameter. The processing circuitry may determine the requested value of the therapy parameter based on a patient request received by the IMB from an application running on a patient personal device (e.g., a personal electronic device such as a smartphone, tablet, or other electronic device that allows a user to provide input). The application may run on the patient personal device to enable the patient to interact with a medical device system that includes the IMD, and receipt of the request by the processing circuitry from the application indicates that the request was made by the patient, e.g., that processing circuitry of the system should treat the request as a patient request rather than, for example, a clinician input. In some cases, the patient request may include the requested value of the therapy parameter, such as a heart rate, or the patient request may be an indication of a particular activity (e.g., bicycling) that may be associated with one or more values of one or more corresponding therapy parameters in a memory of the system. The processing circuitry then may compare the requested value of the therapy parameter to one or more allowable values of the therapy parameter, which may be programmed into the memory of the system (e.g., a memory of the IMB, a memory of the patient personal device, and/or a server that is accessible by the patient personal device) by a clinician, in order to determine whether the requested value is one of one or more allowable values of the therapy parameter. After the IMB has delivered cardiac pacing according to the requested value for a period of time, the IMB may revert to delivering cardiac pacing according to a default value of the therapy parameter. Thus, in some cases, the techniques described herein may provide a patient with a measure of control over the cardiac pacing delivered by an IMD implanted in the patient, which may help ensure that the patient receives cardiac pacing that is tailored to the patient's needs, reduce the incidence of undesired effects resulting from pacing, and which ultimately may provide improved clinical outcomes.

Figure 2:
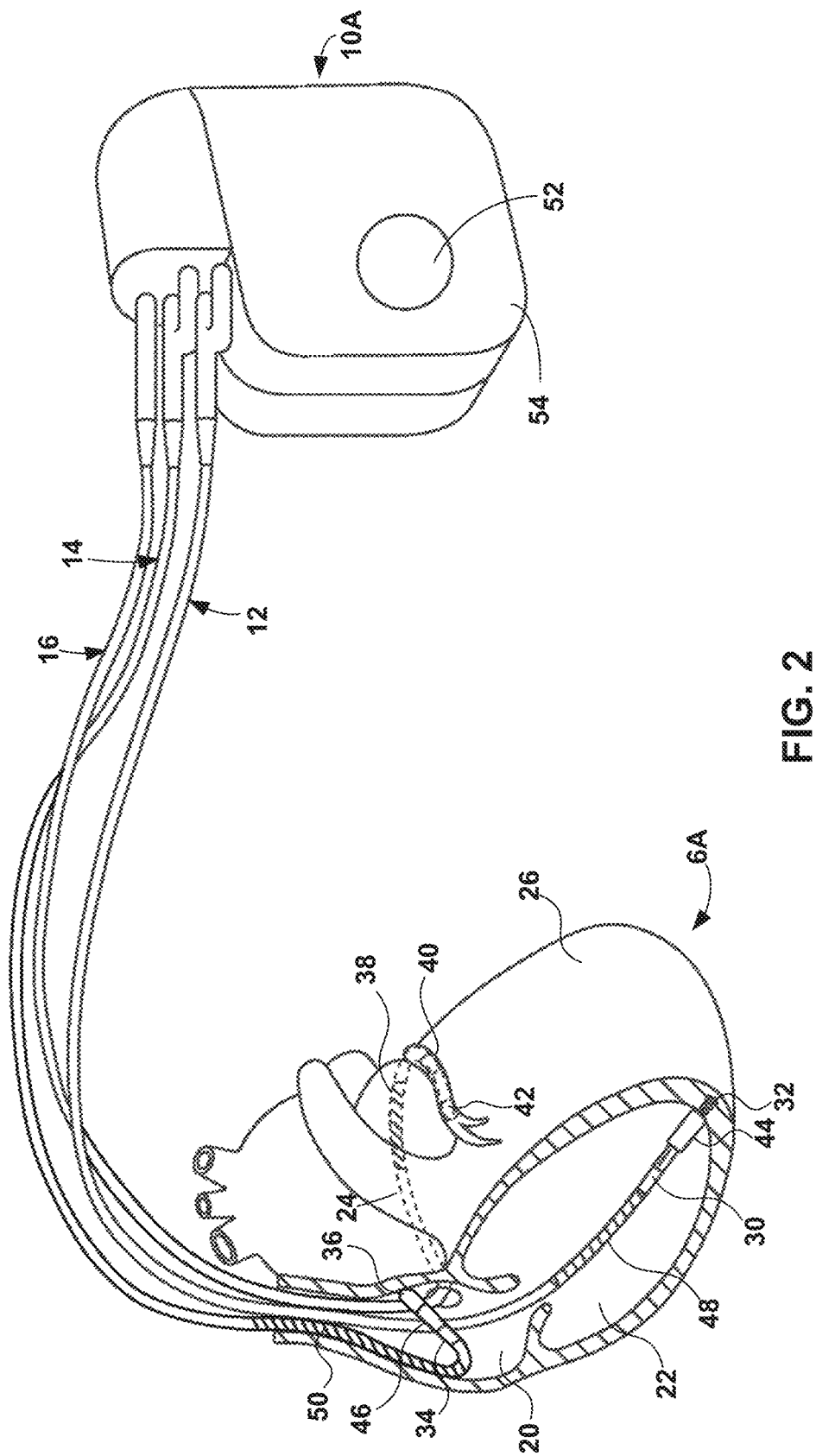
FIG. 2 is a conceptual drawing illustrating an example configuration of the implantable medical device of the medical device system of FIG. 1.

FIGS. 1 and 2 illustrate components of example medical system 2A for controlling one or more IMDs to deliver cardiac therapy (e.g., cardiac pacing or defibrillation) to a patient 4A, in accordance with the example techniques described herein. System 2A includes an IMB 10A and patient personal device 18A. FIG. 1 illustrates the environment of system 2A in conjunction with patient 4A and a heart 6A. The example techniques may be used with an implantable medical device (IMB) 10A, which may be, for example, an implantable cardiac pacemaker, implantable cardioverter/defibrillator (ICD), or pacemaker/cardioverter/defibrillator. In some examples, IMD 10A may be connected to leads 12, 14 and 16, and may be communicatively coupled to patient personal device 18A. In some examples, IMB 10A may be implanted outside of a thoracic cavity of patient 4A (e.g., subcutaneously in the pectoral location illustrated in FIG. 1).

In some examples, IMD 10A may be configured to sense electrical signals corresponding to the depolarization and repolarization of heart 6A, e.g., a cardiac electrogram (EGM), via electrodes on one or more leads 12, 14, and 16 or the housing of IMD 10A. IMD 10A may also deliver therapy in the form of electrical signals to heart 6A via electrodes located on one or more leads 12, 14, and 16 or a housing of IMD 10A. The therapy may be pacing, cardioversion and/or defibrillation pulses, as examples of cardiac therapies. However, for the sake of clarity, the therapy delivered by IMD 10A is primarily discussed herein as being pacing. IMD 10A may monitor EGM signals collected by electrodes on one or more of leads 12, 14, and 16, and based on the EGM signal, diagnose, and treat cardiac episodes.

Leads 12, 14, and 16 extend into heart 6A of patient 4A to sense electrical activity of heart 6A and to deliver electrical stimulation to heart 6A. In the example shown in FIG. 1, right ventricular (RV) lead 12 extends through one or more veins (not shown), the superior vena cava (not shown), and right atrium (RA) 20, and into right ventricle (RV) 22 for sensing right ventricular cardiac signals and delivering pacing or shocking pulses to RV 22. Left ventricular (LV) coronary sinus lead 14 extends through one or more veins, the vena cava, right atrium 20, and into coronary sinus 24 to a region adjacent to the free wall of left ventricle (LV) 26 of heart 6A. In some examples, lead 14 may be used in combination with electrodes of lead 12 and/or lead 16 for delivering electrical shocks for cardioversion and defibrillation therapies. In other examples, coronary sinus lead 14 may also be equipped with a distal tip electrode and ring electrode for pacing and sensing functions in the left chambers of the heart. Right atrial (RA) lead 16 extends through one or more veins and the vena cava and is positioned such that a distal end of lead 16 is in the vicinity of RA and the vena cava for sensing right atrial cardiac signals and delivering pacing or shocking pulses to RA 20.

IMD 10A may sense electrical signals corresponding to the depolarization and repolarization of heart 6A via electrodes (not shown in FIG. 1) coupled to at least one of the leads 12, 14, and 16. In some examples, IMD 10A may also sense electrical signals corresponding to the depolarization and repolarization of heart 6A via extravascular electrodes (e.g., electrodes positioned outside the vasculature of patient 4A), such as epicardial electrodes, external surface electrodes, subcutaneous electrodes, and the like. In any such examples, the configurations of electrodes used by IMD 10A for sensing and pacing may be unipolar or bipolar. In some examples, system 2A may determine heart rate to, e.g., detect arrhythmia, based on the electrical signals sensed via the electrodes.

In some examples, system 2A may sense patient parameters indicative of the activity or exertion level of patient based on electrical signals sensed via the electrodes. For example, system 2A may determine QT interval lengths or other morphological features of the cardiac electrogram sensed via the electrodes. As another example, system 2A may detect respiration based on an impedance between the electrodes, and determine features of the respiration indicative of patient activity, such as rate or depth of the respiration.

In some examples, system 2A may include one or more additional sensors, e.g., for sensing patient activity level, such as one or more accelerometers (not shown) or temperature sensors. The one or more accelerometers may comprise one or more three-axis accelerometers, and may be a component of IMD 10A or a component of another IMD of system 2A. Signals generated by such sensors may be indicative of, for example, gross body movement of patient 4A, such as a patient posture, exertion, temperature, or activity level. Regardless of the configuration of such sensors, processing circuitry of system 2A may determine patient parameter values pertaining to patient posture or activity level based on the signals obtained therefrom, such as whether patient 4A's activity level is low, medium, high, associated with a numeric value, or associated with a particular activity or other value. Although such processing circuitry may be contained within IMD 10A and/or within another IMD or other device of system 2A, e.g., patient personal device 18A, the processing circuitry is described herein as being a component of IMD 10A for the sake of clarity. The processing circuitry of IMD 10A then may use the determined patient parameter values pertaining to posture and/or activity level to determine a default value of a therapy parameter, such as a rate at which to deliver cardiac pacing to heart 6A. As further described below, IMD 10A then may deliver cardiac pacing to heart 6A according to the determined patient parameter value, or may deliver cardiac pacing to heart 6A according to a requested value of the therapy parameter that the processing circuitry may determine based on a patient request received by processing circuitry of IMD 10A from an application running on patient personal device 18A. In some examples, the application may run on patient personal device 18A to enable patient 4A to interact with a medical device system (e.g., system 2A), and receipt of the request by the processing circuitry from the application indicates that the request was made by patient 4A.

In some examples, processing circuitry of IMD 10A may determine a requested value of the therapy parameter by interpreting a patient request, which patient 4A may enter into an application running on patient personal device 18A. In some examples, the patient request may be a request for a desired heart rate. For example, patient 4A may directly request a desired heart rate by requesting desired number of beats per minute, which patient 4A may find adequate for an activity that patient 4A plans to undertake or is currently undertaking. In other examples, patient 4A may indirectly request a desired heart rate by indicating that patient 4A plans to undertake or is currently undertaking a particular activity level (e.g., low, medium, high) or a particular activity (e.g., walking, swimming, bicycling, running, sitting in a vehicle traveling on a bumpy road). In the case of an indirect patient request for a desired heart rate, processing circuitry of IMD 10A may determine a requested value of the heart rate based on a value stored in a memory of system 2A (e.g., of IMD 10A) corresponding to the activity level or activity.

In addition to or instead of including a request for a desired heart rate, a patient request received by processing circuitry of IMD 10A may include a request for a desired value of another therapy parameter according to which IMD 10A may be configured to deliver cardiac pacing. For example, IMD 10A may be configured to deliver cardiac pacing according to an APP mode, which may be intended to maximize atrial pacing percentage to reduce the incidence of atrial tachyarrhythmias. Additionally, or alternatively, IMD 10A may be configured to deliver cardiac pacing according to an MVP mode, which may be intended to reduce unnecessary right ventricular pacing and reduce some health risks that may be associated with unnecessary right ventricular pacing. In some examples, although IMD 10A may be configured to deliver cardiac pacing to heart 6A according to APP and/or MVP pacing modes, such pacing modes may be non-essential to effective cardiac pacing for patent 4A. In still other examples, non-essential pacing features that may cause patient 4A to experience undesired effects may include an ARS parameter, a PMOP parameter, an APP parameter, or others.

In any such examples, patient 4A may be expected to receive some clinical benefit from APP, MVP, ARS, PMOP, or other such pacing modes or parameters, although a clinician treating patient 4A may have determined that such pacing modes are not necessary to effective delivery of cardiac pacing to heart 6A by IMD 10A. However, patient 4A may become symptomatic (e.g., experience symptoms of a health condition or general discomfort) or otherwise experience undesired effects in response to receiving cardiac pacing according to APP, MVP, ARS, PMOP, or other such pacing modes or parameters. In such examples, the patient request entered by patient 4A into patient personal device 18A and received by IMD 10A may include a request to turn off (i.e., disable) the non-essential therapy parameter that may be causing undesired effects. In some such examples, however, a clinician may prevent patient 4A from attempting to modify, via patient request, values of one or more essential therapy parameters, such as by programming IMD 10A not to process patient requests pertaining to such therapy parameters. For example, the clinician may program IMD 10A not to process patient requests pertaining to parameters such as pacing output, sensing thresholds, arrhythmia detection parameters, cardiac resynchronization therapy (CRT) timing parameters, or other such essential therapy parameters that the clinician determines should not be modified by patient 4A.

In other examples, a patient request received by processing circuitry of IMD 10A may include a request for IMD 10A to deliver cardiac pacing along a different electrode vector than an electrode vector along which IMD 10A had been delivering cardiac pacing to heart 6A. For example, a vector along which IMD 10A may deliver cardiac pacing may inadvertently stimulate patient 4A's phrenic nerve, which patient 4A may perceive as being painful or otherwise uncomfortable. In still other examples, a patient request received by processing circuitry of IMD 10A may include a request to suspend delivery of cardiac pacing by IMD 10A while patient 4A undergoes a magnetic resonance imaging (MRI) procedure. In some examples, the magnetic field to which a patient is exposed during an MRI procedure may have the potential to cause undesired effects to a patient who has an IMD such as a pacemaker, such as IMD 10A. For example, the magnetic field may cause unintended cardiac stimulation and/or may otherwise affect the functioning the of IMD 10A, any of which may be uncomfortable and/or cause undesired health effects to patient 4A. Thus, in some examples, it may be desirable to enable an alternate mode of cardiac pacing, which may be more compatible with the MRI environment, by IMD 10A to heart 6A for the duration of an MRI procedure. In addition, enabling patient 4A to suspend delivery of cardiac pacing for the duration of an MRI procedure by entering a patient request into the application running on patient personal device 18A may lessen the burden on clinical staff administering the MRI procedure of properly controlling IMD 10A to suspend cardiac pacing during the procedure.

A patient request to suspend delivery of cardiac pacing for the duration of an MRI procedure may be subject to additional conditions compared to other patient requests. For example, a clinician may program IMD 10A to suspend cardiac pacing based on a patient request pertaining to an MRI procedure only under limited circumstances. In some such examples, the application running on patient personal device 18A may not be enabled to receive a patient request for suspension of cardiac pacing unless patient 4 correctly enters a passcode or provides other authentication, which may be provided by the clinician. In such examples, a passcode or other authentication of a patient request to suspend cardiac pacing for a duration of an MRI procedure enables the application to receive and transmit the request, via patient personal device 18, to IMD 10A. In some examples, the clinician may program IMD 10A, such as via a remote computer, to only accept an authenticated patient request to suspend cardiac pacing during a time when patient 4A is scheduled to undergo an MIll procedure. In any such examples, such restrictions on patient requests to suspend cardiac pacing may protect patient 4A from potentially inappropriate suspension of cardiac pacing.

In some examples, a patient request may include a duration request. For example, in the case of a patient request for a desired heart rate, the patient request also may include a request for IMD 10A to deliver cardiac pacing at the desired heart rate for a particular length of time, such as a duration of time for which patient 4A intends to undertake a particular activity level or activity. In examples in which the patient request includes a request to turn off APP, MVP, ARS, PMOP, or any other non-essential therapy parameter that may be causing undesired effects, an associated length of time may be definite or indefinite. For example, patient 4A may perceive that undesired effects associated with delivery of cardiac pacing by IMD 10A according to APP, MVP, ARS, PMOP, or other such pacing modes or parameters may be more prevalent during some activity levels or activities than during others, in which case a patient request to turn off a non-essential therapy mode or parameter may include a duration of time corresponding to a length of time patient 4A intends to undertake a particular activity level or activity. In other such examples, patient 4A may perceive that undesired effects associated with such non-essential therapy modes or parameters occur regardless of patient 4A's activity level or activity, in which case a patient request may include a request to turn off such non-essential therapy modes or parameters indefinitely.

In any such examples, IMD 10A may compare one or both of a requested value of a therapy parameter and a duration request to information stored in a memory of system 2A (e.g., a memory of IMD 10A, a memory of patient personal device 18A, and/or a memory of a server that is accessible by patient personal device 18A) in order to determine whether the requested value of the therapy parameter is an allowable value of the therapy parameter. As further discussed below with respect to FIG. 8, if IMD 10A determines that the requested value is an allowable value of the therapy parameter, then IMD 10A may deliver cardiac pacing to heart 6A according to the requested value. If IMD 10A determines that the requested value is not an allowable value of the therapy parameter (e.g., not within a range of values known to be safe or potentially effective), then IMD 10 may not deliver cardiac pacing to heart 6A or may truncate delivery of cardiac pacing according to the requested value, e.g., deliver cardiac pacing at the nearest allowable value to the patient's requested value. In some examples in which IMD 10A determines that the requested value is not an allowable value, IMD 10A may transmit an indication of this determination to patient personal device 18A. In such examples, patient personal device 18A may display, via a graphical user interface (GUI) generated by patient personal device 18A within the application, an indication to patient 4A that the requested value is not allowable and/or that IMD 10A will not deliver cardiac pacing according to the requested value.

In some examples in which IMD 10A determines that the requested value is not an allowable value of the therapy parameter, IMD 10A may determine a difference between the requested value and an allowable value (e.g., a nearest allowable value, such as a minimum allowable value or a maximum allowable value). If the difference between the requested value and the nearest allowable value does not satisfy an alternate-value threshold, thereby indicating that the values are sufficiently similar, IMD 10A may determine an alternate value, which may be the nearest allowable value, by which IMD 10A may deliver cardiac pacing. In some such examples, IMD 10A may transmit an indication of the alternate value to patient personal device 18A. In such examples, patient personal device 18A may display, via a graphical user interface (GUI) generated by patient personal device 18A within the application, a query to patient 4A asking patient 4A to revise the patient request to include the alternate value or accept a recommendation to deliver cardiac pacing according to the alternate value. In other such examples, IMD 10A may not transmit an indication of the alternate value to patient personal device 18A, but instead may deliver cardiac pacing according to the alternate value. For example, the difference threshold may indicate that both the non-allowable requested value and the alternate value are near a low end of a range of heart rate values that are allowable for patient 4A, with the non-allowable requested value being close to the lowest allowable value but just outside the range, and the alternate value being the lowest, or close to the lowest, allowable value within the range.

In some examples, IMD 10A deliver cardiac pacing according to a determined weight value, in addition to delivering cardiac pacing based on the requested value. In such examples, the weight value may enable IMD 10A to modify a duration of a period of time requested by patient 4A in connection with the requested value. For example, IMD 10A may cause IMD 10A to deliver cardiac pacing for a shorter period of time than a period of time requested by patient 4A based on the determined weight value. In some such examples, IMD 10A may determine a weight value based on a default value of the therapy parameter. IMD 10A may determine the default value of the therapy parameter based a heart rate of patient 4A, which IMD 10A may determine based on a cardiac electrogram signal received from one or more electrodes of leads 12, 14, 16.

Additionally, or alternatively, IMD 10A may determine the default value of the therapy parameter based on an activity level or activity of patient 4A. In some such examples, IMD 10A may determine the activity level or activity of patient 4A based on signals indicative of one or more physiological parameters of patient 4A. For example, IMD 10A may determine the activity level or activity of patient 4A based on a signal indicative of movement received from an accelerometer, such as an accelerometer of IMD 10A. In some examples, IMD 10A additionally may determine the activity level or activity of patient 4A based on a signal indicative of respiration, a signal indicative of a length of one or more QT intervals of one or more cardiac cycles of patient 4A, and/or a signal indicative of a body temperature of patient 4A. In some such examples, a signal indicative of respiration may be a transthoracic impedance signal received from a pair of electrodes spaced relatively far apart on IMD 10A (e.g., a housing of IMD 10A and an electrode on one of leads 12, 14, or 16). Signals indicative of QT intervals and body temperature respectively may be received from a cardiac electrogram, e.g., from digital signal processing of a wide band cardiac electrogram, and a temperature sensor, which may be a component of IMD 10A or of another medical device of system 2A.

In some examples, the default value of the therapy parameter may correspond to a value of the therapy parameter according to which IMD 10A may deliver cardiac pacing in the absence of a patient request. For example, the default value may be a heart rate value according to which IMD 10A may deliver cardiac pacing when IMD 10A determines that patient 4A has a particular heart rate and/or a particular activity or activity level, and/or after a period of time during which IMD 10A delivers cardiac pacing according to a patient request has expired. Additionally, or alternatively, IMD 10A also may take into account a difference between the requested value of the therapy parameter and a value of the therapy parameter associated with a therapy program stored in a memory, such as a therapy program corresponding to the activity level of the patient determined by the processing circuitry, in determining the weight value.

In some examples, processing circuitry of IMD 10A may determine the weight value by determining whether a difference between the default value of the therapy parameter and the requested value of the therapy parameter, or a difference between a value of the therapy parameter corresponding to a therapy program and the requested value, and by determining whether the difference satisfies a difference threshold. For example, if IMD 10A determines that the difference does not satisfy the difference threshold, IMD 10A may determine that the default value of the therapy parameter and the requested value of the therapy parameter are similar; i.e., that the signals received by IMD 10A from the electrodes and/or accelerometers and the patient request both correspond to the same or substantially similar value of the therapy parameter. In some examples, IMD 10A may determine that a first weight value corresponds to the requested value of the therapy parameter based on determining that the difference does not satisfy the difference threshold. In some such examples, IMD 10A may deliver cardiac pacing for a first period of time associated with the first weight value. In some examples, the first period of time may be the full duration of time associated with the patient request, although in other examples, the first period of time may be less than the full duration of time associated with the patient request. In examples in which IMD 10A determines that the difference satisfies the difference threshold, IMD 10A may determine that a second weight value corresponds to the requested value, and may deliver cardiac pacing for a second period of time that is shorter than the first period of time associated with the first weight value.

In some examples, IMD 10A may attenuate a length of time that IMD 10A delivers cardiac pacing according to the requested value if the requested value of the therapy parameter is sufficiently different from a default value of the therapy parameter. For example, patient 4A may have mistakenly requested a value of a therapy parameter while intending to request a different value. In other examples, patient 4A may have intended to request the requested value of the therapy parameter, but may lack an understanding of which values may be desirable for patient 4A during a particular activity level or activity. In this manner, IMD 10A may limit the duration of time that IMD 10A may deliver cardiac pacing according to a value of a therapy parameter that may be allowable but nonetheless not ideal for patient 4A.

In some examples, an application running on patient personal device 18A may enable patient 4A to indicate a symptom or undesired effect experienced by patient 4A. For example, patient 4A may enter a symptom or undesired effect experienced by patient 4A before, during, and/or after receiving cardiac pacing from IMD 10A according to a default value of a therapy parameter or a value of a therapy parameter associated with a patient request. In some such examples, patient 4A also may enter a severity of a symptom or an undesired effect experienced by patient 4 in association with delivery of cardiac pacing by IMD 10A according to the default value or the value associated with the patient request. In some examples, patient 4A may enter a perceived efficacy of the delivery of cardiac pacing by IMD 10A during or after the delivery thereof. For example, patient 4A may enter a perceived efficacy of the cardiac pacing in response to a prompt from the application running on patient personal device 18 for patient 4A to provide feedback pertaining to a symptom, undesired effect, and/or the efficacy of cardiac pacing. In other such examples, IMD 10A may determine an efficacy of the delivery of cardiac pacing according to the default value or the requested value by comparing the severity of a symptom and/or undesired event entered by patient 4A before the delivery of cardiac pacing to the severity of the symptom and/or undesired event entered by patient 4A during and/or after the delivery of such cardiac pacing.

In any such examples, system 2A may monitor patient requests and/or patient indications of symptoms, undesired effects, or efficacy of cardiac pacing delivered by IMD 10A. For example, system 2A may store one or more aspects of patient requests entered by patient 4A into the application, such as requested values, requested durations, and/or associated default values, in a memory of system 2A. In addition, system 2A may transmit such aspects of the patient requests to a remote computer, such as a computer located with a clinician. In some examples, IMD 10A may store efficacy determinations in the memory of system 2A in association with delivery of cardiac therapy according to default values and/or requested values, and may transmit one or more efficacy indications based on such determinations to the remote computer. For example, IMD 10A may transmit an efficacy indication of a therapy parameter according to which IMD 10 has delivered cardiac pacing, in association with one or more of a patient request according to which the cardiac pacing was delivered, a default value determined by IMD 10A (which also may be associated with the patient request), or a heart rate and/or activity level associated with the delivery of the cardiac pacing.

In some examples, IMD 10A may transmit data pertaining to the patient requests, default values, and/or efficacy indications to the remote computer when IMD 10A has received a threshold number of patient requests, at an expiration of a particular time period, or on any other suitable basis. A clinician may receive the one or more efficacy indications via the remote computer and may determine whether the allowable values of the therapy parameter stored in a memory of system 2A (e.g., a memory of IMD 10A, a memory of patient personal device 18A, and/or a server that is accessible by patient personal device 18A) remain appropriate for patient 4A based, at least in part, on the efficacy indications. In some examples, allowable values stored in a memory of system 2A may no longer be appropriate for patient 4A if a health condition of patient 4A has changed since the clinician last programmed system 2A with therapy parameter values allowable for patient 4A, or if patient 4A's pacing needs otherwise have changed. In some such examples, the clinician may enter one or more updated allowable values of the therapy parameter into the remote computer, such as based on the indication of the efficacy of cardiac pacing. IMD 10A then may receive the updated allowable values of the therapy parameter from the remote computer, and may store the updated allowable values of the therapy parameter in the memory of system 2A.

Additionally, or alternatively, the clinician may determine that one or more default values of the therapy parameter are no longer appropriate for patient 4A, based, at least in part on the indication of the efficacy of cardiac pacing. In some such examples, the clinician may enter one or more updated default values of the therapy parameter into the remote computer based on the indication of the efficacy of cardiac pacing, such as via a clinician programming device (not shown) that is separate from patient personal device 18A. IMD 10A then may receive the updated default values of the therapy parameter from the remote computer, and may store the updated default values of the therapy parameter in the memory of system 2A. In this manner, the clinician may remotely re-program IMD 10A to provide appropriate cardiac therapy to patient 4A on an as-needed basis, without necessarily requiring patient 4A to visit the clinician. However, if the clinician determines, such as based on the indication of efficacy or other medical considerations, that patient 4A requires additional medical attention, the clinician may transmit, via the remote computer, instructions to patient personal device 18A for patient 4A to schedule a visit with the clinician or seek other medical attention.

As described above, enabling patient 4A to provide input to IMD 10A, such as in the form of the patient requests, entry of symptoms, entry of undesired effects, and/or indications of the perceived efficacy of cardiac pacing delivered by IMD 10A described above, may provide one or more benefits, such as improved efficacy of cardiac pacing provided by the IMD, reduced burden on a clinician's time, or increased patient engagement in his or her medical treatment, one or more of which may help improve clinical outcomes and/or reduce healthcare expenses. The manner in which patient 4A may be enabled to provide such input to IMD 10A (e.g., via an application running on patient personal device 18A), may provide further benefits. For example, patient 4's pre-existing familiarity with patient personal device 18A, and/or patient 4A's likely pre-existing inclination to use patient personal device 18A for various tasks, may make patient 4A more likely to provide input to IMD 10A via the application running on patient personal device 18A relative to a separate programmer for IMD 10A. In turn, patient 4A may be more likely to obtain improved clinical outcomes that may result from consistently providing such input to IMD 10A, such as a reduction in symptoms and undesired effects and/or an increase in ability to participate in and enjoy activities, than other examples in which a patient may be given a separate programmer with which to provide input to an IMD.

As described above, the application running on patient personal device 18A may be used to control the functioning of IMD 10A by causing IMD 10A to deliver cardiac pacing according to a requested value of a therapy parameter based on patient requests. In some examples, a remote computer (e.g., a device located with a clinician) may be used to interrogate IMD 10A to retrieve data, which may include device operational data. physiological data, and/or cardiac pacing efficacy data accumulated in a memory of IMD 10A or other component of system 2A. Such interrogation may occur automatically according to a schedule, such as when patient 4A has made a threshold number of patient requests and/or other data inputs, when a time period has expired, or in response to a remote or local user command. Programmers, external monitors, and consumer devices are examples of external devices that may be used to interrogate IMD 10.

Examples of communication techniques used by IMD 10 and an external device include radiofrequency (RF) telemetry, which may be an RF link established via Bluetooth, Wi-Fi, or medical implant communication service (MICS). In some examples, an external device may include a user interface configured to allow a clinician to remotely interact with IMD 10.

Medical device system 2A is an example of a medical device system configured to deliver cardiac therapy (e.g., cardiac pacing) to heart 6A of patient 4A based on one or more requested values of one or more therapy parameters corresponding to a patient request entered by patient 4A into an application running on patient personal device 18A, monitor and store data input by patient 4A into the application, and transmit an indication of efficacy of the cardiac pacing delivered by IMD 10A to a clinician via a remote computer (i.e., an external device). The techniques described herein may be performed by processing circuitry of a device of medical device system 2A, such as processing circuitry of IMD 10A. Additionally, or alternatively, the techniques described herein may be performed, in whole or in part, by processing circuitry of patient personal device 18A, processing circuitry of an external device located with a clinician, and/or by processing circuitry of one or more other implanted or external devices or servers not shown in FIG. 1, some of which are discussed in further detail below with respect to FIG. 7. Examples of the one or more other implanted or external devices may include an implantable monitoring device having one or more sensors, a blood analyzer, an external monitor, or a drug pump. The communication circuitry of each of the devices of medical device system 2A may allow the devices to communicate with one another. In addition, although electrodes and/or accelerometers are described herein as being components of IMD 10A, in other examples, such electrodes and/or accelerometers may be components of another device implanted in or external to patient 4A, such as a subcutaneously implantable monitoring device configured to monitor patient physiological parameters. In such examples, IMD 10A may include processing circuitry configured to receive signals from the electrodes and/or accelerometers on the respective devices and/or communication circuitry configured to transmit the signals from the electrodes or optical sensors to another device (e.g., an external device located with a clinician) or server.

FIG. 2 is a conceptual diagram illustrating IMD 10A and leads 12, 14, and 16 of system 2A in greater detail. In the illustrated example, lead 12 includes bipolar electrodes 30 and 32, which may be located adjacent to a distal end of lead 12. Lead 14 includes bipolar electrodes 34 and 36, which may be located adjacent to a distal end of lead 14. Lead 16 may be a quadrupolar LV lead and includes electrodes 38, 40, and 42, which may be located adjacent to a distal end of lead 16. In some examples, electrodes 38, 40, and/or 42 of lead 16 may be segmented electrodes having a plurality of discrete electrodes arranged at respective circumferential positions around the circumference of lead 16.

In some examples, electrodes 30, 38, 40, and 42 may be ring electrodes, and electrodes 34 and 36 may be extendable helix tip electrodes, the latter of which may be mounted retractably within insulative electrode heads 44 and 46, respectively. Leads 14 and 16 may also respectively include elongated electrodes 48 and 50, each of which may be coil electrodes. In some examples, electrodes 30, 32, 34, 36, 38, 40, and 42 may be electrically coupled to a respective conductor within a lead body of a corresponding one of leads 12, 14, and 16, and thereby coupled to circuitry within IMD 10A. The electrode combinations and positioning of the leads 12, 14, and 16 are meant to be illustrative and should not be understood to be limiting.

The illustrated numbers and configurations of leads 12, 14, and 16 and electrodes are exemplary and should not be considered limiting, as other configurations (e.g., the number and position of leads and electrodes) may be used. In some examples, system 2A may include an additional lead or lead segment having one or more electrodes positioned at different locations in the cardiovascular system for sensing and/or delivering cardiac pacing to patient 4A. For example, instead of or in addition to leads 12, 14, and 16, system 2A may include one or more epicardial or extravascular (e.g., subcutaneous or substernal) leads not positioned within heart 6A.

In some examples, IMD 10A may include one or more housing electrodes, such as housing electrode 52 illustrated in FIG. 2. Housing electrode 52 may be formed integrally with an outer surface of hermetically-sealed housing 54 of IMD 10A, or otherwise may be coupled to housing 54. In some examples, housing electrode 52 may be defined by an uninsulated portion of an outward facing portion of housing 54 of IMD 10A. In some examples, housing 54 may define one or more additional housing electrodes, which may be defined by corresponding divisions between insulated and uninsulated portions of housing 54. In still other examples, substantially all of housing 54 may be uninsulated, such that substantially all of housing 54 defines housing electrode 52.

In some examples, IMD 10A may be configured for bipolar sensing of electrical signals corresponding to a cardiac electrogram of heart 6A via any bipolar combination of electrodes 30, 32, 34, 36, 38, 40, 42, 48, and 50. In other examples, IMD 10A may be configured for unipolar sensing of electrical signals corresponding to a cardiac electrogram of heart 6A via any one of electrodes 30, 32, 34, 36, 38, 40, 42, 48, and 50 in combination with housing electrode 52 on housing 54. In any such examples, IMD 10A may be configured to deliver cardiac therapy (e.g., cardiac pacing) to heart 6A via any combination of electrodes 30, 32, 34, 36, 38, 40, 42, 48, and 50.

As discussed in further detail below with respect to FIG. 5, housing 54 may enclose one or more accelerometers, therapy delivery circuitry, which may be configured to generate therapeutic stimulation, such as cardiac pacing, cardioversion, and defibrillation pulses, and sensing circuitry configured to sense electrical signals corresponding to a cardiac electrogram signal of patient 4A and/or an activity level or activity of patient 4A. Housing 54 also may enclose and one or more of a memory for storing default and/or allowable values of one or more therapy parameters, diagnostics, feedback from patient 4A, and/or therapy programs that may include values of one or more therapy parameters. Housing 54 further may enclose communication circuitry configured for communication between IMD 10A and patient personal device 18A and/or other devices, such as an external device located with a clinician or a server. Such components may enable IMD 10A to carry out one or more aspects of the techniques described herein, such as receiving a patient request entered by patient 4A into the application running on patient personal device 18A and delivering cardiac pacing to heart 6A according to a requested value associated with the patient request, a weight value, and/or a default value.

Although described herein in the context of example IMD 10A, the techniques for controlling the delivery of cardiac pacing described herein may be implemented with any type of IMD configured to deliver cardiac pacing. In some examples, the techniques described herein may be implemented with a transcatheter pacemaker configured for implantation within the heart, such as the Micra™ transcatheter pacing system commercially available from Medtronic plc of Dublin, Ireland and described in further detail with respect to FIGS. 3 and 4. In some examples, system 2A also may include an implantable monitoring device, such as the Reveal LINQ™, also commercially available from Medtronic plc.

Figure 3:
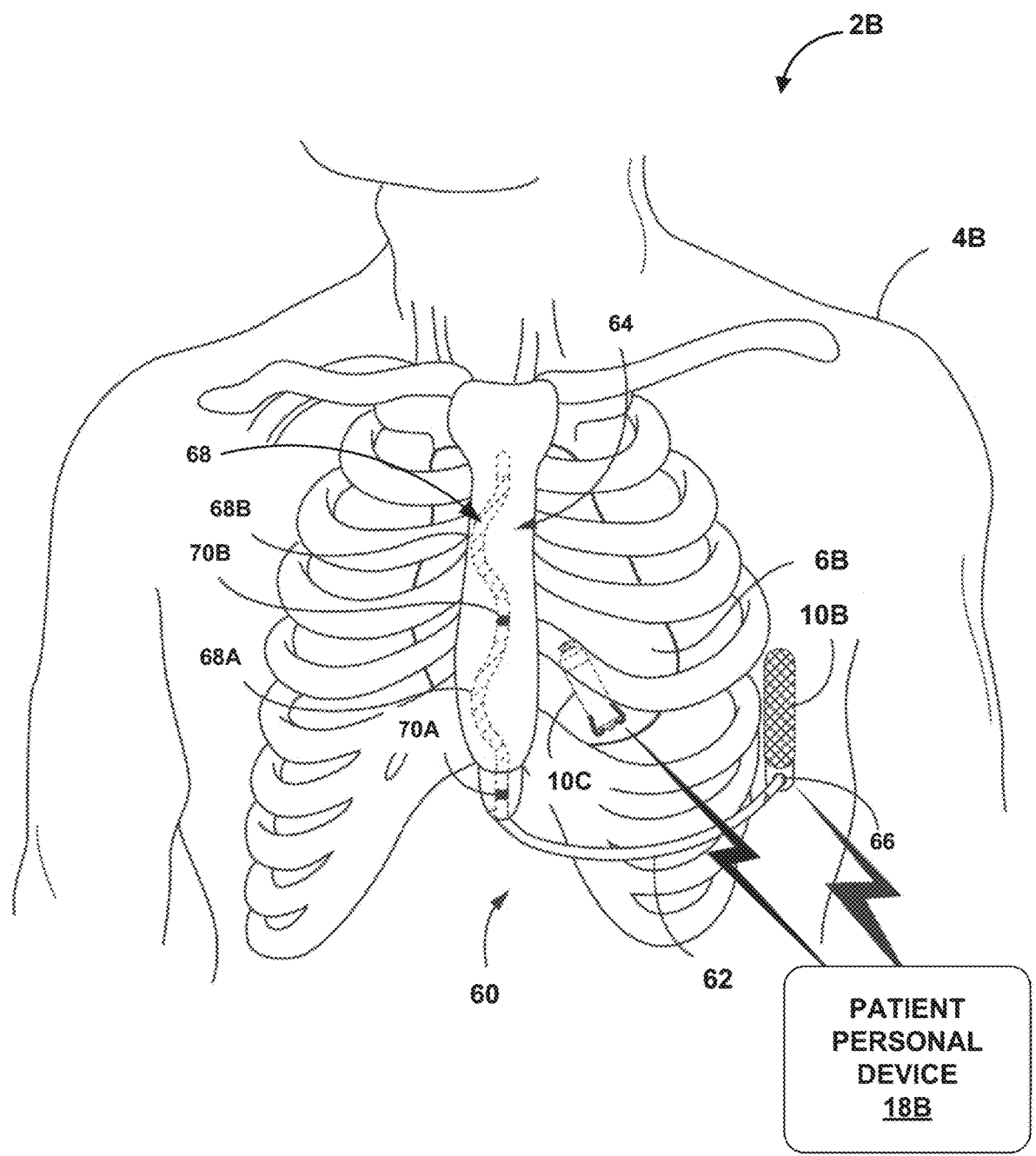
FIG. 3 is conceptual diagram illustrating another example of a medical device system including a leadless implantable medical device and the patient personal device of FIG. 1 in conjunction with a patient.
Figure 4:
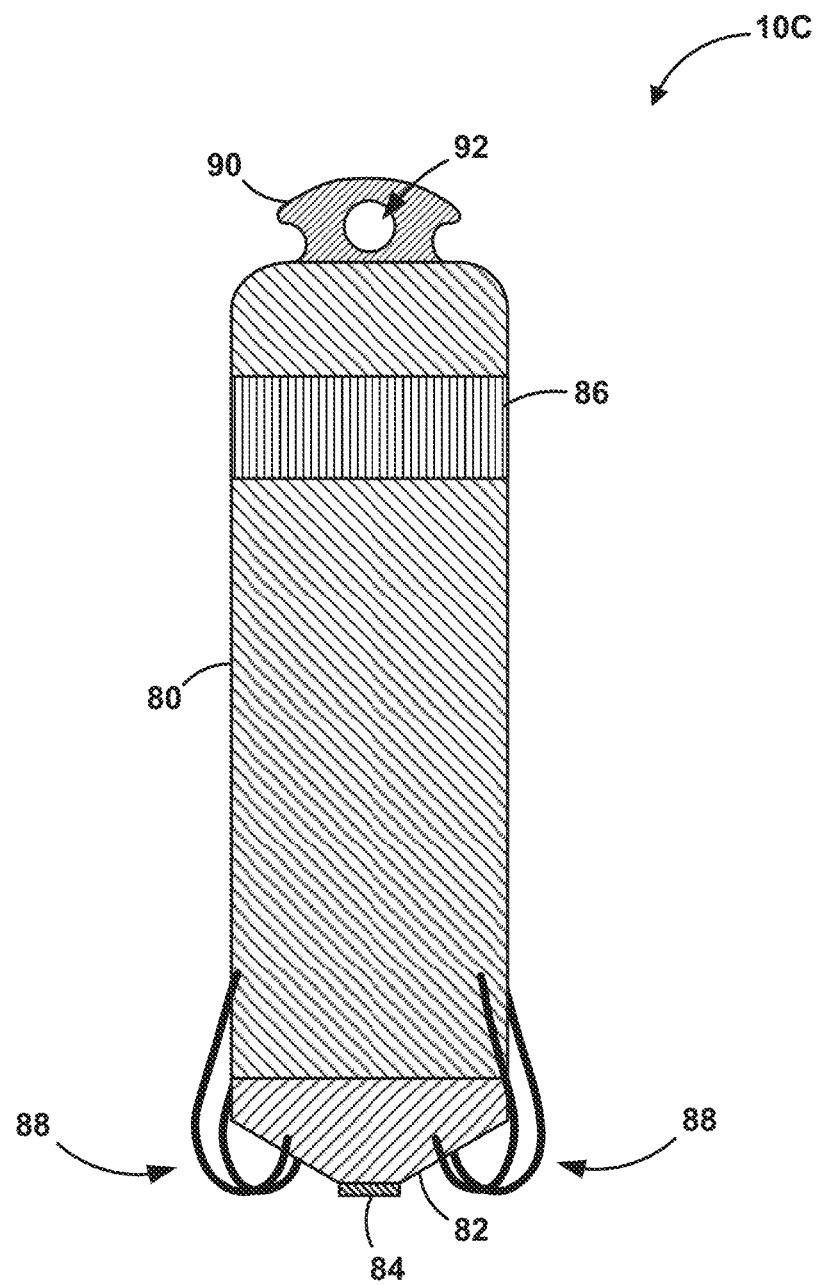
FIG. 4 is a conceptual drawing illustrating an example configuration of the leadless implantable medical device of the medical device system of FIG. 3.

FIGS. 3 and 4 illustrate components of example medical device system 2B, which includes an IMD 10B, a leadless IMD 10C, and patient personal device 18B. FIG. 3 illustrates the environment of system 2B in conjunction with patient 4B and heart 6B, in accordance with the example techniques described herein. FIG. 4 illustrates components of IMD 10C, which may be configured to deliver cardiac pacing to heart 6B. Medical device system 2B is another example of a medical device system configured to implement the techniques described herein for controlling one or more IMDs to deliver cardiac therapy (e.g., cardiac pacing or defibrillation) to a patient according to the techniques described above with respect to FIGS. 1 and 2. The techniques described as being carried out by system 2A of FIGS. 1 and 2 may be carried out in a substantially similar manner by system 2B. In addition, one or more features of system 2A may be substantially similar to the corresponding features of system 2B of FIGS. 3 and 4. For example, patient 4B, heart 6B, and patient personal device 18B may be substantially similar to patient 4A, heart 6A, and patient personal device 18A of FIGS. 1 and 2. However, as shown in FIG. 3, both IMD 10B and IMD 10C may be in wireless communication with patient personal device 18B, such that in some examples, patient 4B may enter a patient request, via an application running on patient personal device 18B, for the delivery of cardiac therapy by one or both of IMD 10B and IMD 10C.

As shown in FIG. 3, medical device system 2B includes an extracardiovascular IMD system 60 implanted within a patient 4B. IMD system 60 includes IMD 10B, which is an implantable cardiac defibrillator (ICD) and is referred to hereafter as ICD 10B. As shown in FIG. 3, ICD 10B may be connected to at least one implantable cardiac defibrillation lead 62. ICD 10B may be configured to deliver high-energy cardioversion or defibrillation pulses to heart 6B when atrial or ventricular fibrillation is detected. For example, ICD 10B may deliver cardioversion shocks in synchrony with a detected R-wave when fibrillation detection criteria are met. ICD 10B may deliver defibrillation shocks when fibrillation criteria are met, and the R-wave cannot be discerned from signals sensed by ICD 10B. In some examples, a patient request that patient 4B may enter into the application running on patient personal device 18B pertaining to ICD 10B may correspond to a requested value of a therapy parameter by which ICD 10B may deliver high-energy cardioversion or defibrillation pulses to heart 6B.

In some examples, ICD 10B may be implanted subcutaneously or submuscularly on the left side of patient 4B above the ribcage. Defibrillation lead 62 may be implanted at least partially in a substernal location. For example, at least a distal portion of defibrillation lead 62 may be implanted between sternum 64 and heart 6B. In one such configuration, a proximal portion of lead 62 extends subcutaneously from ICD 10B toward sternum 64 and a distal portion of lead 62 extends superior under or below the sternum 64 in an anterior mediastinum of patient 4B (not shown). The anterior mediastinum of patient 4B is bounded laterally by pleurae of patient 4B, posteriorly by a pericardium of patient 4B, and anteriorly by sternum 64. In some examples, the anterior wall of the anterior mediastinum may also be formed by the transversus thoracic and one or more costal cartilages. The anterior mediastinum includes a quantity of loose connective tissue (such as areolar tissue), some lymph vessels, lymph glands, substernal musculature (e.g., the transverse thoracis muscle), branches of the internal thoracic artery, and the internal thoracic vein. In one example, the distal portion of lead 62 extends along the posterior side of the sternum 64 substantially within the loose connective tissue and/or substernal musculature of the anterior mediastinum. Lead 62 may be at least partially implanted in other intrathoracic locations, e.g., other non-vascular, extra-pericardial locations, including the gap, tissue, or other anatomical features around the perimeter of and adjacent to, but not attached to, the pericardium or other portion of heart 6B, and not above the sternum 64 or a ribcage of patient 4B.

In other examples, lead 62 may be implanted at other extracardiovascular locations. For example, defibrillation lead 62 may be implanted such that it extends subcutaneously above the ribcage of patient 4B from ICD 10B toward a center of the torso of patient 4B, bend or turn near the center of the torso of patient 4B, and extend subcutaneously superior above the ribcage and/or sternum 64. Defibrillation lead 62 may be positioned to have one of several orientations. For example, defibrillation lead 62 may be offset laterally to the left or the right of the sternum 64 or located over the sternum 64. Defibrillation lead 62 may extend substantially parallel to the sternum 64 or be angled laterally from the sternum 64 at either the proximal or distal end.

Defibrillation lead 62 includes an insulative lead body having a proximal end that includes a connector 66 configured to be connected to ICD 10B and a distal portion that includes one or more electrodes. Defibrillation lead 62 also may include one or more conductors that form an electrically conductive path within the lead body of defibrillation lead 62 and interconnect the electrical connector and respective ones of the electrodes.

Defibrillation lead 62 includes a defibrillation electrode that includes two sections or segments 68A and 68B (individually or collectively, "defibrillation electrode[s] 68"). The defibrillation electrode 68 is toward the distal portion of defibrillation lead 62, e.g., toward the portion of defibrillation lead 62 extending along the sternum 64. In some examples, defibrillation lead 62 may be placed below and/or along sternum 64 such that a therapy vector between defibrillation electrodes 68A or 68B and a housing electrode formed by or on ICD 10B (or other second electrode of the therapy vector) is substantially across a ventricle of heart 6B. The therapy vector may, in one example, be viewed as a line that extends from a point on defibrillation electrode 68 (e.g., a center of one of the defibrillation electrode sections 68A or 68B) to a point on the housing electrode of ICD 10B. Defibrillation electrode 68 may, in one example, be an elongated coil electrode.

Defibrillation lead 62 may also include one or more sensing electrodes, such as sensing electrodes 70A and 70B (individually or collectively, "sensing electrode[s] 108"), located along the distal portion of defibrillation lead 62. In the example of FIG. 3, sensing electrodes 70A and 70B are separated from one another by defibrillation electrode 68A. In other examples, however, sensing electrodes 70A and 70B both may be distal of defibrillation electrode 68 or both may be proximal of defibrillation electrode 68. In other examples, lead 62 may include other configurations of electrodes at various locations proximal and/or distal to defibrillation electrode 68. In the same or different examples, ICD 10B may include one or more electrodes positioned on another lead (not shown).

IMD system 60 may sense electrical signals via one or more sensing vectors that include combinations of electrodes 70A and 70B and the housing electrode of ICD 10B. In some examples, ICD 10B may be configured to sense cardiac electrical signals using a sensing vector that includes one of the defibrillation electrode sections 68A and 68B and one of sensing electrodes 70A and 70B or the housing electrode of ICD 10B. The sensed electrical intrinsic signals may include electrical signals generated by cardiac muscle of heart 6B at various times during the cardiac cycle. ICD 10B may be configured to analyze the electrical signals sensed by the one or more sensing vectors to detect tachyarrhythmia, such as ventricular tachycardia or ventricular fibrillation. In response to detecting the tachyarrhythmia, ICD 10B may begin to charge a storage element, such as a bank of one or more capacitors, and, when charged, deliver one or more defibrillation pulses via defibrillation electrode 68 of defibrillation lead 62 if the tachyarrhythmia is still present.

Medical device system 2B also includes IMD 10C, which is implanted within heart 6B and configured to deliver cardiac pacing to the heart. In some examples, IMD 10C is an intracardiac pacing device (IPD) and may be referred to as IPD 10C hereafter. In the illustrated example, IPD 10C is implanted within the right ventricle of heart 6B. However, in other examples, system 2B may additionally or alternatively include one or more IPDs 10C within other chambers of heart 6B, or ay include similarly configured pacing devices attached to an external surface of heart 6B (e.g., in contact with the epicardium) such that a pacing device is disposed outside of heart 6B.

IPD 10C is configured to sense electrical activity of heart 6B and deliver pacing therapy, e.g., bradycardia pacing therapy, CRT, anti-tachycardia pacing (ATP) therapy, and/or post-shock pacing, to heart 6B. For example, IPD 10C may be configured to sense electrical signals received from one or more electrodes carried on the housing of IPD 10C. Such electrical signals may be electrical signals generated by cardiac muscle of heart 6B and indicative of depolarizations and repolarizations of heart 6B at various times during the cardiac cycle. IPD 10C may analyze the sensed electrical signals to detect bradycardia and tachyarrhythmias, such as ventricular tachycardia or ventricular fibrillation. In response to detecting bradycardia, IPD 10C may deliver bradycardia pacing via the electrodes of IPD 10C. In response to detecting tachyarrhythmia, IPD 10C may, depending on the type of tachyarrhythmia, deliver ATP therapy via the electrodes of IPD 10C. In some examples, IPD 10C may deliver post-shock pacing in response to determining that another medical device, e.g., ICD 10B, delivered an anti-tachyarrhythmia shock.

In any such examples, a patient request that patient 4B may enter into the application running on patient personal device 18B pertaining to IPD 10C may correspond a requested type of cardiac therapy that IPD 10C is configured to deliver. For example, such a patient request may correspond to a request that IPD 10C deliver one of bradycardia pacing therapy, CRT, ATP pacing therapy, and/or post-shock pacing therapy. In some such examples, the patient request also may include a requested value of a therapy parameter by which IPD 10C may deliver the requested therapy. For example, a patient request for IPD 10C to deliver bradycardia pacing therapy may include a request to deliver bradycardia pacing at a particular pulse rate. In other examples, the patient request may include the requested type of cardiac therapy and an indication of an activity level or activity of patient 4B. In such examples, IPD 10C may determine requested values of one or therapy parameters of the requested type of cardiac therapy based on one or more values of the therapy parameters stored in a memory of system 2B (e.g., a memory of IMD 10C, a memory of patient personal device 18B, and/or a server that is accessible by patient personal device 18B) in association with the activity level or activity of patient 4B. In still other examples, the patient request may include only the requested type of cardiac therapy. In such examples, one or more components of system 2B (e.g., of IPD 10C) may determine values of one or more physiological parameters of patient 4B, such as a heart rate and/or an activity level or activity, and may determine a default value of one or more therapy parameters of the requested type of cardiac therapy according to which IPD 10C may deliver the requested cardiac therapy.

As with the techniques described above with respect to system 2A of FIGS. 1 and 2, techniques by which ICD 10B or IPD 10C may deliver cardiac therapy in response to receiving a patient request entered by patient 4B into an application running on patient personal device 18B may include comparing a requested value of a therapy parameter to one or more allowable values of the therapy parameter and/or determining a weight value associated with the requested value of the therapy parameter. In some examples, such techniques also may include requesting feedback from patient 4B regarding the efficacy of delivered cardiac therapy and/or transmitting data pertaining to patient requests, symptoms, undesired effects, and/or efficacy indications to a remote computer, as described above with respect to system 2A.

In some examples, system 2B may include one or more additional sensors, such as one or more accelerometers (not shown). In some examples, the one or more accelerometers may comprise one or more three-axis accelerometers, and may be a component of ICD 10B, IPD 10C, and/or a component of another IMD of system 2B. Signals generated by such accelerometers may be indicative of, for example, gross body movement of patient 4B, such as a patient posture or activity level. Regardless of the configuration of such accelerometers, processing circuitry of system 2B may determine patient parameter values pertaining to patient posture or activity level based on the signals obtained therefrom, such as whether patient 4B's activity level is low, medium, high, associated with a numeric value, or associated with a particular activity or other value. Such processing circuitry may be contained within ICD 10B, IPD 10C, or within another IMD or other device of system 2B. As discussed above with respect to system 2A of FIGS. 1 and 2, such processing circuitry then may use the determined patient parameter values pertaining to posture and/or activity level to determine a default value of a therapy parameter, such as a value by which to deliver cardioversion or defibrillation pulses via ICD 10B or a rate at which to deliver cardiac pacing to heart 6B via IPD 10C. As described above with respect to IMD 10A of system 2A, ICD 10B and/or IPD 10C then may deliver cardiac therapy to heart 6B according to the determined patient parameter value, or may deliver cardiac therapy to heart 6B according to a requested value of the therapy parameter that the processing circuitry may determine based on a patient request received by the processing circuitry from an application running on patient personal device 18B. In some examples, the application may run on patient personal device 18B to enable patient 4B to interact with a medical device system (e.g., system 2B), and receipt of the request by the processing circuitry from the application indicates that the request was made by patient 4B.

In some examples, ICD 10B and IPD 10C may be configured to coordinate their arrhythmia detection and treatment activities. In other examples, ICD 10B and IPD 10C may be configured to operate completely independently of one another. In some such examples, ICD 10B and IPD 10C may not be configured to establish telemetry communication sessions with one another to exchange information about sensing and/or therapy using one-way or two-way communication. Instead, each of ICD 10B and IPD 10C may analyze the data sensed via their respective electrodes and/or accelerometers to detect tachyarrhythmia or fibrillation or make other therapy-related determinations. As such, each device may not know if the other will detect the tachyarrhythmia, if or when it will provide therapy, and the like. In some such examples, IPD 10C may be configured to detect anti-tachyarrhythmia shocks delivered by ICD system 2B, which may improve the coordination of therapy between subcutaneous ICD 10B and IPD 10C without requiring device-to-device communication. In this manner, IPD 10C may coordinate the delivery of cardiac stimulation therapy, including the termination of ATP and the initiation of the delivery of post-shock pacing, with the application of an anti-tachyarrhythmia shock merely through the detection of defibrillation pulses and without the need to communicate with the defibrillation device applying the anti-tachyarrhythmia shock.

In other examples, IPD 10C and ICD 10B may engage in communication to facilitate the appropriate detection of arrhythmias and/or delivery of therapy. The communication may include one-way communication in which one device is configured to transmit communication messages and the other device is configured to receive those messages. The communication may instead include two-way communication in which each device is configured to transmit and receive communication messages. Two-way communication and coordination of the delivery of patient therapies between IPD 10C and ICD 10B is described in commonly-assigned U.S. Pat. No. 8,744,572, titled, "SYSTEMS AND METHODS FOR LEADLESS PACING AND SHOCK THERAPY," Jun. 3, 2014, the entire content of which is incorporated by reference herein.

Although FIG. 3 is illustrated and described in the context of an example of IPD 10C and extracardiovascular IMD system 60 in which at least a distal portion of lead 62 is implanted substernally, techniques in accordance with one or more aspects of the present disclosure may be applicable to other example systems. For example, an extracardiovascular ICD system may include a lead having a distal portion that is implanted subcutaneously above the sternum (or other location) instead of being implanted substernally. As another example, instead of an IPD, a pacing system may be implanted having an IMD and one or more leads connected to and extending from the pacemaker into one or more chambers of the heart or attached to the outside of the heart to provide pacing therapy to the one or more chambers (e.g., system 2A of FIG. 1). In any such examples, the IMDs may be configured to receive patient requests from patient personal device 18B, as described above.

FIG. 4 is a conceptual drawing illustrating an example configuration of IPD 10C of FIG. 3. As illustrated in FIG. 4, IPD 10C may include case 80, cap 82, electrode 84, electrode 86, fixation mechanisms 88, flange 90, and opening 92. Together, case 80 and cap 82 may form a hermetically sealed housing of IPD 10C. For example, case 80 and cap 82 may enclose and protect electrical components (e.g., processing circuitry, sensing circuitry, therapy delivery circuitry, or other components) within IPD 10C. In some examples, case 80 may enclose some or all of the electrical components of IPD 10C, and cap 82 may seal case 80 and create the hermetically sealed housing of IPD 10C. IPD 10C may include one or more electrodes (e.g., electrodes 84 and 86) configured to deliver an electrical signal (e.g., therapy such as cardiac pacing) and/or to configured to provide at least one sensing vector.

Electrodes 84 and 86 are carried on the housing created by case 80 and cap 82. In this manner, electrodes 84 and 86 may be considered leadless electrodes. In the example of FIG. 4, electrode 84 is disposed on the exterior surface of cap 82. Electrode 84 may be a circular electrode positioned to contact cardiac tissue upon implantation. Electrode 86 may be a ring or cylindrical electrode disposed on the exterior surface of case 80. Both case 80 and cap 82 may be electrically insulating. In some examples, electrode 84 may be used as a cathode and electrode 86 may be used as an anode, or vice versa, for delivering cardiac pacing such as bradycardia pacing, CRT, ATP, or post-shock pacing. However, electrodes 84 and 86 may be used in any stimulation configuration. In addition, electrodes 84 and 86 may be used to detect intrinsic electrical signals from cardiac muscle, such as an electrocardiogram signal that processing circuitry of IPD 10C may receive via sensing circuitry of IPD 10C.

Fixation mechanisms 88 may be configured to attach IPD 10C to cardiac tissue and retain electrode 84 in contact with cardiac tissue. Fixation mechanisms 88 may be active fixation tines, screws, clamps, adhesive members, or any other mechanisms for attaching a device to tissue. In some examples, fixation mechanisms 88 may be constructed of a memory material, such as a shape memory alloy (e.g., nickel titanium), that retains a preformed shape. During implantation, fixation mechanisms 88 may be flexed forward to pierce tissue and allowed to flex back towards case 80. In this manner, fixation mechanisms 88 may be embedded within the target tissue.

Flange 90 may be provided on one end of case 80 to enable tethering or extraction of IPD 10C. For example, a suture or other device may be inserted around flange 90 and/or through opening 92 and attached to tissue. In this manner, flange 90 may provide a secondary attachment structure to tether or retain IPD 10C within heart 6B as a backup attachment to fixation mechanisms 88. Flange 90 and/or opening 92 may also be used to extract IPD 10C once the IPD needs to be explanted (or removed) from patient 4B if such action is deemed necessary.

In some examples, IPD 10C may also include one or more leads or electrode-bearing extensions configured to place one or more additional electrodes at another location within the heart 6B, which may be within the same or a different chamber of heart 6B than case 80. In some such examples, case 80 and cap 82 may carry fewer than all of the electrodes used to perform functions described herein with respect to IPD 10C. In other examples, each electrode of IPD 10C may be carried by one or more leads (e.g., the housing of IPD 10C may not carry any of the electrodes). In still other examples, IPD 10C or another pacing device used with system 2B may include or be coupled to three or more electrodes, where each electrode may be configured to deliver therapy and/or sense electrical signals of heart 6B.

Figure 5:
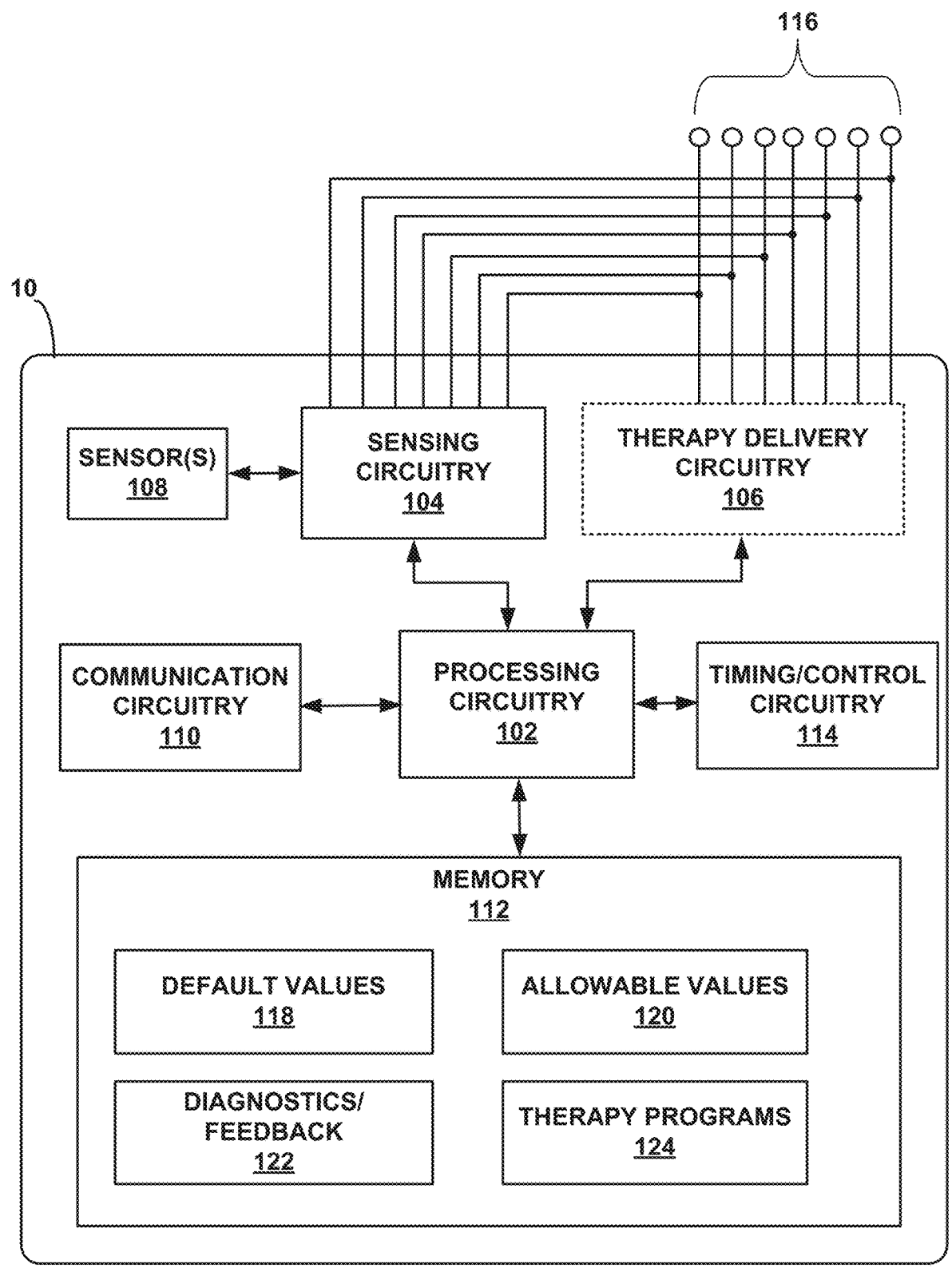
FIG. 5 is a functional block diagram illustrating an example configuration of an example implantable medical device.

FIG. 5 is a functional block diagram illustrating an example configuration of an IMD 10. In some examples, one or more components of IMD 10 may be substantially similar to one or more corresponding components of any of IMD 10A of FIGS. 1 and 2, ICD 10B of FIG. 3, or IPD 10C of FIGS. 3 and 4, and may be used to perform the techniques of FIGS. 1-4. As shown in FIG. 5, IMD 10 includes processing circuitry 102, sensing circuitry 104, therapy delivery circuitry 106, sensors 108, communication circuitry 110, and memory 112. In addition, IMD 10 includes one or more electrodes 116, which may be any one or more of the previously-described electrodes of IMD 10A, ICD 10B, or IPD 10C, and one or more of which may be disposed within housing a of IMD 10 or carried by a lead connected to IMD 10. In some examples, memory 112 includes computer-readable instructions that, when executed by processing circuitry 102, cause IMD 10 and processing circuitry 102 to perform various functions attributed to IMD 10 and processing circuitry 102 herein. Memory 112 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 102 may include fixed function circuitry and/or programmable processing circuitry. Processing circuitry 102 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 102 may include multiple components, such as any combination of one or more microprocessors, one or more controllers, one or more DSPs, one or more ASICs, or one or more FPGAs, as well as other discrete or integrated logic circuitry. The functions attributed to processing circuitry 102 herein may be embodied as software, firmware, hardware or any combination thereof.

In some examples, processing circuitry 102 may monitor the passage of time to determine when a period has elapsed, such as a period during which IMD 10 may deliver cardiac pacing according to a requested value of a therapy parameter or a period during which IMD 10 collects data pertaining to patient requests and/or efficacy indications, such as according to the techniques described above with respect to FIGS. 1-4. Processing circuitry 102 also may control IMD 10 to return to delivering cardiac pacing according to a default value of a therapy parameter or transmit data pertaining to patient requests and/or efficacy indications to a remote computer, at the conclusion of a corresponding period. In some such examples, processing circuitry 102 may control IMD 10 to return to delivering cardiac pacing according to the default value of the therapy parameter by gradually increasing or decreasing a value of a therapy parameter according to which IMD 10 is delivering cardiac pacing when transitioning between the requested value and the default value (e.g., "ramping up" or "ramping down" the value of the therapy parameter), which may provide a transition between the requested value of the therapy parameter and the default value of the therapy parameter that may reduce an extent to which patient 4 perceives the return to the default value, relative to a more abrupt transition between the requested value and the default value.

In some examples, processing circuitry 102 may be configured to associate determined values of one or more physiological parameters of patient 4A or 4B (generally, "patient 4"), such as a heart rate and/or an activity level or activity, with a particular time of day, such as day time or night time, so as to enable processing circuitry 102 to take into account a circadian rhythm of patient 4 when determining a default value of a therapy parameter. For example, a heart rate of patient 4 generally may decrease when patient 4 is asleep (e.g., nighttime), and increase when patient 4 is awake (e.g., daytime). Thus, IMD 10 may be configured to determine different (e.g., lower) default values for a particular parameter, such as a heart rate according to which IMD 10 may deliver cardiac pacing, at times when patient 4 is likely to be asleep than when patient 4 is likely to be awake. In examples in which IMD 10 includes one or more accelerometers, processing circuitry 102 may cross-reference a time of day indicated by timing and control circuitry with accelerometer data, such as to confirm whether patient 4 is asleep or awake as predicted based on the time of day. In some such examples, processing circuitry 102 may disregard the circadian rhythm of patient 4 if the time of day and the activity level or activity of patient 4 are incongruent, such as in the case of accelerometer data that indicates that patient 4 may be undertaking an activity level typically undertaken when patient 4 is awake, such as running or swimming, during a time when patient 4 typically is asleep. In this manner, processing circuitry 102 may enhance the ability of IMD 10 to accurately determine an appropriate default value of a therapy parameter according to which IMD 10 may deliver cardiac pacing, or to which IMD 10 may compare a requested value of the therapy parameter to determine a weight value.

As illustrated in FIG. 5, memory 112 may include one or more of default values 118, allowable values 120, diagnostics/feedback data 122, and/or therapy programs 124. As described above, in some examples, processing circuitry 102 of IMD 10 may be configured to determine a default value of a therapy parameter, which may be a therapy parameter that is a subject of a patient request. Processing circuitry 102 may determine the default value based a heart rate of patient 4 and/or an activity level or activity of patient 4, which then may be stored in default values 118. In some examples, processing circuitry 102 may transmit one or more of default values 118 to a remote computer when processing circuitry 102 transmits data pertaining to one or more aspects of patient requests and/or efficacy indications to the remote computer. For example, default values 118 may provide a clinician with context for determining an extent to which requested values of a therapy parameter may be similar or dissimilar to default values 118, which may further help the clinician determine whether allowable values 120 remain appropriate for patient 4.

Allowable values 120 of memory 112 include one or more allowable values of one or more therapy parameters against which processing circuitry 102 may compare a requested value of the therapy parameter to determine whether to cause IMD 10 to deliver cardiac pacing according to the requested value. As discussed above, in examples in which processing circuitry 102 determines that a requested value is not among allowable values 120, processing circuitry 102 may determine a difference between the requested value and one of allowable values 120, such as a nearest one of allowable values 120 that is closest in value to the requested value. If the difference between the requested value and the nearest one of allowable values 120 does not satisfy a difference threshold, processing circuitry 102 may cause IMD 10 to deliver cardiac pacing according to the nearest allowable value, and in some examples may cause patient personal device 18 to display a request for patient 4 to confirm delivery of cardiac pacing according to the nearest allowable value.

A clinician may enter allowable values 120 into memory 112 around the time of implantation of IMD 10, such as via a clinician programming device that is separate from the patient personal device 18. The clinician may update allowable values 120 periodically or on an as-needed basis. For example, the clinician may determine that allowable values 120 are no longer appropriate for patient 4 if a health condition of patient 4 has changed since the clinician entered allowable values 120 into memory 112, or if patient 4's pacing needs otherwise have changed. In some such examples, the clinician may enter one or more updated allowable values 120 of one or more therapy parameters into a remote computer, such as based on the indication of the efficacy of cardiac pacing. Processing circuitry 102 then may receive the updated allowable values 120 from the remote computer, and may store updated allowable values 120 in memory 112.

Diagnostics/feedback 122 of memory 112 may include data pertaining to one or more of patient requests, patient indications of symptoms or undesired effects, or the efficacy of cardiac pacing delivered by IMD 10. For example, diagnostics/feedback 122 may store one or more aspects of patient requests entered by patient 4 into the application, such as requested values, requested durations, and/or associated default values. In some examples, diagnostics/feedback 122 also may store efficacy determinations, which may include an indication of a perceived efficacy of cardiac pacing entered by patient 4 into the application running on patient personal device 18, such as in response to a request for feedback from the application. Diagnostics/feedback 122 also may store efficacy determinations made by processing circuitry 102 based on data pertaining to symptoms or undesired effects experienced by patient 4 before, during, and/or after delivery of cardiac pacing by IMD 10. In some examples, diagnostics/feedback 122 may store system diagnostics pertaining to the functioning of IMD 10 or other components of a medical device system including IMD 10.

Therapy programs 124 may include values of one or more therapy parameters, and each of therapy programs 124 may correspond to a patient activity level or activity. For example, one of therapy programs 124 may correspond to a patient activity level "high," and another one of therapy programs 124 may correspond to a patient activity "bicycling." In either example, the therapy program may include values of one or more therapy parameters that may be appropriate for the activity level or activity. The values of the one or more therapy parameters that may be appropriate for the activity level or activity corresponding to one of therapy programs 124 may be selected by a clinician at or around the time of implant of IMD 10, and may be updated periodically in a manner similar to the manner in which the clinician may update allowable values 120. In some examples, a patient request may include a request to deliver cardiac pacing according to a selected one of therapy programs 124, such as a "bicycling" program. Upon receiving the request, processing circuitry 102 may cause therapy delivery circuitry 106 to deliver cardiac pacing for a duration of time, such as a duration of a period of time associated with the selected one of therapy programs 124 or a duration of time requested by patient 4. In some examples, receipt of the request by processing circuitry 102 from the application indicates that the request was made by patient 4 via patient personal device 18. For example, receipt of the request by processing circuitry 102 may enable network technology and functionality to validate the patient request, transmitted from a device purporting to be patient personal device 18 and directed toward IMD 10, by confirming the identity of the device purporting to be patient personal device 18.

In some examples, processing circuitry 102 may compare the values of the one or more therapy parameters associated with one of programs 124 selected by patient 4 in a patient request to default values of the one or more therapy parameters, as discussed above. Processing circuitry 102 further may determine a weight value based on one or more of the differences between the values of the one or more therapy parameters associated with the selected one of programs 124 and the one or more default values, which may influence the duration of the period of time for which processing circuitry 102 therapy delivery circuitry to deliver cardiac pacing according to the selected one of therapy programs 124. For example, if processing circuitry 102 determines that one or more of the differences satisfies a corresponding difference threshold, processing circuitry 102 may determine a weight value corresponding to a period of time that is longer than a period of time associated with a weight value that corresponds to a difference between a default value of the therapy parameter and the values of the one or more therapy parameters associated with the selected one of programs 124 that does satisfy a difference threshold.

In some examples, different ones of therapy programs 124 may be associated with difference thresholds having different values. In such examples, a difference threshold associated with one of therapy programs 124 may be selected based on an expected difference between one or more default values that processing circuitry 102 may determine when patient 4 is undertaking an activity associated with the program, and the values of the one or more therapy parameters associated with the program. For example, an expected difference between one or more default values that processing circuitry 102 may determine when patient 4 is bicycling may be significantly different than the values of one or more therapy parameters associated with one of therapy programs 124 corresponding to bicycling. Thus, a difference threshold associated with the one of therapy programs 124 corresponding to bicycling, or any other activity expected to result in such a significant difference, may be greater than a difference threshold associated with one or more of therapy programs 124 corresponding to activities expected not to result in such a significant difference. In this manner, processing circuitry 102 may take into account a particular activity of patient 4 when determining a weight value based on a determined difference between one or more default values and values of one or more therapy parameters associated with one of therapy programs 124, and thus may cause therapy delivery circuitry 106 to provide cardiac pacing appropriate for an activity undertaken by patient 4.

Sensing circuitry 104 and therapy delivery circuitry 106 may be selectively coupled to electrodes 116, e.g., via switching circuitry (not shown) as controlled by processing circuitry 102. The switching circuitry may include one or more transistors or other circuitry for selectively coupling electrodes 116 to other circuitry of IMD 10. Sensing circuitry 104 may monitor signals from electrodes 116 in order to monitor electrical activity of heart (e.g., to detect depolarizations for heart rate determination and/or to produce a cardiac electrogram for morphological or other analyses). Sensing circuitry 104 (or therapy delivery circuitry 106 may also generate a signal via electrodes 116, from which sensing circuitry 104 may produce a thoracic impedance signal, from which sensing circuitry 104 and/or processing circuitry 102 may sense respiration, e.g., magnitude and/or rate. Sensing circuitry 104 may also monitor signals from one or more other sensor(s) 108, such as one or more accelerometers (e.g., to determine an activity level or activity of patient 4). Sensing circuitry 104 may monitor signals from any electrodes or other sensors that may be positioned on IMD 10 or on another device in communication with IMD 10. In some examples, sensing circuitry 104 may include one or more filters and amplifiers for filtering and amplifying signals received from one or more of electrodes 116 and/or the one or more sensor(s) 108. Sensing circuitry 104 may also include rectification circuitry, sample-and-hold circuitry, one or more comparators, and/or analog-to-digital conversion circuitry. The functionality provided by such circuitry may be applied to the signal in the analog or digital domain.

Based on the signals, or indications or values determined from the signals, received from sensing circuitry 104, processing circuitry 102 may determine current values of a heart rate and/or an activity level or activity of patient 4. In some examples, processing circuitry 102 may determine the activity level or activity of patient 4 based on signals received from sensing circuitry 104 that may be indicative of one or more physiological parameters, such as signals indicative of movement received from one or more accelerometers. In some examples, processing circuitry 102 additionally may determine the activity level or activity of patient 4 based on a thoracic impedance signal received from sensing circuitry 104, which may be indicative of respiration, e.g., a magnitude (or depth) and/or rate indicative of respiration of patient 4. Processing circuitry 102 then may compare one or more requested values of one or more therapy parameters that processing circuitry 102 may determine based on a patient request, determine that the one or more requested values are one or more of allowable values 120, and control therapy delivery circuitry 106 to deliver cardiac pacing to patient 4 according to the one or more requested values for a period of time. In some examples, processing circuitry 102 also may determine one or more default values of the one or more therapy parameters, determine whether differences between the one or more default values and the one or more requested values satisfies one or more corresponding thresholds stored in therapy programs 124 and/or default values 118, and determine a weight value based on the differences. Processing circuitry 102 then may control therapy delivery circuitry 106 to deliver cardiac pacing to patient 4 according to the one or more requested values and the weight value, for a period of time that processing circuitry 102 may determine at least partially based on the weight value. Therapy delivery circuitry 106 may include circuitry for generating a signal, such as one or more capacitors, charge pumps, and/or current sources, as well as circuitry for selectively coupling the signal to electrodes 116, e.g., transistors or other switching circuitry.

Communication circuitry 110 may include any suitable hardware, firmware, software or any combination thereof for communicating with another device, such as patient personal device 18A or patient personal device 18B (generally, "patient personal device 18), or another IMD or sensor, such as a pressure sensing device. For example, communication circuitry 110 may include voltage regulators, current generators, oscillators, or circuitry for generating a signal, resistors, capacitors, inductors, and other filtering circuitry for processing received signal, as well as circuitry for modulating and/or demodulating a signal according to a communication protocol. Communication circuitry 110 may also include transistors or other switching circuitry for selectively coupling transmitted signal to or receiving signals from antenna 124 or electrodes 116 (e.g., in the case of tissue conductance communication (TCC)). Under the control of processing circuitry 102, communication circuitry 110 may receive downlink telemetry from, as well as send uplink telemetry to, patient personal device 18 or another device. In some examples, communication circuitry 110 may communicate with patient personal device 18. In addition, communication circuitry 110 may communicate with a networked computing device via an external device (e.g., patient personal device 18) and a computer network, such as the Medtronic CareLink® Network developed by Medtronic, plc, of Dublin, Ireland, as further described below with respect to FIG. 7.

Patient 4, a clinician, or another user may retrieve data from IMD 10 using patient personal device 18, or by using another local or networked computing device (e.g., a remote computer located with the clinician) configured to communicate with processing circuitry 102 via communication circuitry 110. In some examples, the clinician may also program parameters of IMD 10 using patient personal device 18 or another local or networked computing device. For example, the clinician may update default values 118, allowable values 120, and/or values associated with therapy programs 124.

Although processing circuitry 102 of IMD 10 is described above as being configured to receive signals from sensors 108, determine values of physiological parameters of patient 4, compare a requested value of a therapy parameter to allowable values 120, determine default values 118, compare a requested value to default values, determine weight values, and carry out other steps of the techniques described herein, any steps described herein as being carried out by processing circuitry 102 of IMD 10 may carried out by processing circuitry of one or more other devices. For example, processing circuitry of patient personal deice 18, a remote computer, or any other suitable implantable or external device or server, may be configured to carry out one or more of the steps of the techniques described herein, such as via communication circuitry of 110 IMD 10.

Figure 6:
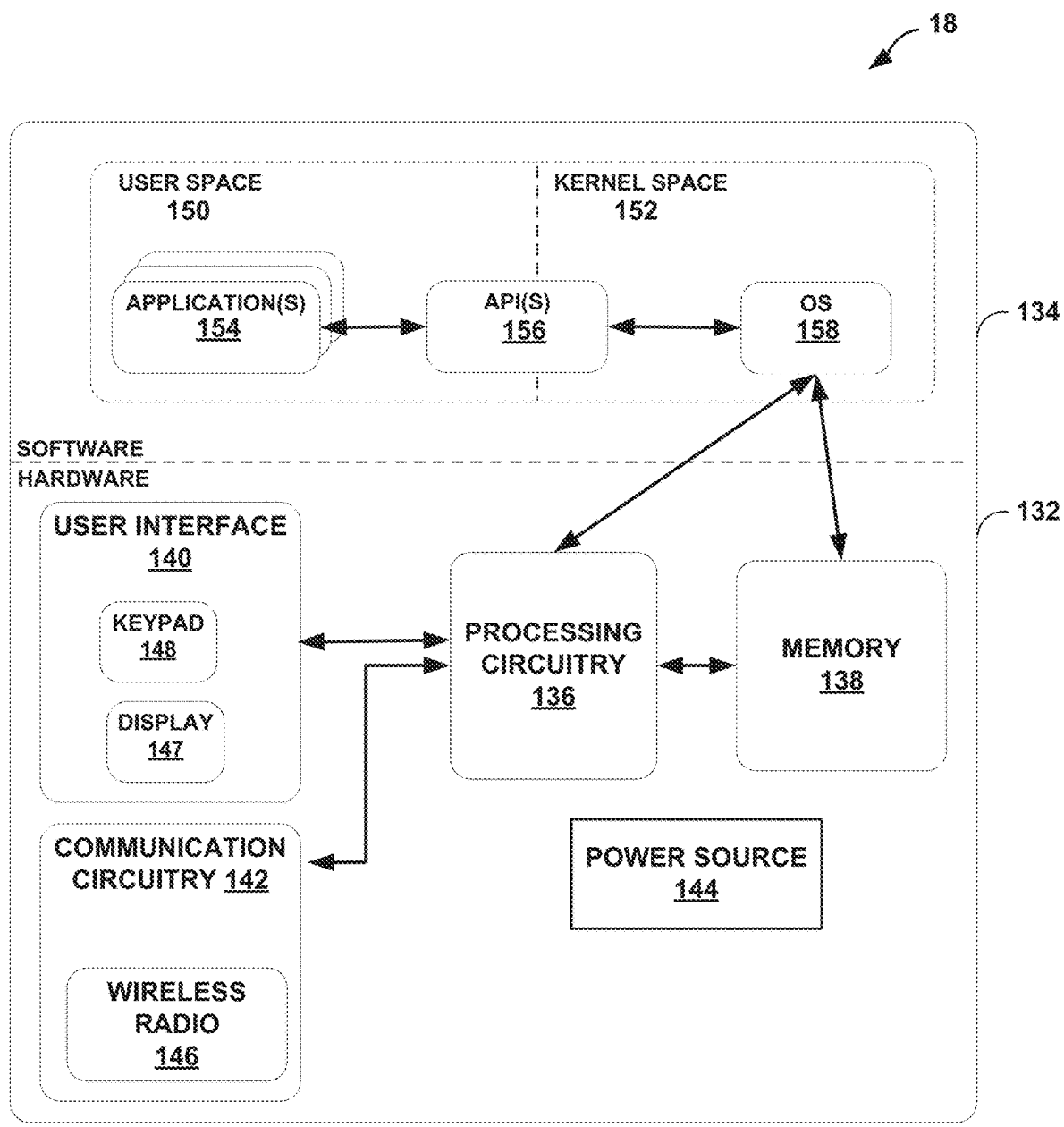
FIG. 6 is a functional block diagram illustrating an example configuration of an example patient personal device.

FIG. 6 is a functional block diagram illustrating an example configuration of a patient personal device, such as patient personal device 18 described with respect to FIG. 5 as being either of patient personal device 18A of FIG. 1 or patient personal device 18B of FIG. 3. FIG. 6 is described in the context of IMD 10 of FIG. 5, one or more components of which may be substantially similar to one or more corresponding components of any of IMD 10A of FIGS. 1 and 2, ICD 10B of FIG. 3, or IPD 10C of FIGS. 3 and 4.

Patient personal device 18 may be a smartphone, tablet, laptop computer, or other consumer device configured to run applications. As shown in the example of FIG. 6, patient personal device 18 may include a hardware environment 132 and a software environment 134. However, in some examples, one or more features of hardware environment 132 may be implemented as software. Further, in some examples, one or more features of software environment 134 may be implemented as hardware.

In the example of FIG. 6, hardware environment 132 includes processing circuitry 136, memory 138, user interface 140, communication circuitry 142, and power source 144 A patient (e.g., patient 4), a clinician, or another user may interact with processing circuitry 136 via a user interface 140, which may include display 147 and, optionally, keypad 148. In other examples, patient 4 or a clinician may interact with processing circuitry 136 to retrieve information from IMD 10, program a monitoring function of processing circuitry 136 or IMD 10, or for other reasons not expressly describe herein. Further, processing circuitry 136 may establish a wireless connection with IMD 10 via wireless radio 146 of communication circuitry 142. Processing circuitry 136 may generate information regarding the wireless connection for presentation to patient 4, a clinician, or other user via user interface 140. Processing circuitry 136 may include one or more microprocessors, digital signal processors (DSPs), application specific integrated circuits (ASICs), field programmable gate arrays (FPGAs), or any other equivalent integrated or discrete logic circuitry, as well as any combinations of such components.

Patient 4 may interact with user interface 140 by speaking, gesturing, touching user interface 140, using pointing device such as a stylus, mouse, or other such device, or in any other suitable manner. In some examples, patient 4 may interact with user interface 140 to enter information into an application running on device 18, as described above with respect to FIGS. 1-5. For example, patient 4 may interact with user interface 140 to enter a patient request, enter an indication symptoms or undesired effects experienced by patient 4, and/or enter a perceived efficacy of cardiac pacing. In other examples, patient 4 may interact with user interface 140 to view, via display 147 a request for feedback, view an indication that IMD 10 may not deliver cardiac pacing according to a requested value that is not one of allowable values 120, view medical instructions from a clinician, view information pertaining to patient 4's health and/or treatment, or view other information.

Patient personal device 18 also includes a memory 138. Memory 138 may include program instructions that, when executed by processing circuitry 136, cause patient personal device 18 to perform the functions ascribed to patient personal device 18 herein, such as transmitting a patient request to processing circuitry 102 of IMD 10 and/or a remote computer, or receiving data from IMD 10 and/or the remote computer. In some examples, memory 138 may be random access memory (RAM), read only memory (ROM), programmable read only memory (PROM), erasable programmable read only memory (EPROM), electronically erasable programmable read only memory (EEPROM), or flash memory comprising executable instructions for causing the one or more processors to perform the actions attributed to them. Further, memory 138 may be implanted entirely in hardware, software, or a combination thereof.

Processing circuitry 136 and memory 138 provide an operating environment for a software stack (e.g., software environment 134) that executes one or more application(s) 158 for controlling therapy of IMD 10A. Patient personal device 18 partitions the virtual and/or physical address space provided by memory 138 into user space 150, allocated for running user processes, and kernel space 152, which is protected and generally inaccessible by user processes. Operating system kernel 152 executes in kernel space 152 and may include, for example, an Android operating system kernel available from Google, Inc., an iOS operating system kernel available from Apple, Inc., a Windows-based operating system kernel, available from Microsoft Corp., or a Linux- or another Unix-variant-based kernel.

In one example, applications 154 execute in user space 150 to communicate with IMD 10A. Applications 154 may invoke one or more Application Programming Interfaces (APIs) 156 to communicate with operating system 158. APIs 156 may execute in user space 150, kernel space 152, or a combination of kernel space 152 and user space 150. For example, applications 154 may invoke a wireless communication API of APIs 156 to establish a wireless communication session with an IMD 10, which may be one or more of IMD 10A of FIGS. 1 and 2, ICD 10B of FIG. 3, and IPD 10C of FIGS. 3 and 4. In some examples, the wireless communication API of APIs 156 is a Blueooth® or BLE API. The wireless communication API of APIs 156 may provide a library of functions that, when used, cause operating system 158 to control communication circuitry 142 and wireless radio 146 of hardware environment 132 to establish the wireless communication session with IMD 10.

In some examples, operating system 158 is a version of Android OS and API 156 is a Blueooth® or BLE API. Further description regarding the implementation of the Bluetooth® protocol in Android OS is provided in Bluetooth, Android Developers, available at https://developer.android-.com/guide/topics/connectivity/bluetooth.html (retrieved May 30, 2018), the entire content of which is incorporated herein by reference. Further description regarding the implementation of the BLE protocol in Android OS is provided in Bluetooth Low Energy, Android Developers, available at https://developer.android.com/guide/topics/connectivity/bluetooth-le.html (retrieved May 30, 2018), the entire content of which is incorporated herein by reference.

In some examples, operating system 158 is a version of Apple iOS and API 156 is a Blueooth® or BLE API. Further description regarding the implementation of the Bluetooth protocol in Apple iOS is provided in About Core Bluetooth, Apple Inc., available at https://developer.apple.com/library/content/documentation/NetworkingInternetWeb/Conceptual/CoreBluetooth_concepts/AboutCoreBluetooth/Introduction.html#//apple_ref/doc/uid/TP40013257 (retrieved May 30, 2018), the entire content of which is incorporated herein by reference. Further description regarding the implementation of the BLE protocol in Apple iOS is provided in Core Bluetooth, Apple Developer Documentation, Apple Inc., available at https://developer.apple.com/documentation/corebluetooth (retrieved May 30, 2018), the entire content of which is incorporated herein by reference.

In some examples, communication circuitry 142 and wireless radio 146 may be configured to receive, from IMD 10, an advertisement indicating an availability of IMD 10 for a wireless connection. In response to receiving the advertisement, operating system 158 creates an object handle that API 156 passes to application 154. The object handle is an abstraction of IMD 10 that application 154 may use to establish a wireless connection. The object handle may be a constant that application 154 may use across multiple periods of time wherein IMD 10 is discoverable and periods of time wherein IMD 10 is non-discoverable.

Operating system 158 receives the advertisement, creates the object handle for IMD 10, and passes the object handle to application 154 via APIs 156. Upon establishing the wireless connection, patient 4 may use application 154 to accomplish one or more of submitting a patient request, entering information pertaining to symptoms, undesired effects, or efficacy of cardiac pacing, responding to a request for feedback, and/or receiving medical instructions.

Patient 4 may use application 154 to enter a patient request, via user interface 140, which may be associated with one or more requested values of one or more therapy parameters, in accordance with the techniques described with respect to FIGS. 1-5. For example, patient 4 may enter a request for a desired heart rate (e.g., a numeric value in beats per minute) into a GUI generated by patient personal device 18 via application 154, which patient 4 may find adequate for an activity that patient 4 plans to undertake or is currently undertaking. In other examples, a patient request entered by patient 4 may indirectly specify a desired heart rate by indicating that patient 4 plans to undertake or is currently undertaking a particular activity level (e.g., low, medium, high) or a particular activity (e.g., walking, swimming, bicycling, running, or sitting in a vehicle traveling on a bumpy road). In the case of an indirect patient request for a desired heart rate, processing circuitry of IMD 10 may determine a requested value of the heart rate based on a value stored in memory 112 (e.g., in therapy programs 124 of memory 112) that may correspond to the activity level or activity. In any such examples, processing circuitry 136 may receive the patient request via APIs 156 and OS 158, and transmit the request to communication circuitry 110 of IMD 10 via wireless radio 146 of communication circuitry 142 of patient personal device 18.

In some examples, patient 4 may use application 154 to enter, via user interface 140, information pertaining to one or more of symptoms or undesired effects experienced by patient, or to enter information pertaining to a perceived efficacy of cardiac pacing delivered by IMD 10, according to the techniques described above with respect to FIGS. 1-5. For example, patient 4 may enter a symptom or undesired effect experienced by patient 4 before, during, and/or after receiving cardiac pacing from IMD 10 according to a default value of a therapy parameter or a value of a therapy parameter associated with a patient request. In some such examples, patient 4 also may enter a severity of a symptom or undesired effect experienced before, during, and/or after delivery of cardiac pacing by IMD 10 according to the default value or the value associated with the patient request. Additionally, or alternatively, patient 4 may enter a perceived efficacy of the delivery of cardiac pacing by IMD 10 during or after the delivery thereof. In some examples, patient 4 may enter information pertaining to symptoms, undesired effects, or efficacy of cardiac therapy of his or her own accord. In other examples, user interface 140 may displayed, based on instructions from application 154 executed by patient personal device 18, a query or prompt for patient 4 to enter information pertaining to symptoms, undesired effects, or feedback pertaining to the efficacy of cardiac therapy. In such examples, patient 4 may enter such information in response to the query or prompt.

In any such examples, processing circuitry 136 may receive the information entered by patient 4 via APIs 156 and OS 158, and transmit the information to communication circuitry 110 of IMD 10 via wireless radio 146 of communication circuitry 142 of patient personal device 18. In some examples, processing circuitry 102 of IMD 10 may cause communication circuitry 110 of IMD 10 to transmit data pertaining to the information entered by patient 4 into user interface 140 to a remote computer. A clinician may receive the information entered by patient 4 into user interface 140 via the remote computer, and may make one or more determinations pertaining to the operation of IMD 10 based on the information, such as a determination of whether allowable values 120 of a therapy parameter stored in memory 112 of IMD 10 remain appropriate for patient 4.

In some examples, patient 4 may use application 154 to receive medical instructions, via user interface 140, which a clinician may enter into a remote computer for transmission to patient personal device 18, in accordance with the techniques described with respect to FIGS. 1-5. For example, the clinician may determine, based on one or more of patient requests, symptoms, undesired effects, and/or perceived efficacy of cardiac pacing entered by patient 4 inter user interface 140 of application 154 or determined by processing circuitry 102 of IMD 10, that patient 4 may require additional medical attention. In response to determining that patient 4 may require additional medical attention, the clinician may transmit, via the remote computer, medical instructions to patient personal device 18. Such medical instructions may include instruction for patient 4 to schedule a visit with the clinician or for patient 4 to seek other medical attention. In any such examples, processing circuitry 136 may receive the medical instructions from the remote computer via wireless radio 146 of communication circuitry 142 of patient personal device 18, and cause user interface 140 to display the medical instructions via application 154.

Accordingly, such techniques as disclosed herein may enabling patient 4A to provide input to IMD 10 via application 154 may provide one or more benefits, such as one or more of improved efficacy of cardiac pacing provided by IMD 10, reduced burden on a clinician's time, or increased engagement of patient 4 in his or her medical treatment, one or more of which may help improve clinical outcomes and/or reduce healthcare expenses. In addition, patient 4's pre-existing familiarity with patient personal device 18, and/or patient 4's likely pre-existing inclination to use patient personal device 18 for various tasks, may make patient 4A more likely to provide input to IMD 10 via application 154 running on patient personal device 18 relative to, for example, a separate programmer for IMD 10. In turn, patient 4 may be more likely to obtain improved clinical outcomes that may result from consistently providing such input to IMD 10 such as a reduction in symptoms and undesired effects and/or an increase in ability to participate in and enjoy activities, than other examples in which a patient may be given a separate programmer with which to provide input to an IMD.

Figure 7:
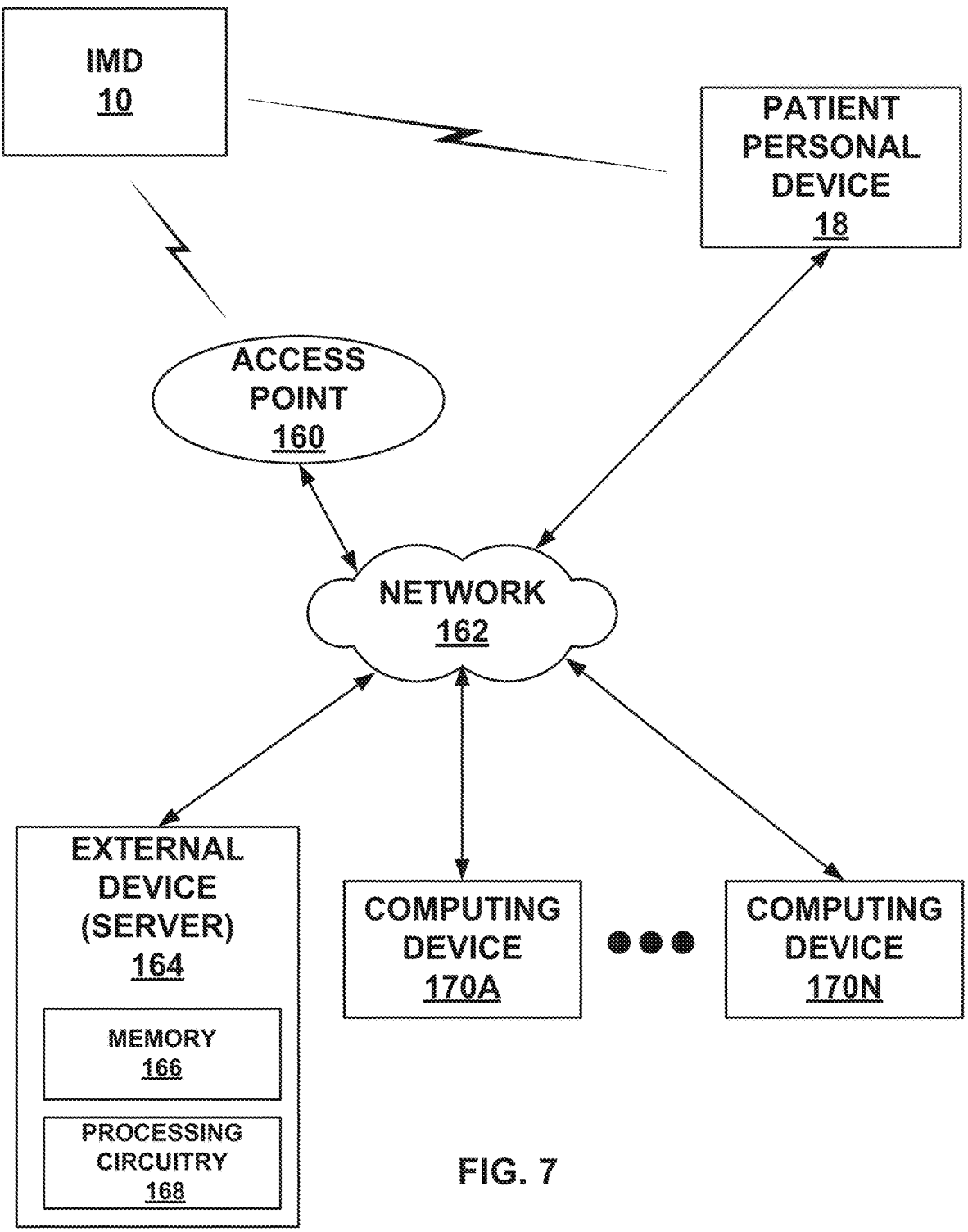
FIG. 7 is a functional block diagram illustrating an example system that includes an external device, such as a server, and one or more computing devices that are coupled to an implantable medical device and the patient personal device of FIG. 1 via a network.

FIG. 7 is a functional block diagram illustrating an example system that includes an access point 160, a network 162, external computing devices, such as a server 164, and one or more other computing devices 170A-170N, which may be coupled to IMD 10 of FIG. 5 (i.e., one or more of IMD 10A of FIGS. 1 and 2, ICD 10B of FIG. 3, and IPD 10C of FIGS. 3 and 4) and patient personal device 18 (e.g., patient personal device 18A of FIG. 1 or patient personal device 18B of FIG. 3) via network 162. In this example, IMD 10 may use communication circuitry 110 to communicate with patient personal device 18 via a first wireless connection, and to communicate with an access point 160 via a second wireless connection. In the example of FIG. 7, access point 160, patient personal device 18, server 164, and computing devices 170A-170N are interconnected and may communicate with each other through network 162.

Access point 160 may comprise a device that connects to network 162 via any of a variety of connections, such as telephone dial-up, digital subscriber line (DSL), or cable modem, or other suitable connections. In other examples, access point 160 may be coupled to network 162 through different forms of connections, including wired or wireless connections. In some examples, access point 160 may be a user device, such as a tablet or smartphone, that may be co-located with the patient. As discussed above, IMD 10 may be configured to transmit data, such as current values and heart failure statuses, to patient personal device 18. In addition, access point 160 may interrogate IMD 10, such as periodically or in response to a command from patient 4, a clinician, or network 162, in order to retrieve patient requests, symptoms, undesired effects, efficacy indications, default values 118, allowable values 120, diagnostics/feedback 122, therapy programs 124, or other information stored in memory 112 of IMD 10. Access point 160 may then communicate the retrieved data to server 164 via network 162.

In some cases, server 164 may be configured to provide a secure storage site for data collected from IMD 10 and/or patient personal device 18. In some cases, server 164 may assemble data in web pages or other documents for viewing by trained professionals, such as clinicians, via computing devices 170A-170N. One or more aspects of the illustrated system of FIG. 7 may be implemented with general network technology and functionality, which may include or be similar to that provided by the Medtronic CareLink® Network developed by Medtronic plc, of Dublin, Ireland. In some examples, such network technology and functionality may enhance the security of the communications transmitted between the components of FIG. 8, such as the communications transmitted from patient personal device to IMD 10. For example, the network technology and functionality may validate a communication, such as a patient request, transmitted from a device purporting to be patient personal device 18 and directed toward IMD 10, by confirming the identity of the device purporting to be patient personal device 18. If the network cannot confirm that the device purporting to be patient personal device 18 as indeed being patient personal device 18, then the network may not transmit the patient request to IMD 10. In other examples, the network technology and functionality similarly may validate a communication transmitted from another device, such as a device purporting to be one or more of computing devices 170A-170N (e.g., a purported remoter computer located with a clinician) toward IMD 10. In some examples, such security features may protect the cardiac pacing delivered by IMD 10 to patient 4 from being disrupted, hacked, or otherwise altered by communications originating from unauthorized sources.

In some examples, one or more of computing devices 170A-170N (e.g., device 170A) may be a remote computer, such as a smartphone, tablet or other smart device located with a clinician, by which the clinician may program, receive alerts from, and/or interrogate IMD 10. For example, the clinician may access patient requests, symptoms, undesired effects, and/or efficacy indications through device 170A, such as when patient 4 is in in between clinician visits, such as to check on one or more aspects of cardiac pacing delivered by IMD 10 or one or more aspects of patient 4's interaction with IMD 10 via application 154, as desired. In some examples, the clinician may enter medical instructions for patient 4 into an application in device 170A, such as an instruction for patient 4 to schedule a visit with the clinician or for patient 4 to seek other medical attention, based on data retrieved from IMD 10 by device 170, or based on other patient data known to the clinician. Device 170A then may transmit the instructions for medical intervention to patient personal device 18.

In further examples, patient personal device 18 may generate an alert to patient 4 based on one or more of patient requests or other information entered by patient 4 into application 154, or efficacy indications, default values 118, or diagnostics/feedback 122 determined by processing circuitry 102. In some examples, the alert generated by patient personal device 18 may include an indication that a current period of time during which IMD 10 is delivering cardiac pacing according to a requested value of a therapy parameter is ending or will be ending soon. Such indications may provide patient 4 with an opportunity to enter an updated patient request into application 154 as needed, such as when a period during which IMD 10 is delivering cardiac pacing according to a requested value is about to expire, but when patient 4 intends to continue undertaking an activity level or activity corresponding to the requested value, which may help improve clinical outcomes for patient 4.

In other examples, an alert generated by patient personal device 18 may indicate that an activity level or activity of patient 4 has significantly changed during a current period of time during which IMD 10 is delivering cardiac pacing according to a requested value of a therapy parameter. In such other examples, application 154 may display, via user interface 140, a query or request for patient 4 to indicate his or her current activity level or activity. In any such examples, such alerts may enable patient 4 identify instances in which he or she may find it beneficial to provide input, such as an updated or new patient request, to IMD 10 via application 154, which may help ensure that patient 4 receives cardiac pacing that is appropriate for patient 4's activity or activity level.

Figure 8:
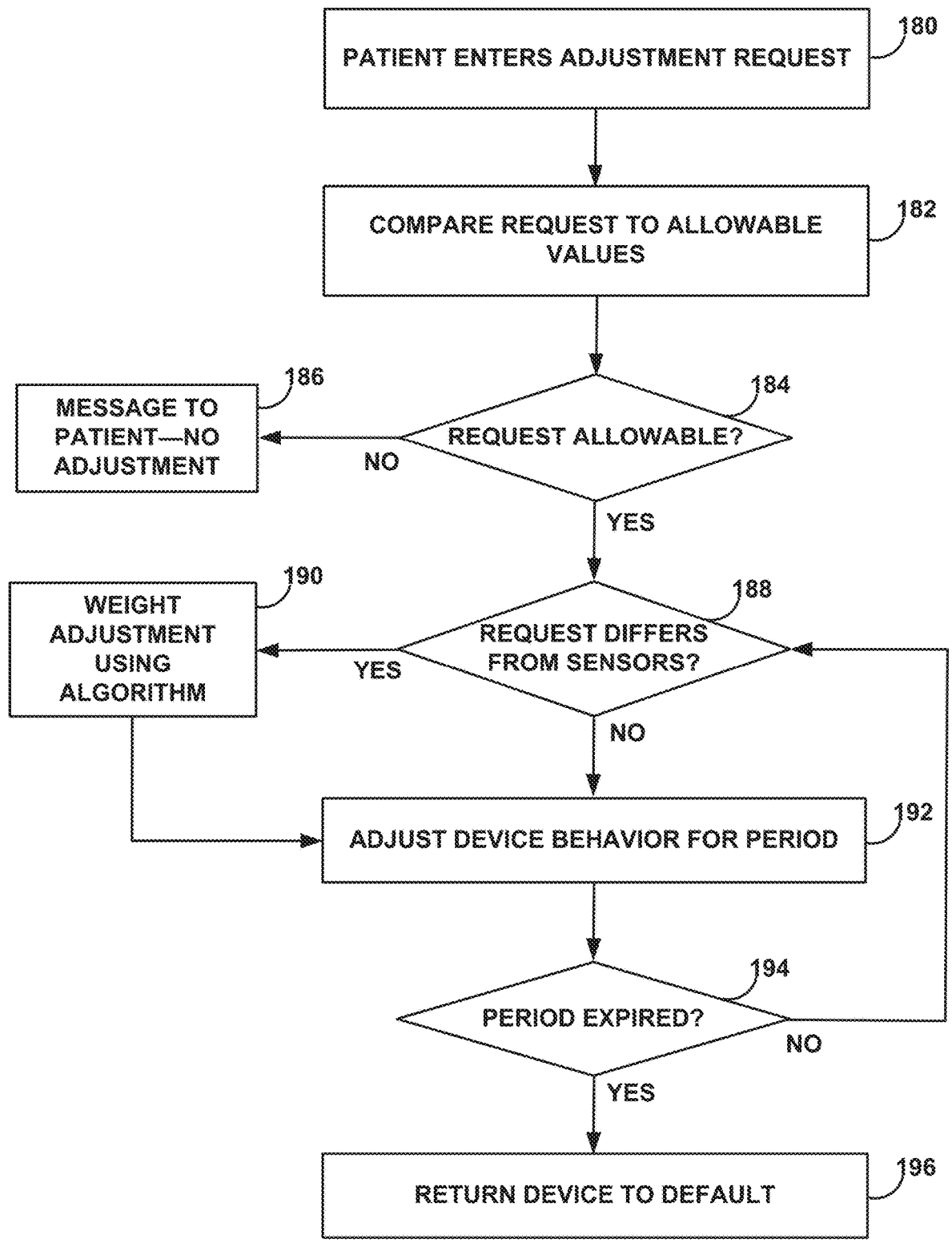
FIG. 8 is a flow diagram illustrating an example technique for controlling an implantable medical device to deliver cardiac therapy based on a patient adjustment request for a period of time.
Figure 9:
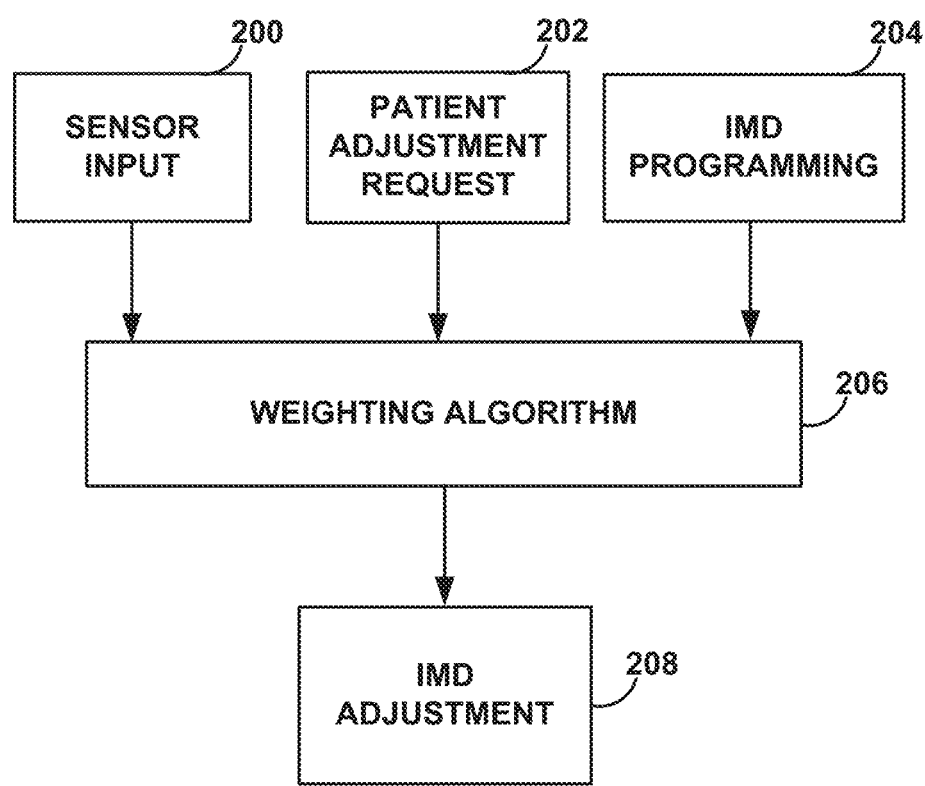
FIG. 9 is a flow diagram illustrating an example technique for adjusting, based on an output of a weighting algorithm, a value of a parameter according to which an implantable device is configured to deliver cardiac therapy.
Figure 10:
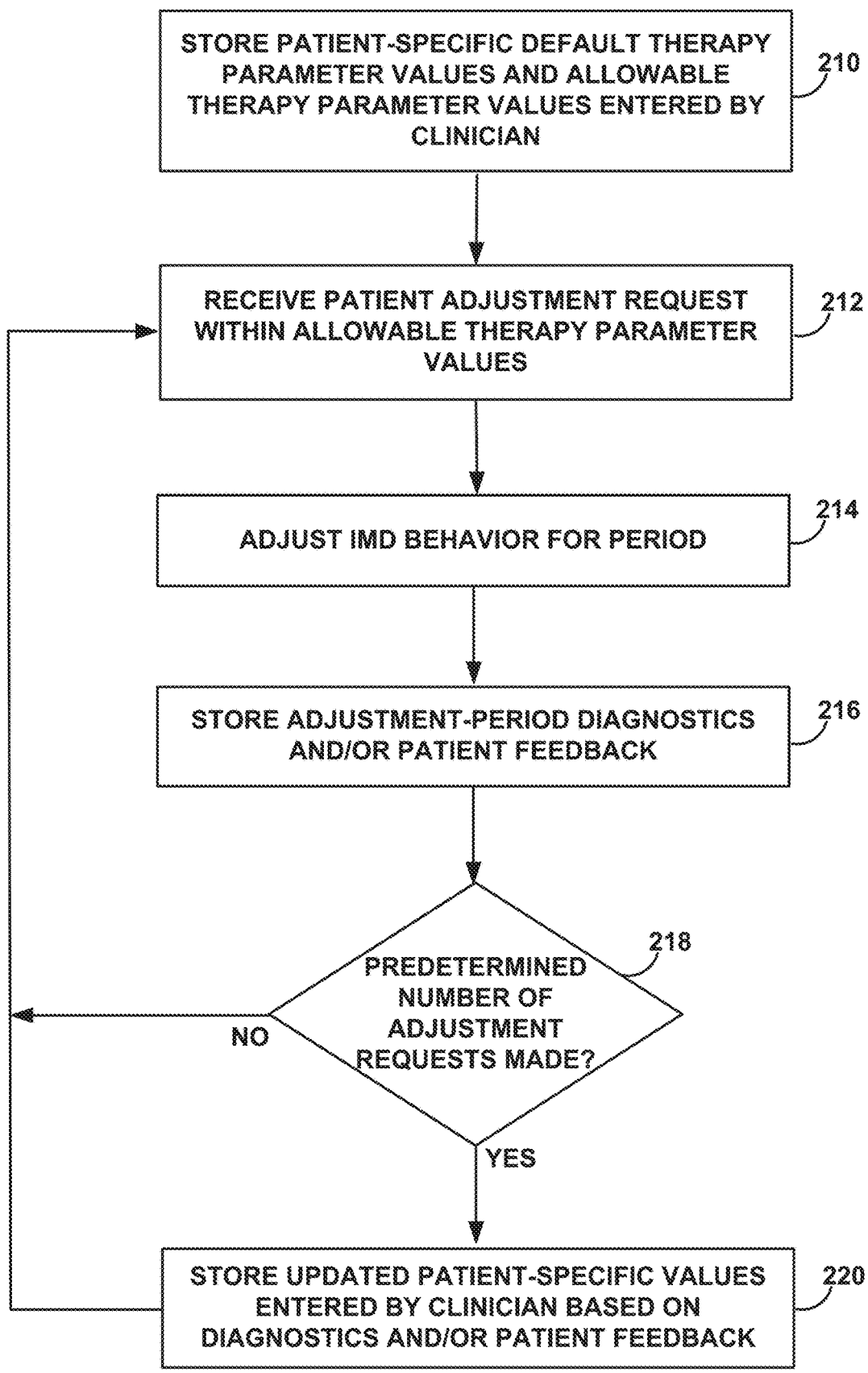
FIG. 10 is a flow diagram illustrating an example technique for updating patient-specific default therapy parameter values according to which an implantable medical device is configured to deliver cardiac therapy based on a predetermined number of patient adjustment requests.

FIGS. 8-10 are flow diagrams illustrating various techniques related to controlling the delivery of cardiac pacing by an IMD to a patient according to a requested value of a therapy parameter, in accordance with examples of this disclosure. As described herein, the techniques illustrated in FIGS. 8-10 may be employed using IMD 10, which may include components substantially similar to corresponding components of IMD 10A, ICD 10B, and/or IPG 10C, and patient personal device 18 (e.g., patient personal device 18A of FIG. 1 or patient personal device 18B of FIG. 3) in conjunction with patient 4 (e.g., patient personal device 18A of FIG. 1 or patient personal device 18B of FIG. 3), as described above with respect to FIGS. 5-7. Although described as being performed by IMD 10, the techniques of FIGS. 8-10 may be performed, in whole or in part, by processing circuitry and memory of other devices of a medical device system, as described herein. For example, although processing circuitry 102 of IMD 10 is described as carrying out most of the example techniques illustrated in FIGS. 8-10 for the sake of clarity, in other examples, one or more devices (e.g., a remote computer located with a clinician or other external device or server) may carry out one or more steps attributed herein to processing circuitry 102 of IMD 10.

FIG. 8 is a flow diagram illustrating an example technique for controlling IMD 10 to deliver cardiac therapy based on a patient adjustment request for a period of time and returning the implantable medical device to a default mode of operation after the expiration of the period. According to the example of FIG. 8, patient 4 may enter a patient request into application 154 running on patient personal device 18 (180). The patient request may be a request to adjust one or more values of one or more therapy parameters according to which IMD 10 is configured to deliver cardiac pacing to patient 4, such as a pulse rate according to which IMD 10 delivers cardiac pacing, or a request to turn off one or more non-essential pacing parameters or modes, such as APP, MVP, or others. In some examples, patient 4 may enter a patient request into application 154 proactively, such as in anticipation of undertaking an activity or activity level. In other examples, patient 4 may enter a patient request into application 154 reactively, such as in response to experiencing symptoms or undesired effects from the delivery of cardiac pacing according to a non-essential pacing parameter or mode, or in response to receiving cardiac pacing from IMD 10 according to a value of a therapy parameter that is inappropriate for an activity level or activity of patient 4.

After patient 4 enters the patient request into application 154, processing circuitry 136 of patient personal device 18 may transmit the patient request to communication circuitry 110 of IMD 10 via communication circuitry 142 of patient personal device 18. In response to receiving the patient request via communication circuitry 110 of IMD 10, IMD 10 may determine a requested value of a therapy parameter based on the patient request, and compare the requested value of the therapy parameter to allowable values 120 stored in memory 112 (182). In some examples, processing circuitry 102 may store the patient request and/or the requested value in memory 112 so as to maintain a history of patient requests received. As discussed above, IMD 10 may transmit, periodically or on demand, information pertaining to patient requests to a remote computer located with a clinician, which may enable the clinician to determine whether default values 118 and/or allowable values 120 remain appropriate for patient 4.

If processing circuitry 102 determines that the requested value does not correspond to one of allowable values 120 ("NO" at 184), then processing circuitry 102 may cause IMD 10 to transmit, via communication circuitry 110, data pertaining to the determination to communication circuitry 142 of patient personal device 18. Processing circuitry 136 of patient personal device 18 may process the data received by communication circuitry 142, and may cause application 154 to display, via user interface 140, an indication to patient 4 the indication that IMD 10 will not deliver cardiac therapy according to the requested value. Additionally, or alternatively, the indication to patient 4 via user interface 140 may indicate that a requested value of the therapy parameter associated with the patient request is not an allowable value of the therapy parameter.

If processing circuitry 102 determines that the requested value does correspond to one of allowable values 120 ("YES" at 184), then processing circuitry 102 may determine whether the requested value of the therapy parameter differs from a default value of the therapy parameter determined by processing circuitry 102. In some examples, processing circuitry may determine the default value based on one or more patient parameters, such as a heart rate of patient 4 and/or an activity level of patient 4, which processing circuitry 102 respectively may determine based on signals received from one or more of electrodes 116 and/or one or more accelerometers. If processing circuitry 102 determines that the requested value of the therapy parameter differs from the default value of the therapy parameter ("YES" at 188), then processing circuitry 102 determines a weight value based on the difference between the default value of the therapy parameter and the requested value of the therapy parameter, or a difference between a value of the therapy parameter corresponding to one of therapy programs 124 and the requested value, and determining that the difference satisfies or does not satisfy a difference threshold (190), such as by using a weighting algorithm. In some examples, processing circuitry 102 may determine the weight value by determining whether a difference between the default value of the therapy parameter and the requested value of the therapy parameter and determining that the difference satisfies or does not satisfy a difference threshold.

As discussed above, a weight value may influence a duration of the period of time for which processing circuitry 102 controls IMD 10 to deliver cardiac pacing according to the requested value of the therapy parameter. For example, if processing circuitry 102 determines that the difference does not satisfy the difference threshold, this may indicate that the default value of the therapy parameter and the requested value of the therapy parameter are similar. In some such examples, IMD 10 may deliver cardiac pacing for a period of time that may be the same as a full duration of time (e.g., a duration requested by patient 4 or associated with the requested value in one of therapy programs 124) or shorter than the full duration of time by a first length of time.

In examples in which processing circuitry 102 determines that the difference satisfies the difference threshold, this may indicate that the default value of the therapy parameter and the requested value of the therapy parameter are not similar, or at least are less similar than examples in which a difference between a default value and a requested value does not satisfy a difference threshold. In some such examples, IMD 10 may deliver cardiac pacing for a period of time that may be shorter than the full duration of time by a second length of time, which may be longer than the first length of time. Thus, in examples in which a difference between a default value and a requested value satisfies a difference threshold, processing circuitry 102 may cause IMD 10 to deliver cardiac pacing according to the requested value for a shorter period of time than examples in which a difference between a default value and a requested value does not satisfy a difference threshold. Next, processing circuitry 102 controls IMD 10 to deliver cardiac pacing according to the requested value and the weight value (192), where a duration of the period is at least partially based on the weight value.

If processing circuitry 102 determines that the requested value of the therapy parameter does not differ from the default value of the therapy parameter ("NO" at 188), then processing circuitry 102 causes (e.g., adjusts the behavior of) IMD 10 to deliver cardiac pacing according to the requested value of the therapy parameter for a period of time, which may be the full period of time (192).

In some examples, processing circuitry of 102 may determine whether the period of time has expired one or more times during delivery of cardiac pacing according to the requested value of the therapy parameter by IMD 10 (194). If processing circuitry 102 determines that the period of time has not expired ("NO" at 194), then processing circuitry 102 again may determine whether the requested value of the therapy parameter differs from a default value of the therapy parameter determined by processing circuitry 102 (188). In such examples, processing circuitry 102 may re-determine a default value of the therapy parameter upon returning to (188) after determining that the period has not expired ("NO" at 194), based on one or more patient parameters, such as a heart rate of patient 4 and/or an activity level of patient 4, which processing circuitry 102 respectively may re-determine based on signals received from one or more of electrodes 116 and/or one or more accelerometers at or around the time that processing circuitry 102 determines that the time period has not expired. Next, processing circuitry 102 compares the re-determined default value to the requested value, and may adjust the duration of the period of time based on a weight value that processing circuitry 102 may determine based on whether the difference exceeds the difference threshold. In this manner, the technique of FIG. 8 may enable ongoing adjustment of a duration of time remaining in the period, such that processing circuitry 102 may reduce a duration of time remaining in the period if processing circuitry 102 determines, for example, that an activity or activity level of patient 4 has changed during the period, which processing circuitry 102 may determine based on a change in the difference between a default value and the requested value. In such examples, it may be desirable to shorten the period, as such a change in the difference between the default value and the requested value may indicate that patient 4 has undertaken a different activity.

If processing circuitry determines that the period has expired ("YES" at 194), then processing circuitry 102 causes IMD 10 to discontinue delivering cardiac pacing according to the requested value of the therapy parameter and return to delivering cardiac pacing according to a default value (196). In some examples, the default value may be a default value determined by processing circuitry 102 during the period (192). In other examples, the default value may be a default value determined by processing circuitry 102 based on determining that the period has expired, such as based on one or more patient parameters (e.g., a heart rate of patient 4 and/or an activity level of patient 4), which processing circuitry 102 respectively may re-determine based on signals received from one or more of electrodes 116 and/or one or more accelerometers at or around (196). As described above with respect to FIG. 5, processing circuitry 102 may control IMD 10 to return to delivering cardiac pacing according to the default value by gradually increasing or decreasing a value of a therapy parameter according to which IMD 10 is delivering cardiac pacing when transitioning between the requested value and the default value (e.g., "ramping up" or "ramping down" the value of the therapy parameter), which may provide a transition between the requested value of the therapy parameter and the default value of the therapy parameter that may reduce an extent to which patient 4 perceives the return to the default value, relative to a more abrupt transition between the requested value and the default value.

After returning to delivering cardiac pacing according to the default value, IMD 10 may continue delivering cardiac pacing according to the default value until processing circuitry 102 receives another patient request associated with a requested value of a therapy parameter that corresponds to one of allowable values 120. In this manner, the technique illustrated in FIG. 8 may enable patient 4, to temporarily control delivery of cardiac pacing by IMD 10 according to a value of a therapy parameter that patient 4 may find appropriate for an activity level or activity undertaken by patient 4 at a particular time. In addition, the technique illustrated in FIG. 8 may enable a clinician to retain control over one or more aspects of cardiac pacing delivered by IMD 10, such as by comparing the requested value to allowable values 120 and/or by modifying a length of a period of time during which IMD 10 delivers therapy according to the requested value based on determining a weight value (190, 192).

FIG. 9 is a flow diagram illustrating an example technique for adjusting, based on an output of a weighting algorithm, a value of a parameter according to which IMD 10 is configured to deliver cardiac therapy, where input for the weighting algorithm includes sensor input, a patient adjustment request, and existing programming of the implantable medical device. In some examples, the technique of FIG. 9 may be carried out by processing circuitry 102 of IMD 10 at (190) and (192) of FIG. 8, at which time processing circuitry 102 may determine the weight value described above with respect to FIG. 8 and cause IMD 10 to deliver cardiac pacing according to the requested value and the weight value.

In the example technique of FIG. 9, processing circuitry 102 may determine a physiological parameter of patient 4 based on sensor input, such as a heart rate and/or an activity or activity level (200), a patient adjustment request such as a patient request (202), and IMD programming, such as one or more values of a therapy parameter associated with one of therapy programs 124 (204). Next, processing circuitry 102 executes a weighting algorithm, using as inputs to the weighting algorithm one or more of sensor input 200, patient adjustment request 202, and IMD programming 204 in determining the weight value (206). In some examples, processing circuitry may assign, via the weighting algorithm, different weights to one or more of the inputs of sensor input 200, patient adjustment request 202, and IMD programming 204. For example, processing circuitry 102 may assign greater weight to sensor input 200, such as in examples in which a requested value associated with patient adjustment request 202 is sufficiently close to an allowable value 120 that is near an extreme of a range of allowable values 120.

In other examples, processing circuitry 102 may assign greater weight to patient adjustment request 202 or IMD programming 204, such as in examples in which IMD programming 204 corresponds to one of therapy programs 124 that is associated with an activity that may be expected to result in a significant difference between a default value of a therapy parameter that processing circuitry 102 may determine based on sensor input 200 and a value of the therapy parameter associated with IMD programming 204. In any such examples, processing circuitry 102 determines the weight value based on the output of the weighting algorithm, and adjusts IMD 10 to deliver cardiac pacing according to the requested value and the weight value (208).

FIG. 10 is a flow diagram illustrating an example technique for updating default values 118 and/or allowable values 120 stored in memory 112 based on processing circuitry 102 having determined that patient 4 has made a predetermined number of patient requests. As described above, a clinician may enter one or more values of default values 118 and/or allowable values 120 into a remote computer (e.g., computing device 170A of FIG. 7), which may transmit the default values 118 and/or allowable values 120 to processing circuitry 102 via communication circuitry 110 of IMD 10. Processing circuitry 102 then may store the default values 118 and/or allowable values 120 received from the remote computer in memory 112 of IMD 10 (210).

Next, IMD 10 delivers cardiac pacing therapy to patient 4 according to the techniques described above with respect to FIGS. 1-9. For example, processing circuitry 102 of IMD 10 may receive a patient request entered by patient 4 into application 154 running on patient personal device 18 (212), and control IMD 10 to deliver cardiac pacing therapy according to a requested value of a therapy parameter associated with the patient request, for a time period, when the requested value of the therapy parameter is one of allowable values 120 (214). During or after the time period during which IMD 10 delivers cardiac pacing therapy to patient 4 according to the requested value, processing circuitry 102 may store adjustment-period diagnostics and/or feedback from patient 4 in diagnostics/feedback 122 of memory 112 (216). In some examples, diagnostics/feedback 122 may include data pertaining to one or more of patient requests, patient indications of symptoms or undesired effects, or the efficacy of cardiac pacing delivered by IMD 10. For example, diagnostics/feedback 122 may store one or more aspects of patient requests entered by patient 4 into application 154, such as requested values, requested durations, and/or associated default values. In some examples, diagnostics/feedback 122 also may store efficacy determinations, which may include an indication of a perceived efficacy of cardiac pacing entered by patient 4 into application 154, such as in response to a request for feedback from application 154. Diagnostics/feedback 122 also may store efficacy determinations made by processing circuitry 102 based on data pertaining to symptoms or undesired effects experienced by patient 4 before, during, and/or after delivery of cardiac pacing by IMD 10 at (214).

Next, processing circuitry 102 may determine whether a predetermined number of patient requests have been stored in diagnostics/feedback 122 since the clinician entered default values 118 and/or allowable values 120 in memory 112 of IMD 10 (218). If processing circuitry 102 determines that the predetermined number of patient requests have not been stored in diagnostics/feedback 122 ("NO" at 218), then the technique of FIG. 10 may return to (212). If processing circuitry 102 determines that the predetermined number of patient requests have been stored in diagnostics/feedback 122 ("YES" at 218), then processing circuitry 102 may store updated patient-specific values in memory 112, such as one or more updated default values 118 and/or one or more updated allowable values 120 (220). The one or more updated default values 118 and/or the one or more updated allowable values 120 may be received by processing circuitry 102 from a remote computer, such as computing device 170A of FIG. 7. In some examples, a clinician may enter one the one or more updated default values 118 and/or the one or more updated allowable values 120 into the remote computer (e.g., a clinician programming device separate from patient personal device 18) based on an indication, transmitted to the remote computer by communication circuitry 110 of IMD 10, that a predetermined number of patient requests have been stored in diagnostics/feedback 122. In this manner, the technique of FIG. 10 may enable a clinician to re-program memory 112 of IMD 10 with updated default values and/or updated allowable values to accommodate changing cardiac pacing needs of patient 4 remotely (e.g., without requiring an office visit by patient 4) and on an as-needed basis. Thus, the technique of FIG. 10 may help ensure that patient 4 derives one or more of the benefits associated with respect to the techniques described herein, such as an improved clinical outcome for patient 4 that may result from enabling patient 4 to provide input, such as patient requests, to IMD 10.

FIGS. 11-19 are example GUIs that display, via user interface 140 of patient personal device 18, features of application 154 with which patient 4 may interact to enter a patient request into application 154 and/or report symptoms or undesired effects that patient 4 may be experiencing. It should be understood that the example GUIs of FIGS. 11-19 are illustrative and are not intended to be limiting. In some examples, GUIs that display such features of application 154 may have a different appearance (e.g., different icons, fonts, or other graphic design elements) than the GUIs illustrated in FIGS. 11-19, while providing functionally similar elements with which patient 4 may interact. In other examples, GUIs that display such features of application 154 may include additional elements or different elements than those shown in FIGS. 11-19, while still enabling patient 4 to enter a patient request into application 154 and/or report symptoms or undesired effects.

Figure 11:
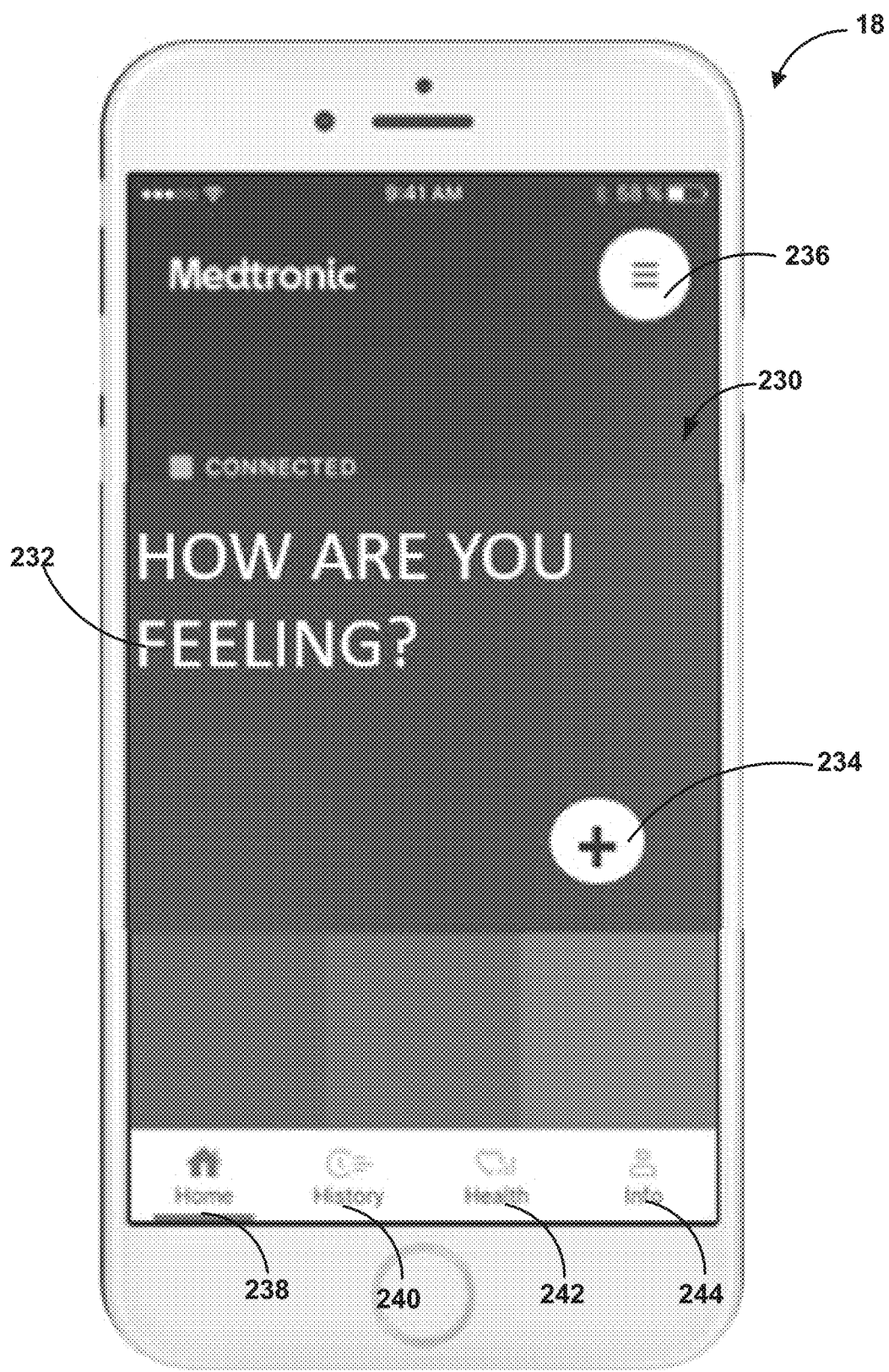
FIG. 11 is an example graphical user interface that displays an application home screen that enables a patient to initiate a request for adjusting cardiac therapy delivery by an implantable device.

FIG. 11 is an example GUI 230 that displays a home screen of application 154. GUI 230 may be configured to enable patient 4 to initiate a patient request, such as a request for IMD 10 to deliver cardiac therapy according to a requested value of a therapy parameter that patient 4 may find appropriate for an activity that patient 4 is undertaking or plans to undertake. As shown in FIG. 11, GUI 230 may include a query 232, such as "How are you feeling?" that may serve as a launch point for patient 4 to initiate the patient request. In other examples, query 232 may be have different content, such as a query asking whether patient 4 would like to initiate a patient request. GUI 230 also may include a request-initiation feature 234, which patient 4 may select to begin entering a patient request and/or a symptom or undesired effect that patient 4 may be experiencing. GUI 230 also may include a menu feature 236, which, when selected, may expand into a list of options for navigating application 154. In some examples, GUI 230 may include one or more other navigation elements, such as "home" navigation element 238, "history" navigation element 240, "health" navigation element 242, and/or "info" navigation element 244. Such additional navigation elements may provide patient 4 with additional options for moving between screens of application 154 or for providing patient 4 with an indication of a current location within application 154. For example, as shown in FIG. 11, "home" navigation element 238 is selected in GUI 230, which may indicate to patient 4 that GUI 230 is a home screen of application 154.

Figure 12:
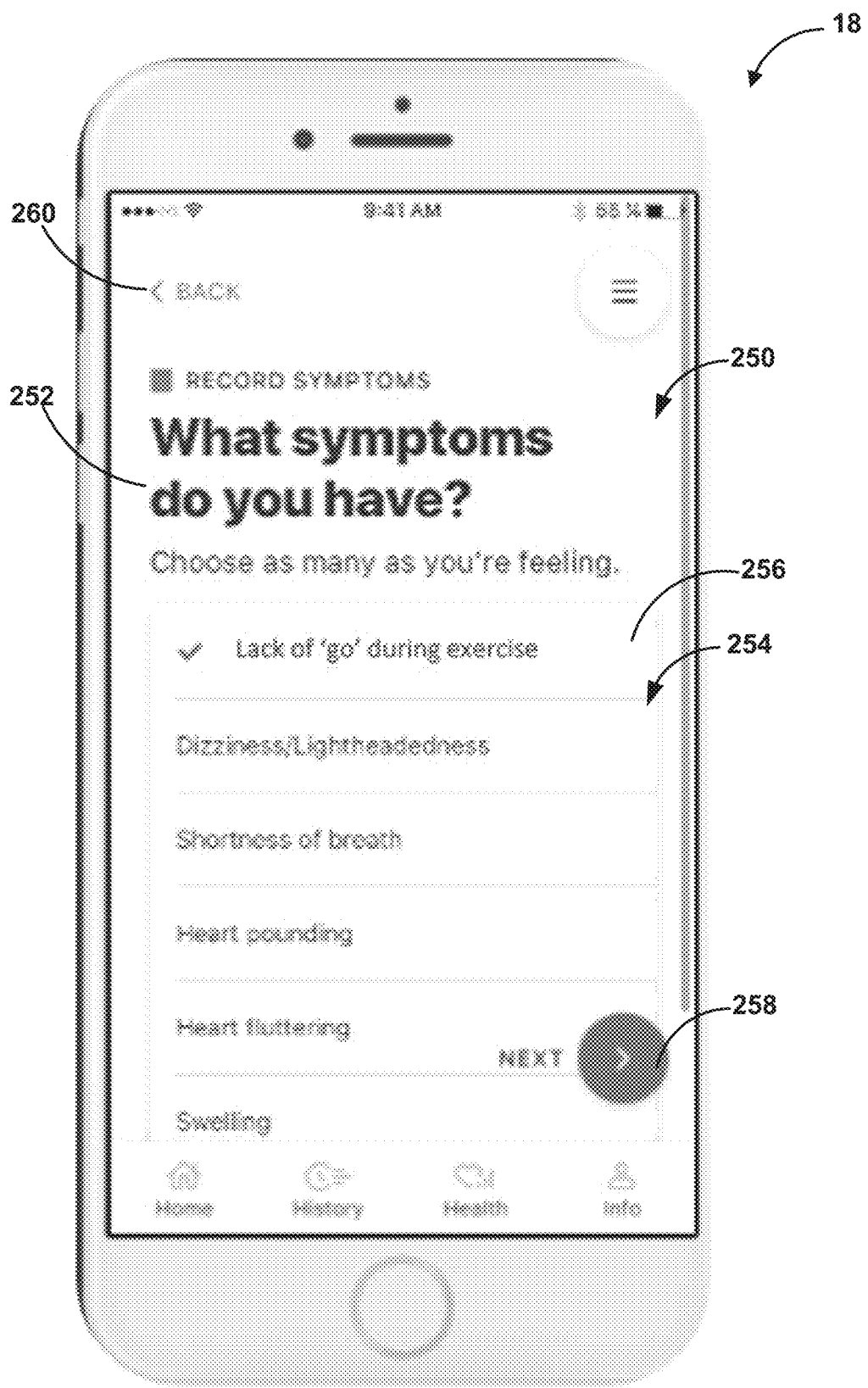
FIG. 12 is an example symptom-selection graphical user interface of the application of FIG. 11 that enables the patient to select one or more symptoms that the patient is experiencing.

FIG. 12 is an example symptom-selection GUI 250 of application 154. In some examples, user interface 140 may display GUI 250 in response to patient 4 selecting request-initiation feature 234 of GUI 230. GUI 250 may be configured to enable patient 4 to select one or more symptoms that patient 4 may be experiencing. As shown in FIG. 12, GUI 250 may include query 252, which prompts patient 4 to select one or more symptoms that patient 4 may be experiencing from symptom list 254. Patient 4 then may select one or more experienced symptoms 256 from symptom list 254. When patient 4 selects an experienced symptom 256, GUI 250 may display a check mark next to symptom 256 in symptom list 254, as shown in FIG. 12. In other examples, when patient 4 selects experienced symptom 256, GUI 250 may display a symbol next to symptom 256 other than a check mark (e.g., an "X"), shade or highlight experienced symptom 256, or otherwise provide visual confirmation that patient 4 has selected experienced symptom 256. After patient 4 has selected experienced symptom 256 from symptom list 254, patient 4 may select "next" navigation element 258 to move forward to another screen of application 154, or may select "back" navigation element 260 to move back to a previous screen of applications 154, such as the home screen displayed by GUI 230. In some examples, processing circuitry 136 of patient personal device 18 may cause communication circuitry 142 to transmit data pertaining to experienced symptom 256 selected by patient 4 to processing circuitry 102 of IMD 10 via communication circuitry 110 of IMD 10, as discussed above with respect to FIG. 6.

Figure 13:
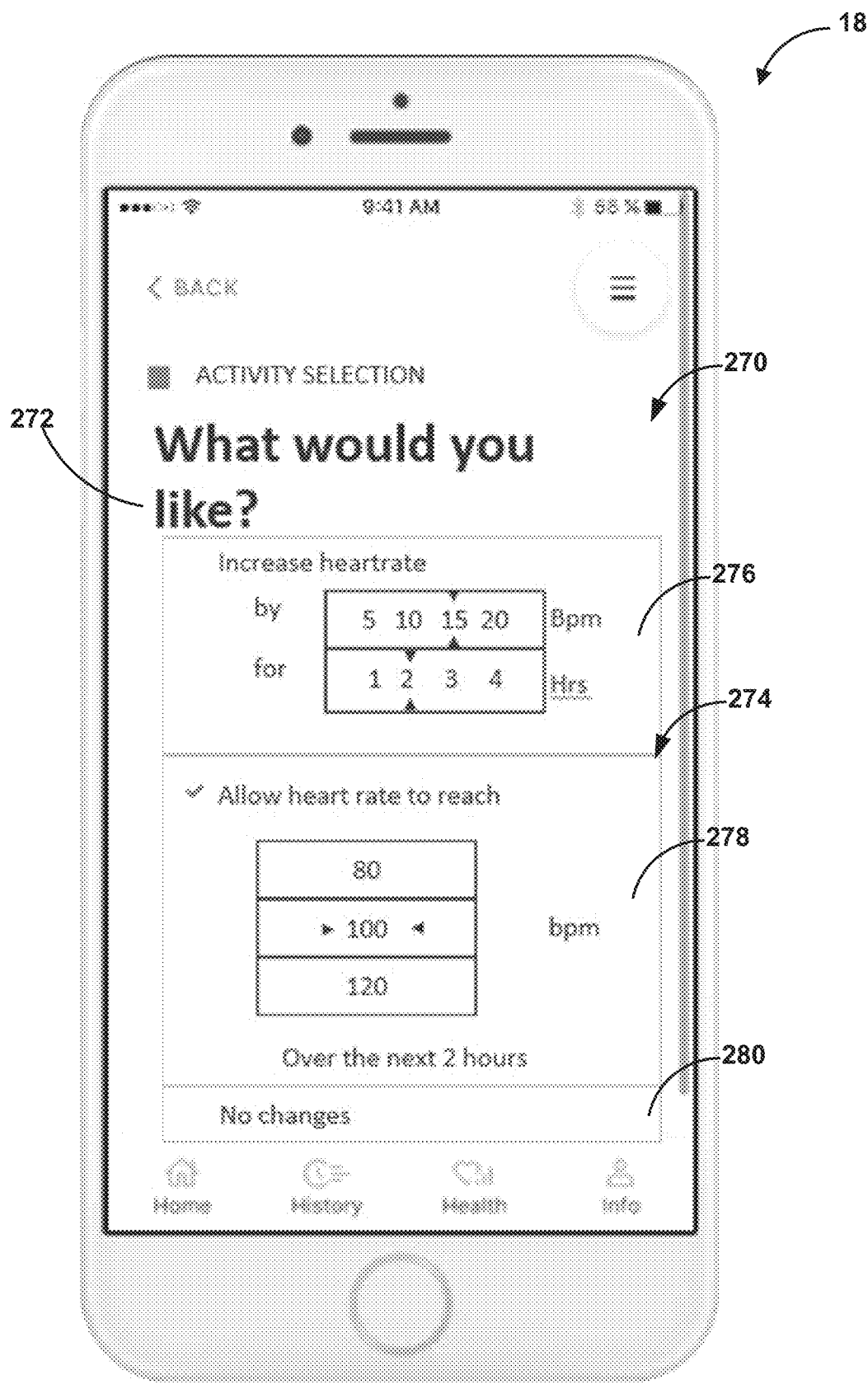
FIG. 13 is an example activity-selection graphical user interface of the application of FIG. 11 that enables the patient to request one or more values of one or more corresponding parameters according to which the implantable medical device is configured to deliver cardiac therapy.

FIG. 13 is an example patient-request entry GUI 270 of application 154. Patient-request GUI 270 ultimately may help a clinician determine whether default values 118 and/or allowable values 120 remain appropriate for patient 4. In some examples, user interface 140 may display GUI 270 in response to patient 4 selecting request-initiation feature 234 of GUI 230, or in response to patient 4 selecting "next" navigation element 258 of GUI 250. GUI 270 may be configured to enable patient 4 to enter a patient request into application 154. In the example illustrated in FIG. 12, GUI 270 may include query 272, which prompts patient 4 to select a requested value of a therapy parameter (e.g., an amount to increase a heart rate) from patient request entry element 274. In some examples, patient request entry element 274 may include heart rate and duration entry element 276, maximum heart rate entry element 278, and/or no-change entry element 280. However, in other examples, patient request entry element 274 may enable patient 4 to enter a patient request pertaining to a therapy parameter other than a heart rate. For example, patient request entry element 274 may include an element that enables patient 4 to request disabling a non-essential therapy parameter or mode, such as an APP, MVP, ARS, PMOP, or other pacing parameter or mode. In some other examples, patient request entry element 274 may include an element that enables patient 4 to request IMD 10 to deliver cardiac pacing along a different electrode vector than an electrode vector along which IMD 10A had been delivering cardiac pacing, or an element that enables patient 4 to select an MRI mode. In still other examples, patient request entry element 274 may include a list of therapy programs 124 stored in memory 112 of IMD 10.

In the example illustrated in FIG. 13, patient 4 may select one or more requested values of heart rate and duration entry element 276 and/or maximum heart rate entry element 278. In other examples, patient 4 may select no-change entry element 280, such as when patient 4 views GUI 250 but decides not to enter a patient request. In some examples, GUI 270 may display arrows, a check mark, or other indication of the requested values of heart rate and duration entry element 276 and/or maximum heart rate entry element 278, as shown in FIG. 13. After patient 4 has selected one or more requested values of heart rate and duration via element 276 and/or selected a requested value of a maximum heart rate via entry element 278, application 154 may advance to a confirmation GUI, such as the GUI described below with respect to FIG. 14. In some examples, processing circuitry 136 of patient personal device 18 may cause communication circuitry 142 to transmit data pertaining to the patient request to processing circuitry 102 of IMD 10 via communication circuitry 110 of IMD 10, as discussed above with respect to FIG. 6.

Figure 14:
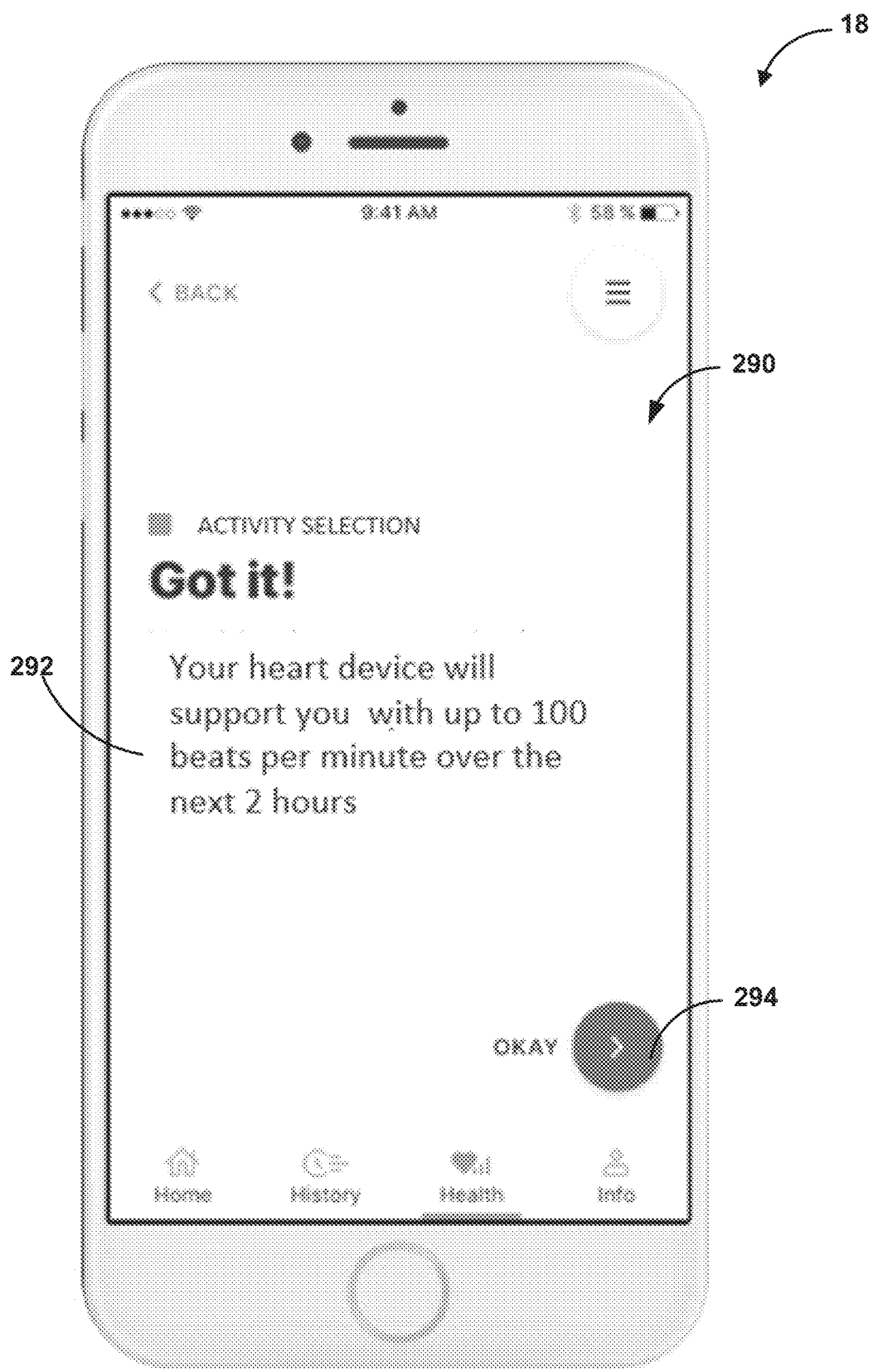
FIG. 14 is an example graphical user interface of the application of FIG. 11 that displays a confirmation message that the implantable medical device will deliver cardiac therapy based on the one or more values requested by the patient.

FIG. 14 is an example GUI 290 that displays a request-confirmation screen of application 154. As shown in FIG. 14, GUI 290 may include a confirmation message 292, which may indicate that IMD 10 will deliver cardiac pacing according to the patient request. For example, confirmation message 292 may include a requested value associated with the patient request, such as a maximum heart rate and/or a duration. In some examples, a duration included in confirmation message 292 may be based on a duration selected by patient 4 (e.g., at element 274 of GUI 270). Additionally, or alternatively, a duration included in confirmation message 292 may be based on a weight value determined by processing circuitry 102 of IMD 10, such as according to the technique of FIG. 9. In some examples, GUI may display a message indicating that one or more aspects of the patient request are not allowable (not shown), instead of displaying confirmation message 292. In such examples, the message may include an indication of which aspects of the patient request are not allowable (e.g., not corresponding to one of allowable values 120), and may suggest an alternate value as described above with respect to FIG. 1. GUI 290 also may include a patient-confirmation element 294, which patient 4 may select in response to confirmation message 292. When patient 4 selects patient-confirmation element 294, application 154 may return to the home screen displayed by GUI 230, or may advance to a GUI that may display a progression of a period during which IMD 10 delivers cardiac pacing according to the patient request.

Figure 15:
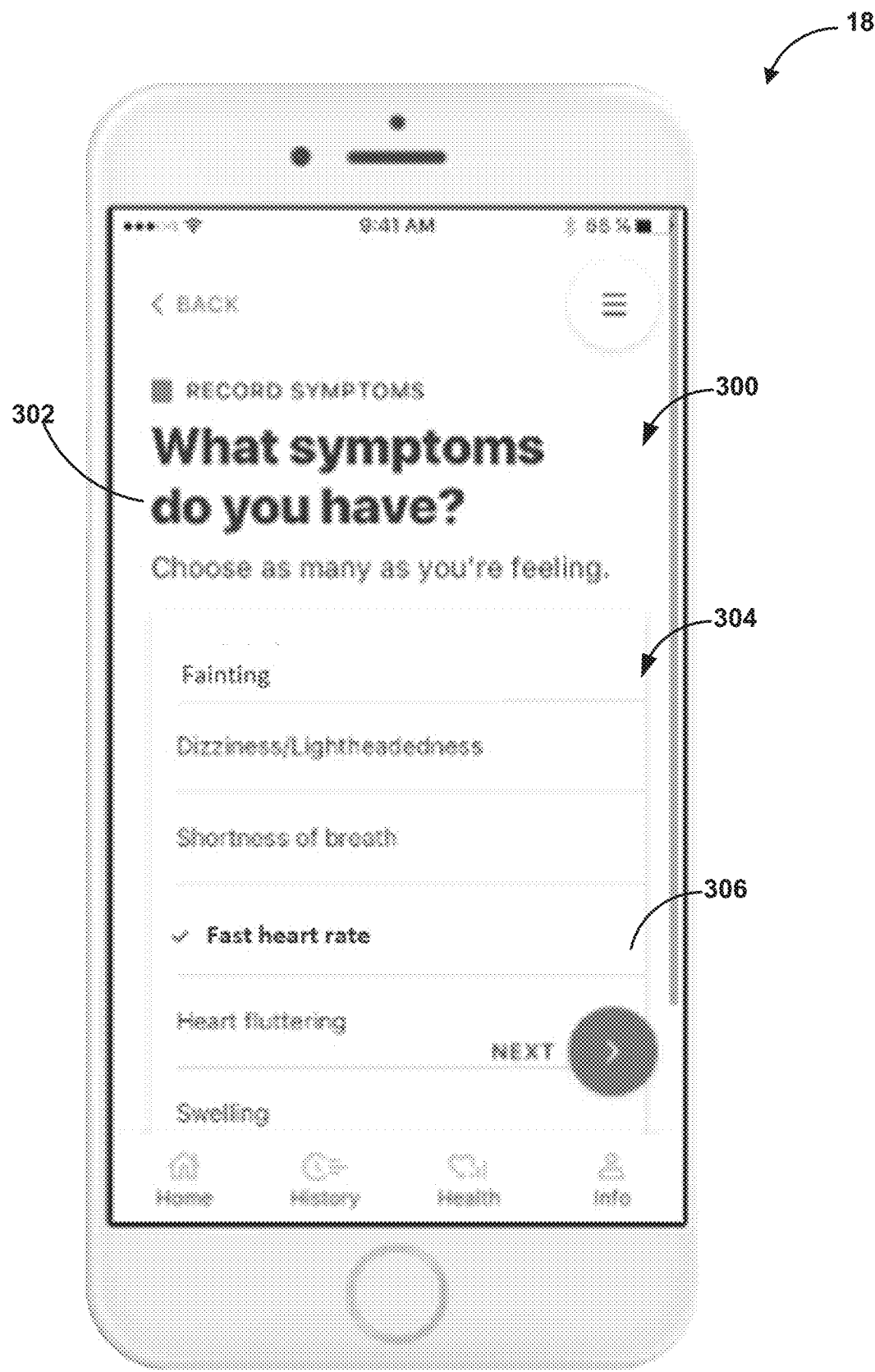
FIG. 15 is another example symptom-selection graphical user interface of the application of FIG. 11 that enables the patient to select one or more symptoms that the patient is experiencing.

FIG. 15 is another example symptom-selection GUI 300 of application 11. In some examples, one or more elements of GUI 300 may be similar to one or more elements of GUI 250 shown in FIG. 12. For example, GUI 300 may include query 302, which may be similar to query 252, symptom list 304, with which patient 4 may interact in a manner similar to which patient may interact with symptom list 254, and/or an experienced symptom 306, which patient 4 may select in response to query 302, in a manner similar to a manner in which patient 4 may select experienced symptom 256. However, in some examples, GUI 300 may differ from GUI 250 in that the symptoms listed in symptom list 304 may differ from those listed in symptom list 254. For example, the symptoms listed in symptom list 254 may include symptoms related to exercise or other patient activities, whereas the symptoms listed in symptom list 304 may include one or more other symptoms. In some other examples, symptom list 254 and symptom list 304 may be substantially similar. As with GUI 250, processing circuitry 136 of patient personal device 18 may cause communication circuitry 142 to transmit data pertaining to experienced symptom 306 selected by patient 4 to processing circuitry 102 of IMD 10 via communication circuitry 110 of IMD 10, as discussed above with respect to FIG. 6.

Figure 16:
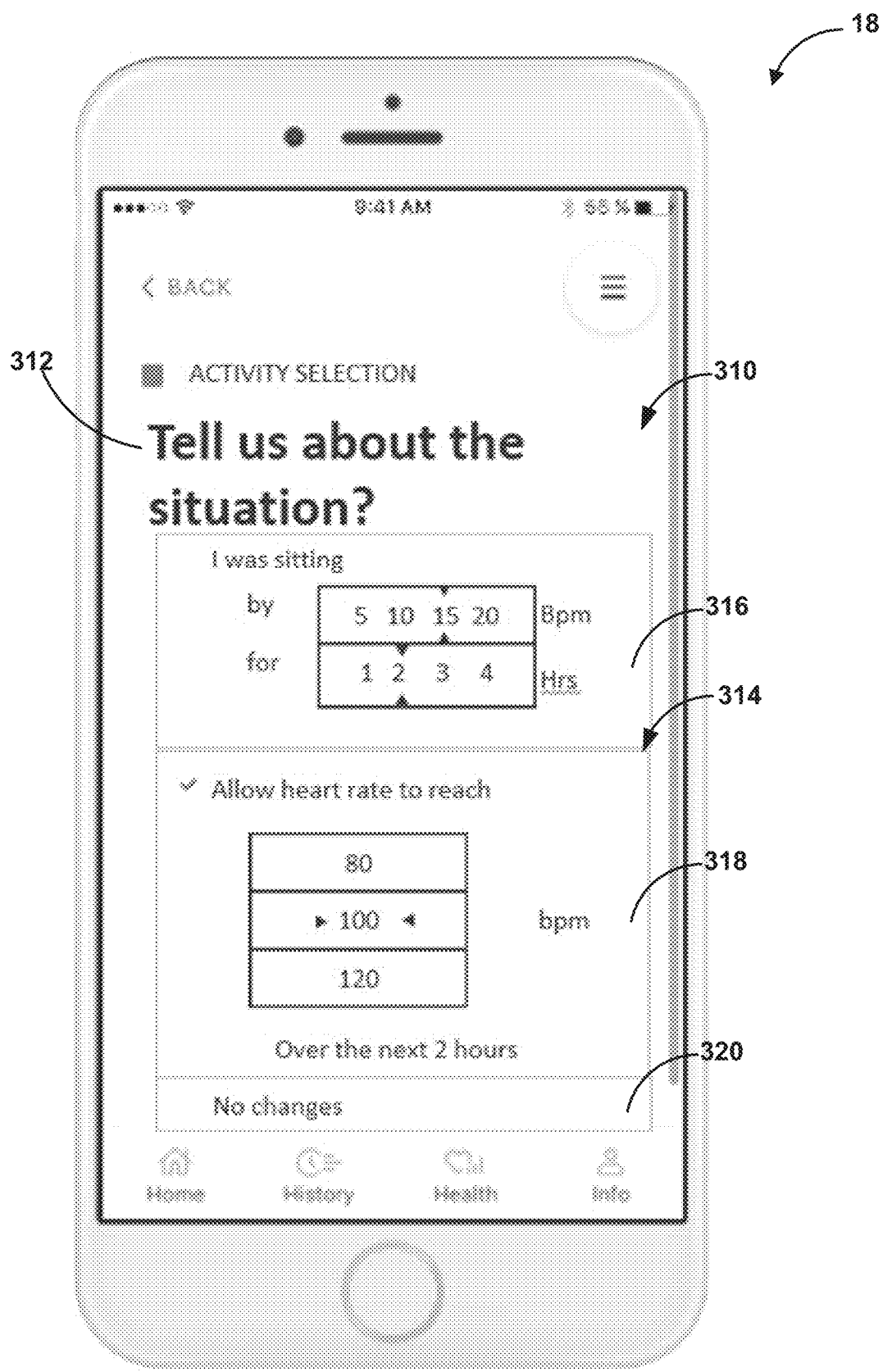
FIG. 16 is an example activity-selection graphical user interface of the application of FIG. 11 that enables the patient to provide information pertaining to circumstances in which the patient experienced a symptom.

FIG. 16 is an example activity-selection GUI 310 of application 154. Activity-selection GUI 310 may enable patient 4 to provide information pertaining to the circumstances in which patient 4 experienced a symptom, such as experienced symptom 306, which ultimately may help a clinician determine whether default values 118 and/or allowable values 120 remain appropriate for patient 4. In some examples, one or more elements of GUI 310 may be similar to one or more elements of GUI 270 shown in FIG. 13. For example, GUI 310 may include query 312, which may be similar to query 272, patient activity indicator patient request entry element 314, with which patient 4 may interact in a manner similar to which patient may interact with heart rate and duration entry element 276, maximum heart rate entry element 318, with which patient 4 may interact in a manner similar to which patient may interact with maximum heart rate entry element 278, and/or no-change entry element 320, which patient 4 may interact in a manner similar to a manner in which patient 4 may interact with no-change entry element 280. However, in some examples, GUI 300 may differ from GUI 250 in that patient activity indicator patient request entry element 314 may enable patient 4 to indicate one or more aspects of an activity that patient 4 was undertaking when a symptom occurred, such as a rate at which IMD 10 was delivering cardiac therapy and/or a duration of time that patient 4 undertook the activity. In some examples, processing circuitry 136 of patient personal device 18 may cause communication circuitry 142 to transmit data pertaining to the circumstances in which patient 4 experienced a symptom, as selected by patient 4 via element 314, to processing circuitry 102 of IMD 10 via communication circuitry 110 of IMD 10, as discussed above with respect to FIG. 6.

Figure 17:
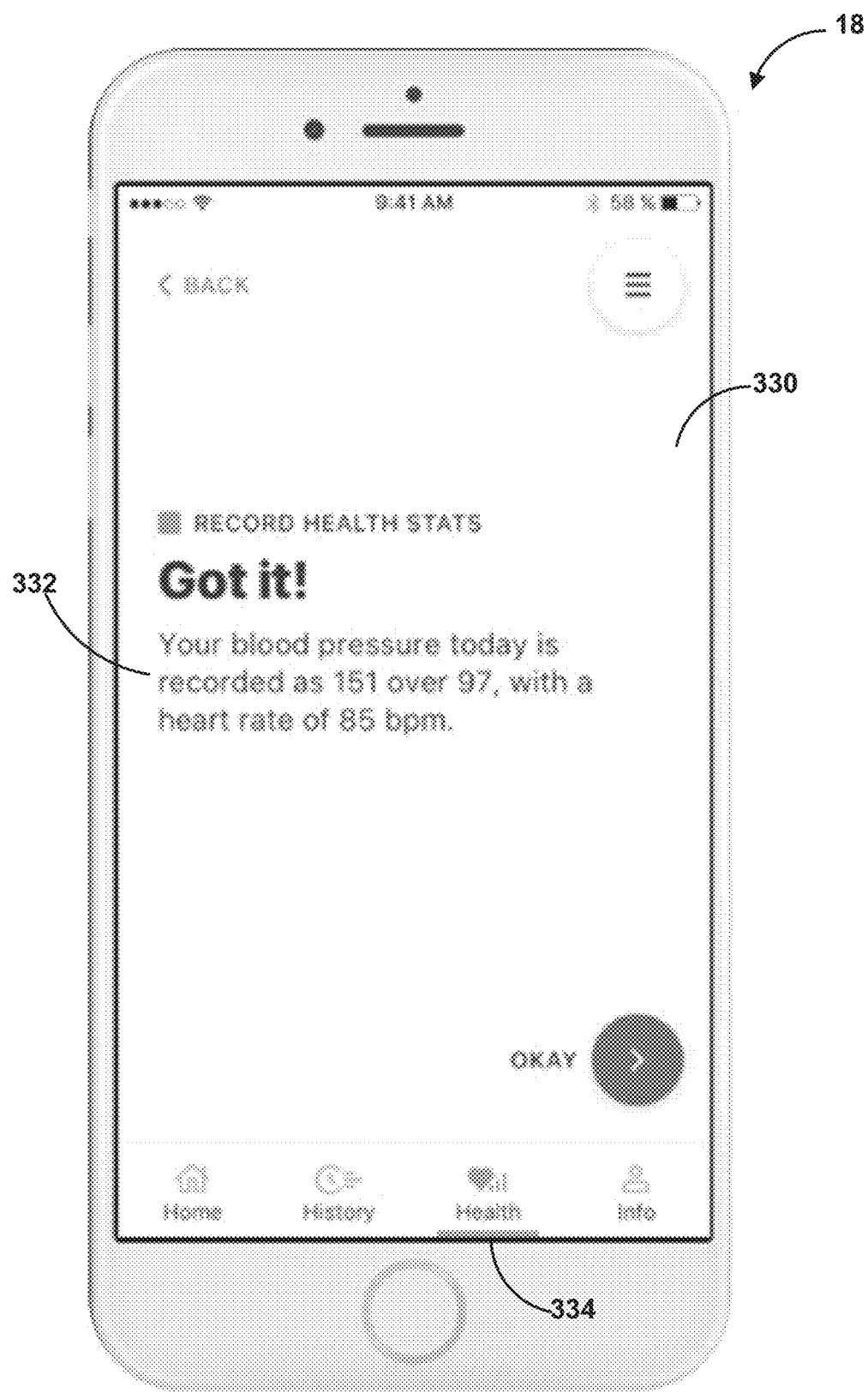
FIG. 17 is an example graphical user interface of the application of FIG. 11 that displays one or more values of one or more physiological parameters of the patient.

FIG. 17 is an example GUI 330 that displays a health-status recording screen of application 154. In some examples, GUI 330 may include confirmation message 332, which may indicate that processing circuitry 102 of IMD 10 has caused a memory, such as memory 138 of patient personal device 18 or memory 112 of IMD 10, to store one or more values of one or more physiological parameters of patient 4. Such physiological parameters may include heart rate, blood pressure, and/or other physiological parameters. In some examples, processing circuitry 102 may determine a heart rate of patient 4 based on signals received from one or more of electrodes 116, as described above.

In examples in which such physiological parameters include blood pressure, processing circuitry 102 may determine a blood pressure of patient 4 based on signals received from an IMD implanted in patient 4 and configured to sense blood pressure, such as the Reveal LINQ™ commercially available from Medtronic plc. In other such examples, processing circuitry may determine the blood pressure of patient 4 based on information entered by patient 4 into application 154, such as blood pressure value, which patient 4 may obtain by measuring his or her blood pressure with an external device. In any such examples, confirmation message 332 may include the values of the one or more physiological parameters stored by processing circuitry 102 in memory 112, as shown in FIG. 17. In some examples, GUI 330 also may include "health" navigation element 334, which may be similar to "health" navigation element 242 of FIG. 11, and which may be highlighted or otherwise selected when user interface 140 displays GUI 330. "Health" navigation element 334 may indicate to patient 4 that GUI 330 performs a health-status recording function or other function pertaining to the health of patient 4, which may enable patient 4 to navigate application 154.

In some examples, processing circuitry 136 of patient personal device 18 may cause communication circuitry 142 to transmit values of the one or more physiological parameters (e.g., the values displayed by confirmation message 332) to processing circuitry 102 of IMD 10 via communication circuitry 110 of IMD 10, as discussed above with respect to FIG. 6. In this manner, activity-selection GUI 310 may enable patient 4 to provide information pertaining to the circumstances in which patient 4 experienced a symptom, such as experienced symptom 306, which ultimately may help a clinician determine whether default values 118 and/or allowable values 120 remain appropriate for patient 4.

Figure 18:
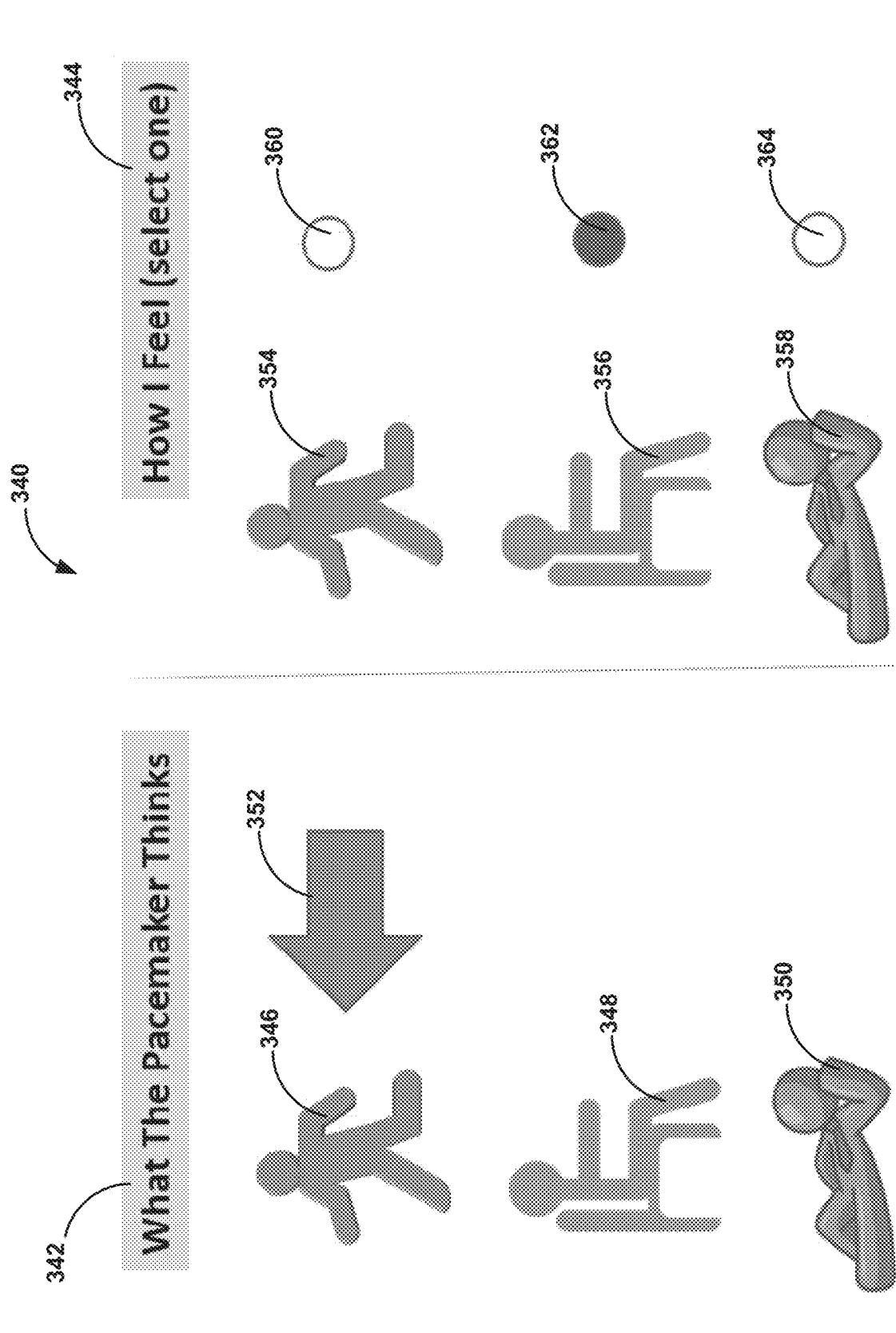
FIG. 18 is an example graphical user interface of the application of FIG. 11 that displays an activity level of the patient determined by processing circuitry of the implantable medical device and enables the patient to indicate an actual activity level of the patient.

FIG. 18 is an example GUI 340 that displays an activity-selection screen of application 154. In some examples, GUI 340 may enable patient 4 to review a level of activity or activity of patient 4 determined by processing circuitry 102 and provide input to application 154 indicating an actual level of activity or activity that patient 4 currently may be undertaking. As shown in FIG. 18, GUI 340 may include device display element 342, which indicates the level of activity or activity of patient 4 determined by a pacemaker or other device (e.g., by processing circuitry 102 of IMD 10), and an activity selection element 344, which may enable patient 4 to provide input indicating patient 4's actual activity level or activity.

Device display element 342 may include one or more icons associated with one or more corresponding patient activity levels or activities. For example, device display element 342 may include a high activity level icon 346, a moderate activity level icon 348, and a low activity level icon 350. In some examples, icons of device display element 342 may correspond to specific activities, such as running, swimming, bicycling, walking, playing a musical instrument, sitting, resting/sleeping, or other specific activities that patient 4 may undertake. In any such examples, device display element 342 also may include activity indicator 352, which may be an arrow or other visual indication of the level of activity or activity of patient 4 determined by the pacemaker or other device. For example, as shown in FIG. 18, activity indicator 352 may indicate that processing circuitry 102 has determined that an activity level of patient 4 is high. Activity indicator 352 also may indicate that IMD 10 is delivering cardiac pacing according to values of therapy parameters that correspond to the activity level of patient 4 determined by processing circuitry 102.

However, as discussed above, there may be situations in which IMD 10 may not accurately identify an activity level or activity of patient 4, such as situations in which an activity undertaken by patient 4 results in results in more or less movement, as determined by processing circuitry 102 (e.g., based on signals received from one or more accelerometers), than the level of exertion experienced by the patient would suggest. Thus, patient 4 may provide input indicating patient 4's actual activity level or activity via activity selection element 344. As shown in FIG. 18, activity selection element 344 may include a high activity level icon 354, a moderate activity level icon 356, and a low activity level icon 358. Each one of icons 354, 356, and 358 may be associated with a respective one of activity selectors 360, 262, and 364. To provide input indicating patient 4's actual activity level or activity via activity selection element 344, patient 4 may select the one of activity selectors 360, 362, and 364 associated with the one of icons 354, 356, and 358 that patient 4 perceives as corresponding to an actual activity level or activity of patient 4. As with the icons of device display element 342, the icons of activity selection element 344 may correspond to specific activities, such as running, swimming, bicycling, walking, playing a musical instrument, sitting, resting/sleeping, or other specific activities that patient 4 may undertake.

In some examples, patient 4's selection of the one of activity selectors 360, 362, and 364 may operate as a patient request for IMD 10 to deliver cardiac pacing according to one or more requested values of one or more therapy parameters that may be appropriate for patient 4's actual activity level or activity, which may differ from the activity level or activity determined by processing circuitry 102. In some such examples, one or more of activity selectors 360, 362, and 364 may be associated with one of therapy programs 124 stored in memory 112 of IMD 10, such that patient 4's selection of the one of activity selectors 360, 362, and 364 operates as a patient request for IMD 10 to deliver cardiac pacing according to a corresponding one of therapy programs 124. For example, when patient 4 selects activity selector 362, which is associated with moderate activity level icon 356, processing circuitry 102 receive the selection (e.g., via communication circuitry 142 of patient personal device 18 and communication circuitry 110 of IMD 10) and interpret the selection as a patient request to deliver cardiac pacing according to a therapy program 124 associated with a moderate activity level.

In any such examples, IMD 10 then may deliver cardiac pacing to patient 4 according to one or more requested values of one or more therapy parameters that may be associated with patient 4's selection of activity selector 362. In this manner, patient 4 may receive cardiac pacing that may be more appropriate for patient 4's actual activity level or activity than the cardiac pacing that IMD 10 may have delivered to patient 4 based on the determination of patient 4's activity level made by processing circuitry 102 and displayed in device display element 342. In some examples, processing circuitry 136 of patient personal device 18 may cause communication circuitry 142 to transmit data pertaining to patient 4's selection of the one of activity selectors 360, 362, and 364 to processing circuitry 102 of IMD 10 via communication circuitry 110 of IMD 10, as discussed above with respect to FIG. 6.

Figure 19:
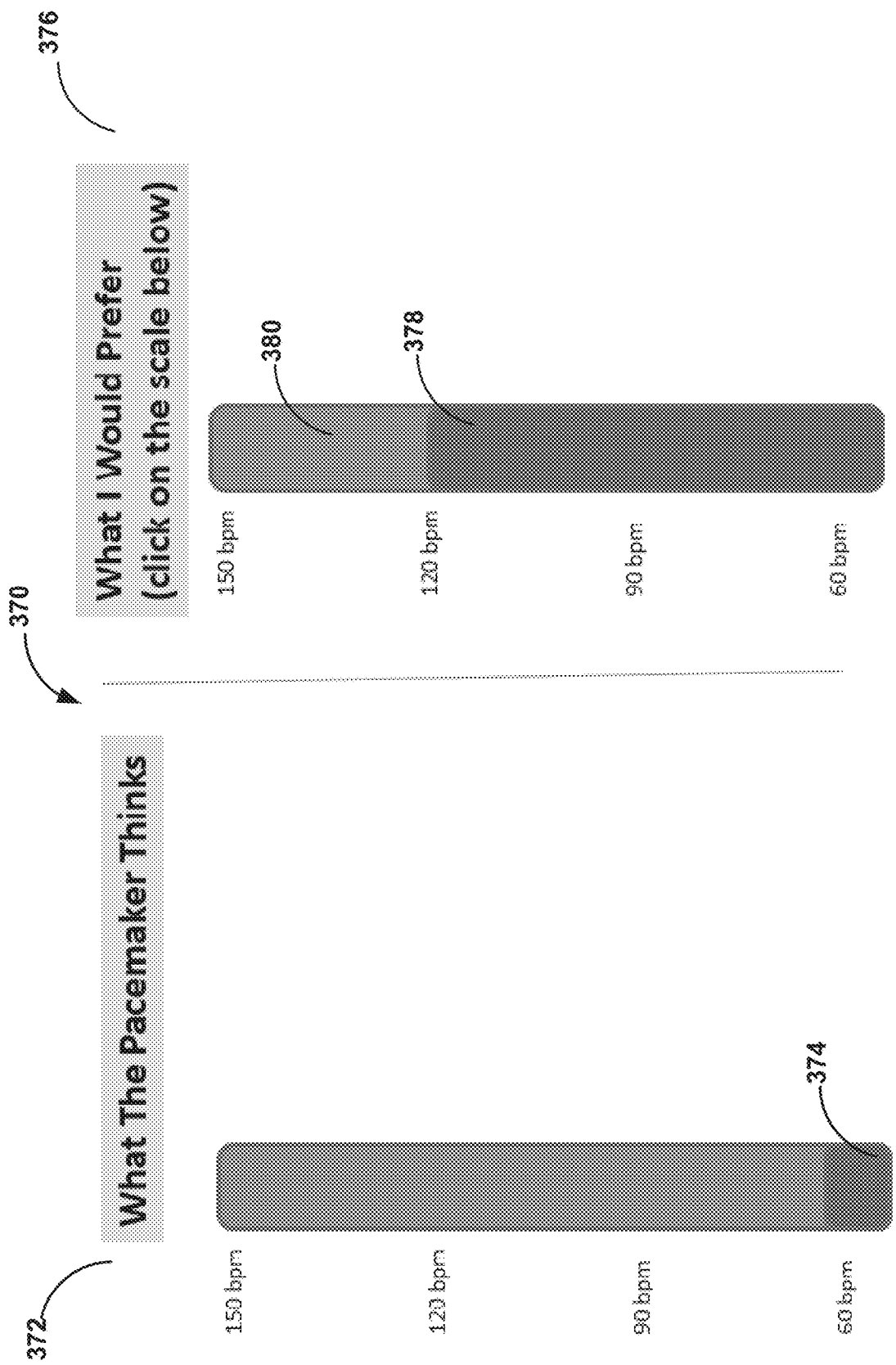
FIG. 19 is an example graphical user interface of the application of FIG. 11 that displays a current value of a parameter according to which the implantable medical device is configured to deliver therapy and enables the patient to request a value of the parameter.

FIG. 19 is an example therapy-parameter value selection GUI 370 of application 154. In some examples, GUI 370 may enable patient 4 to review a default value of a therapy parameter determined by processing circuitry 102 to be appropriate for values of one or more physiological parameters of patient 4, such as an activity level of patient 4, determined by processing circuitry 102. GUI also may enable patient 4 to provide input to application 154 indicating a requested value of the therapy parameter that patient 4 may find appropriate for one or more actual values of the one or more physiological parameters, such as an actual level of activity or activity that patient 4 currently may be undertaking. As shown in FIG. 19, GUI 370 may include a device display element 372, which indicates a default value 374 of a therapy parameter (e.g., a value of a heart rate) determined by processing circuitry 102 based on the values of the one or more physiological parameters of patient 4 (e.g., an activity level) determined by processing circuitry 102. GUI 370 also may include a value selection element 376, which may enable patient 4 to enter a patient request including a requested value 378, of the therapy parameter that patient 4 may find to be more appropriate to patient 4's actual activity level or activity than default value 374.

To enter requested value 378, patient 4 may touch, click on, or otherwise select a requested value of the therapy parameter at or near a value displayed along therapy parameter value bar 380. In some examples, therapy parameter value bar 380 may represent allowable values 120 of the therapy parameter stored in memory 112 of IMD 10. IMD 10 then may deliver cardiac pacing to patient 4 according to requested value 378. In this manner, patient 4 may receive cardiac pacing that may be more appropriate for patient 4's actual activity level or activity than the cardiac pacing that IMD 10 may have delivered to patient 4 according to default value 374. In some examples, processing circuitry 136 of patient personal device 18 may cause communication circuitry 142 to transmit data pertaining to patient 4's selection of requested value 378 to processing circuitry 102 of IMD 10 via communication circuitry 110 of IMD 10, as discussed above with respect to FIG. 6.

Although processing circuitry 102 of 100 and processing circuitry 136 of patient personal device 18 are described above as being configured to perform one or more of the steps of the techniques described with respect to FIGS. 1-19, any steps of the techniques described herein may be performed by processing circuitry of the other devices, such as the devices illustrated in FIG. 7. For example, processing circuitry of a remote computer located with a clinician (e.g., computing device 170A), or of any other suitable implantable or external device or server, may be configured to perform one or more of the steps described as being performed by processing circuitry 102 of IMD 10. In other examples, processing circuitry 102 of IMD 10, or of any other suitable implantable device, external device, or server, may be configured to perform one or more of the steps described as being performed by processing circuitry of patient personal device 18. Such other implantable or external devices may include, for example, an implantable or external monitoring device, or any other suitable device.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. A method for controlling delivery of therapy using an implantable medical device configured for implantation within a patient, the implantable medical device comprising at least one electrode and configured to deliver a cardiac pacing to the patient via the at least one electrode, the method comprising, by processing circuitry of a medical device system comprising the implantable medical device:
   receiving, from an application running on a patient personal device, a patient request entered by the patient into the application, wherein the application runs on the patient personal device to enable the patient to interact with the medical device system;
   determining, based on the patient request, a requested value of a therapy parameter according to which the implantable medical device is configured to deliver the cardiac pacing;
   determining a default value of the therapy parameter;
   determining a difference between the default value of the therapy parameter and the requested value of the therapy parameter;
   determining a weight value corresponding to the requested value of the therapy parameter based on the difference between the default value of the therapy parameter and the requested value of the therapy parameter;
   comparing the requested value of the therapy parameter to information stored in a memory of the medical device system, the information indicating one or more allowable values of the therapy parameter;
   determining that the requested value of the therapy parameter is included in the one or more allowable values of the therapy parameter based on the comparison of the requested value of the therapy parameter to the one or more allowable values of the therapy parameter; and
   controlling, based on the weight value and on determining that the requested value of the therapy parameter is included in the one or more allowable values, the implantable medical device to deliver the cardiac pacing according to the requested value of the therapy parameter for a period of time.

2. The method of claim 1, further comprising receiving, from a clinician programming device separate from the patient personal device, at least one of the information indicating the one or more allowable values of the therapy parameter or one or more the default value of the therapy parameter.

3. The method of claim 1, wherein determining the default value of the therapy parameter comprises determining the default value of the therapy parameter based on at least one of a heart rate of the patient or an activity level of the patient.

4. The method of claim 3, wherein the implantable medical device further comprises at least one sensor, the method further comprising determining the at least one of the heart rate of the patient based on a cardiac electrogram signal received from the at least one electrode and the activity level of the patient based on a signal received from the at least one sensor, wherein the therapy parameter comprises a heart rate response parameter.

5. The method of claim 1, wherein determining the weight value corresponding to the requested value of the therapy parameter based on the difference between the default value of the therapy parameter and the requested value of the therapy parameter comprises one of:
   determining that a first weight value corresponds to the requested value of the therapy parameter based on determining that the difference between the default value of the therapy parameter and the requested value of the therapy parameter does not satisfy a difference threshold; or
   determining that a second weight value corresponds to the requested value of the therapy parameter based on determining that the difference between the default value of the therapy parameter and the requested value of the therapy parameter satisfies the difference threshold, wherein the first weight value is greater than the second weight value.

6. The method of claim 5, wherein the period of time is a first period of time, wherein controlling the implantable medical device to deliver the cardiac pacing based on the first weight value and the requested value of the therapy parameter for the period of time comprises controlling the implantable medical device to deliver the cardiac pacing according to the requested value for the first period of time, and wherein controlling the implantable medical device to deliver the cardiac pacing based on the second weight value and the requested value of the therapy parameter for the period of time comprises controlling the implantable medical device to deliver the cardiac pacing according to the requested value for a second period of time, wherein the first period of time is longer than the second period of time.

7. The method of claim 1, wherein the period of time is a first period of time and the patient request comprises a request for the implantable medical device to deliver the cardiac pacing according to the requested value of the therapy parameter for a second period of time, wherein the weight value further corresponds to the second period of time, and wherein controlling the implantable medical device to deliver the cardiac pacing based on the weight value and the requested value of the therapy parameter comprises controlling the medical device to deliver the cardiac pacing for first period of time instead of the requested second period of time based on the weight value.

8. The method of claim 1, further comprising, by the processing circuitry:
   determining that the period of time has elapsed;
   controlling the implantable medical device to discontinue delivering the cardiac pacing according to the requested value of the therapy parameter based on determining that the period of time has elapsed; and
   controlling the implantable medical device to deliver the cardiac pacing according to a default value of the therapy parameter stored in the memory of the medical device system.

9. The method of claim 8, further comprising, by the processing circuitry:
storing the requested value of the therapy parameter in the memory of the medical device system;
determining an efficacy of the cardiac pacing delivered according to the requested value of the therapy parameter;
transmitting an indication of the efficacy of the cardiac pacing delivered according to the requested value of the therapy parameter to a remote computer;
receiving, from the remote computer, one or more updated allowable values corresponding to the one or more allowable values of the therapy parameter, wherein the one or more updated allowable values of the therapy parameter is based on the indication of the efficacy of the cardiac pacing delivered according to the requested value of the therapy parameter; and
storing, in the memory of the medical device system, the one or more updated allowable values of the therapy parameter.

10. The method of claim 9, further comprising, by the processing circuitry:
receiving, from the remote computer, an updated default value of the therapy parameter, wherein the updated default value is based on the indication of the efficacy; and
storing, in the memory of the medical device system, the updated default value of the therapy parameter.

11. The method of claim 9, further comprising, by the processing circuitry, transmitting instructions to the patient personal device, wherein the instructions comprise at least one of instructions to schedule a visit with a clinician, instructions for the patient to seek medical attention, and instructions for the patient to provide feedback to the medical device system via the application.

12. The method of claim 11, wherein the instructions for the patient to provide feedback to the medical device system via the application comprise instructions for the patient to provide feedback pertaining to at least one of a symptom experienced by the patient and the efficacy of the cardiac pacing delivered by the medical device according to the requested value of the therapy parameter.

13. The method of claim 1, wherein the therapy parameter comprises a heart rate response parameter, and wherein the requested value of the therapy parameter comprises a requested value of the heart rate response parameter.

14. The method of claim 13, wherein the heart rate response parameter comprises a numeric heart rate value.

15. The method of claim 13, wherein the requested value of the heart rate response parameter comprises an identity of a program stored in the memory of the medical device system that corresponds to one or more numeric heart rate values.

16. The method of claim 15, wherein the program corresponds to an activity level of the patient.

17. The method of claim 1, wherein the therapy parameter comprises one of a heart rate response parameter, a vector selection by which the implantable medical device is configured to deliver the cardiac pacing, a managed ventricular pacing (MVP) parameter, an atrial anti-tachycardia pacing (ATP) parameter, a magnetic resonance imaging (MRI)-mode parameter, an atrial preference pacing (APP) parameter, an atrial rate stabilization (ARS) parameter, and a post mode-switch overdrive pacing (PMOP) parameter, and wherein the requested value of the one of the MVP parameter, the ATP parameter, the MRI-mode parameter, the APP parameter, the ARS parameter, and the PMOP parameter comprises one of an "on" value that enables the implantable medical device to deliver the cardiac pacing according to the corresponding parameter and an "off" value that disables the implantable medical device from delivering therapy according to the corresponding parameter.

18. A system for controlling delivery of therapy using an implantable medical device configured for implantation within a patient, the system comprising:
the implantable medical device comprising at least one electrode and configured to deliver a cardiac pacing to the patient via the at least one electrode; and
processing circuitry configured to:
receive, from an application running on a patient personal device, a patient request entered by the patient into the application, wherein the application runs on the patient personal device to enable the patient to interact with the system;
determine, based on the patient request a requested value of a therapy parameter according to which the implantable medical device is configured to deliver the cardiac pacing;
determine a default value of the therapy parameter;
determine a difference between the default value of the therapy parameter and the requested value of the therapy parameter;
determine a weight value corresponding to the requested value of the therapy parameter based on the difference between the default value of the therapy parameter and the requested value of the therapy parameter;
compare the requested value of the therapy parameter to information stored in a memory of the medical device system, the information indicating one or more allowable values of the therapy parameter;
determine that the requested value of the therapy parameter is included in the one or more allowable values of the therapy parameter based on the comparison of the requested value of the therapy parameter to the one or more allowable values of the therapy parameter; and
control, based on the weight value and on determining that the requested value of the therapy parameter is included in the one or more allowable values, the implantable medical device to deliver the cardiac pacing according to the requested value of the therapy parameter for a period of time.

19. The system of claim 18, wherein the processing circuitry is further configured to receive, from a clinician programming device separate from the patient personal device, at least one of the information indicating the one or more allowable values of the therapy parameter or the default value of the therapy parameter.

20. The system of claim 18, wherein the processing circuitry is configured to determine the default value of the therapy parameter by at least determining the default value of the therapy parameter based on at least one of a heart rate of the patient and an activity level of the patient.

21. The system of claim 20, wherein the implantable medical device further comprises at least one sensor, and wherein the processing circuitry is configured to determine the at least one of the heart rate of the patient based on a cardiac electrogram signal received from the at least one electrode and the activity level of the patient based on a signal received from the at least one sensor, wherein the therapy parameter comprises a heart rate response parameter.

22. The system of claim 18, wherein the processing circuitry is configured to determine the weight value corresponding to the requested value of the therapy parameter based on the difference between the default value of the therapy parameter and the requested value of the therapy parameter by one of:
  determining that a first weight value corresponds to the requested value of the therapy parameter based on determining that the difference between the default value of the therapy parameter and the requested value of the therapy parameter does not satisfy a difference threshold; or
  determining that a second weight value corresponds to the requested value of the therapy parameter based on determining that the difference between the default value of the therapy parameter and the requested value of the therapy parameter satisfies the difference threshold, wherein the first weight value is greater than the second weight value.

23. The system of claim 22, wherein the period of time is a first period of time, wherein the processing circuitry is configured to control the implantable medical device to deliver the cardiac pacing based on the first weight value and the requested value of the therapy parameter for the period of time by at least controlling the implantable medical device to deliver the cardiac pacing according to the requested value for the first period of time, and wherein the processing circuitry is configured to control the implantable medical device to deliver the cardiac pacing based on the second weight value and the requested value of the therapy parameter for the period of time by at least controlling the implantable medical device to deliver the cardiac pacing according to the requested value for a second period of time, wherein the first period of time is longer than the second period of time.

24. The system of claim 18, wherein the period of time is a first period of time and the patient request comprises a request for the implantable medical device to deliver the cardiac pacing according to the requested value of the therapy parameter for a second period of time, wherein the weight value further corresponds to the second period of time, and wherein the processing circuitry is configured to control the implantable medical device to deliver the cardiac pacing based on the weight value and the requested value of the therapy parameter by at least controlling the medical device to deliver the cardiac pacing for first period of time instead of the requested second period of time based on the weight value.

25. The system of claim 18, wherein the processing circuitry is further configured to:
  determine that the period of time has elapsed;
  control the implantable medical device to discontinue delivering therapy according to the requested value of the therapy parameter based on determining that the period of time has elapsed; and
  control the implantable medical device to deliver the cardiac pacing according to a default value of the therapy parameter stored in the memory of the medical device system.

26. The system of claim 25, wherein the processing circuitry is further configured to:
  store the requested value of the therapy parameter in the memory of the medical device system;
  determine an efficacy of the cardiac pacing delivered according to the requested value of the therapy parameter;
  transmit an indication of the efficacy of the cardiac pacing delivered according to the requested value of the therapy parameter to a remote computer;
  receive, from the remote computer, one or more updated allowable values corresponding to the one or more allowable values of the therapy parameter, wherein the one or more updated allowable values of the therapy parameter is based on the indication of the efficacy of the cardiac pacing delivered according to the requested value of the therapy parameter; and
  storing, in the memory of the medical device system, the one or more updated allowable values of the therapy parameter.

27. The system of claim 26, wherein the processing circuitry is further configured to:
  receive, from the remote computer, an updated default value of the therapy parameter wherein the updated default value is based on the indication of the efficacy; and
  store, in the memory of the medical device system, the updated default value of the therapy parameter.

28. The system of claim 26, wherein the processing circuitry is further configured to transmit instructions to the patient personal device, wherein the instructions comprise at least one of instructions to schedule a visit with a clinician, instructions for the patient to seek medical attention, and instructions for the patient to provide feedback to the medical device system via the application.

29. The system of claim 21, wherein the instructions for the patient to provide feedback to the medical device system via the application comprise instructions for the patient to provide feedback pertaining to at least one of a symptom experienced by the patient and the efficacy of the cardiac pacing delivered by the medical device according to the requested value of the therapy parameter.

30. The system of claim 18, wherein the therapy parameter comprises a heart rate response parameter, and wherein the requested value of the therapy parameter comprises a requested value of the heart rate response parameter.

31. The system of claim 30, wherein the heart rate response parameter comprises a numeric heart rate value.

32. The system of claim 30, wherein the requested value of the heart rate response parameter comprises an identity of a program stored in the memory of the medical device system that corresponds to one or more numeric heart rate values.

33. The system of claim 32, wherein the program corresponds to an activity level of the patient.

34. The system of claim 18, wherein the therapy parameter comprises one of a heart rate response parameter, a vector selection by which the implantable medical device is configured to deliver the cardiac pacing, a managed ventricular pacing (MVP) parameter, an atrial anti-tachycardia pacing (ATP) parameter, a magnetic resonance imaging (MRI)-mode parameter, an atrial preference pacing (APP) parameter, an atrial rate stabilization (ARS) parameter, and a post mode-switch overdrive pacing (PMOP) parameter, and wherein the requested value of the one of the MVP parameter, the ATP parameter, the MRI-mode parameter, the APP parameter, the ARS parameter, and the PMOP parameter comprises one of an "on" value that enables the implantable medical device to deliver the cardiac pacing according to the corresponding parameter and an "off" value that disables the implantable medical device from delivering therapy according to the corresponding parameter.

35. A system for controlling delivery of therapy using an implantable medical device configured for implantation within a patient, the system comprising:
- means for receiving, from an application running on a patient personal device, a patient request entered by the patient into the application, wherein the application runs on the patient personal device to enable the patient to interact with the system;
- means for determining, based on the patient request, a requested value of a therapy parameter according to which the implantable medical device is configured to deliver the cardiac pacing;
- means for determining a default value of the therapy parameter;
- means for determining a difference between the default value of the therapy parameter and the requested value of the therapy parameter;
- means for determining a weight value corresponding to the requested value of the therapy parameter based on the difference between the default value of the therapy parameter and the requested value of the therapy parameter;
- means for comparing the requested value of the therapy parameter to information stored in a memory of the medical device system, the information indicating one or more allowable values of the therapy parameter;
- means for determining that the requested value of the therapy parameter is included in the one or more allowable values of the therapy parameter based on the comparison of the requested value of the therapy parameter to the one or more allowable values of the therapy parameter; and
- means for controlling, based on the weight value and on determining that the requested value of the therapy parameter is included in the one or more allowable values, the implantable medical device to deliver the cardiac pacing according to the requested value of the therapy parameter for a period of time.

36. A non-transitory computer-readable medium storing instructions for causing processing circuitry to perform a method for controlling delivery of a cardiac pacing using an implantable medical device configured for implantation within a patient, the implantable medical device comprising at least one electrode and configured to deliver the cardiac pacing to the patient via the at least one electrode, the method comprising:
- receiving, from an application running on a patient personal device, a patient request entered by the patient into the application, wherein the application runs on the patient personal device to enable the patient to interact with a medical device system;
- determining, based on the patient request, a requested value of a therapy parameter according to which the implantable medical device is configured to deliver the cardiac pacing;
- determining a default value of the therapy parameter;
- determining a difference between the default value of the therapy parameter and the requested value of the therapy parameter;
- determining a weight value corresponding to the requested value of the therapy parameter based on the difference between the default value of the therapy parameter and the requested value of the therapy parameter;
- comparing the requested value of the therapy parameter to information stored in a memory of the medical device system, the information indicating one or more allowable values of the therapy parameter;
- determining that the requested value of the therapy parameter is included in the one or more allowable values of the therapy parameter based on the comparison of the requested value of the therapy parameter to the one or more allowable values of the therapy parameter; and
- controlling, based on the weight value and on determining that the requested value of the therapy parameter is included in the one or more allowable values, the implantable medical device to deliver the cardiac pacing according to the requested value of the therapy parameter for a period of time.

\* \* \* \* \*